(12) United States Patent
Abitbol et al.

(10) Patent No.: US 8,445,203 B2
(45) Date of Patent: May 21, 2013

(54) METHOD FOR DIAGNOSING AND PREDICTING CEREBELLAR ATAXIA

(75) Inventors: Marie Abitbol, Roissy en Brie (FR); Stéphane Blot, Saint Maurice (FR)

(73) Assignees: Institut National de la Recherche Agronomique (INRA), Paris (FR); Ecole Nationale Veterinaire de Maisons Alfort, Maisons Alfort (FR)

( * ) Notice: Subject to any disclaimer, the term of this patent is extended or adjusted under 35 U.S.C. 154(b) by 123 days.

(21) Appl. No.: 13/002,143

(22) PCT Filed: Jul. 2, 2009

(86) PCT No.: PCT/IB2009/006844
§ 371 (c)(1),
(2), (4) Date: Mar. 28, 2011

(87) PCT Pub. No.: WO2010/001263
PCT Pub. Date: Jan. 7, 2010

(65) Prior Publication Data
US 2011/0281264 A1 Nov. 17, 2011

Related U.S. Application Data

(60) Provisional application No. 61/077,656, filed on Jul. 2, 2008.

(30) Foreign Application Priority Data

Jul. 2, 2008 (EP) .................................... 08305372

(51) Int. Cl.
*C07H 21/04* (2006.01)
*C12Q 1/68* (2006.01)

(52) U.S. Cl.
USPC ......... 435/6.1; 435/6.11; 435/6.12; 435/91.1; 435/91.2; 536/23.1; 536/24.3

(58) Field of Classification Search
None
See application file for complete search history.

(56) References Cited

PUBLICATIONS

Frese Marc-Andre et al, "Arylsulfatase G, a novel lysosomal sulfatase", Apr. 2008, pp. 11388-11395, vol. 283, No. 17, Journal of Biological Chemistry.
Database Registry, Chemical Abstracts Service, Columbus, Ohio, US; Claimed nucleic acid SEQ ID 258 from US6265157; May 17, 1998; XP002566552.
Database Registry, Chemical Abstracts Service, Columbus, Ohio, US; Claimed nucleic acid SEQ ID 63 from WO0226768; Apr. 18, 2002, XP002566553.
Database Registry, Chemical Abstracts Service, Columbus, Ohio, US; Claimed nucleic acid SEQ ID 5082 from JP2003259875; Oct. 9, 2003, XP002566554.
Olby Natasha et al; "Cerebellar cortical degeneration in adult American Staffordshire Terriers", Mar. 2004, pp. 201-208, vol. 18, No. 2, Journal of Veterinary Internal Medicine.
Database EMBL; Nov. 8, 2005, TPA: Canis familiaris mRNA for arylsulfatase G (arsg gene); XP002506681.
Sardiello M et al, "Sulfatases and sulfatase modifying factors: an exclusive and promiscuous relationship", Nov. 1, 2005, pp. 3203-3217, vol. 14, No. 21, Human Molecular Genetics.

*Primary Examiner* — Jeanine A Goldberg
(74) *Attorney, Agent, or Firm* — B. Aaron Schulman, Esq.; Stites & Harbison, PLLC

(57) ABSTRACT

The present invention relates to an in vitro method for diagnosing and/or predicting hereditary cerebellar ataxia in a dog, and/or identifying a dog which is healthy carrier of hereditary cerebellar ataxia, comprising determining the presence or absence of an homozygous or heterozygous genetic variation in the arylsulfatase G gene sequence in a biological sample from said dog, as compared with the arylsulfatase G gene sequence of a healthy non-carrier dog, wherein the presence of said homozygous genetic variation indicates that said dog is or will be affected by hereditary cerebellar ataxia, and the presence of said heterozygous genetic variation indicates that said dog is healthy carrier of hereditary cerebellar ataxia, said dog being of a breed selected in the group consisting of American Staffordshire Terrier, American Pit Bull Terrier and Pit Bull type.

4 Claims, 7 Drawing Sheets

METHOD FOR DIAGNOSING AND PREDICTING CEREBELLAR ATAXIA

CROSS REFERENCE TO RELATED APPLICATIONS

Figure 1:
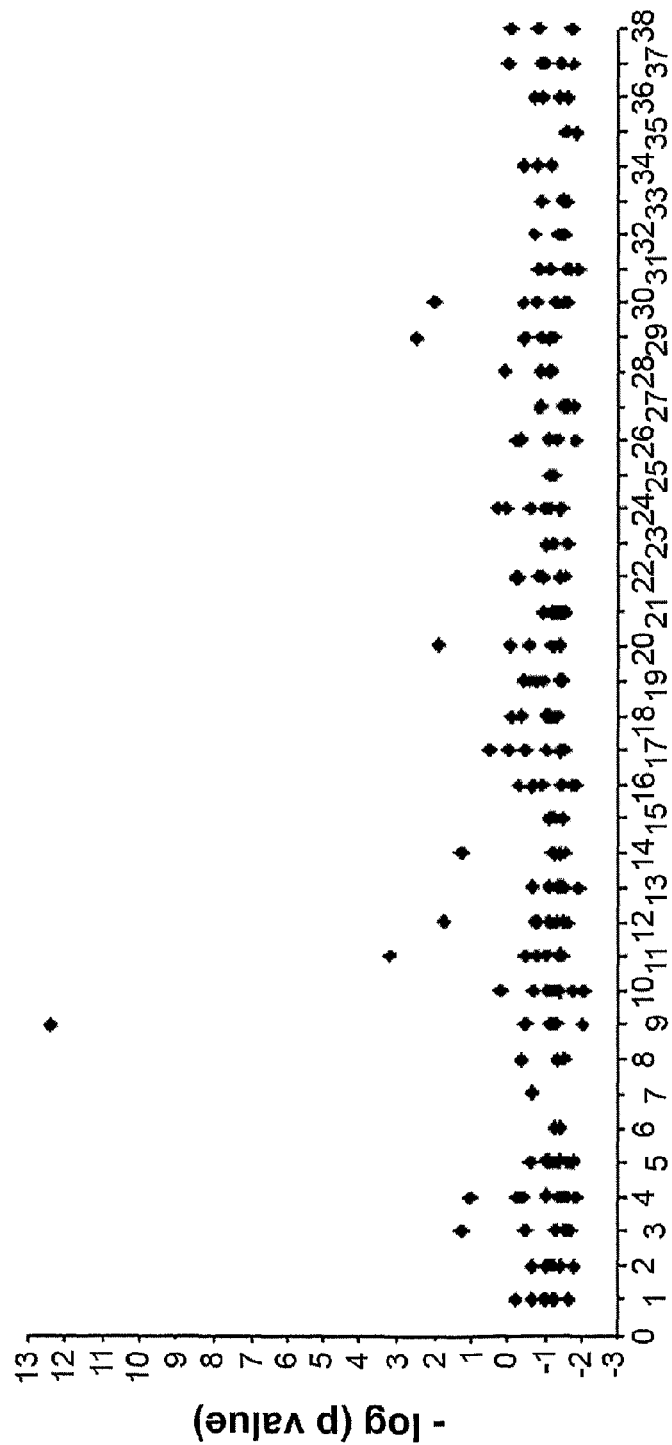

This application claims benefit of U.S. Provisional Application No. 61/077,656, filed Jul. 2, 2008 (which is hereby incorporated by reference).

FIELD OF THE INVENTION

The present invention relates to methods for diagnosing and predicting cerebellar ataxia.

BACKGROUND OF THE INVENTION

Neuronal ceroid lipofuscinoses (NCLs), a category of hereditary cerebellar ataxia, cerebellar abiotrophy or cerebellar cortical degeneration, is a group of monogenic inherited neurodegenerative storage diseases, found in men and mice, that are characterized by psychomotor retardation, blindness and premature death. In this clinically and pathologically heterogenous group of diseases, progressive loss of neuronal populations occurs within the cerebellum, specifically the Purkinje neurons and the granular cell layer. Loss of neuronal populations from other areas of the central nervous system also may occur, depending on the particular disease. This neuronal degeneration results in the insidious development of ataxia and a number of other neurological signs (depending on the disease) that progress at varying rates until the patient is incapacitated.

Similar hereditary NCLs have been reported in several domestic animals species including cattle (Houweling et al. (2006) *Biochim. Biophys. Acta* 1762:890-897), goat (Fiske and Storts (1988) *Vet. Pathol.* 25:171-173), sheep (Tammen et al. (2006) *Biochim. Biophys. Acta* 1762:898-905; Frugier et al. (2008) *Neurobiol. Dis.* 29:306-315), cat (Weissembock and Rossel (1997) *J. Comp. Pathol.* 117:17-24; Bildfell et al. (1995) *Vet. Pathol.* 32:485-488; Nakayama et al. (1993) *J. Vet. Med. Sci.* 55:829-831; Green and Little (1974) *Can. J. Comp. Med.* 38:207-212) and certain dog breeds.

The first American Staffordshire Terriers (AST) displaying the clinical and histopathological features of an adult-onset cerebellar cortical degeneration or cerebellar ataxia were diagnosed in 2002 and 2003 (Thibaud et al. European Society of Veterinary Neurology 15$^{th}$ Annual Symposium, Philadelphia Pa., September 2002; Hazliček et al. (2003) *Schweiz Arch. Tierheilkd* 145:369-375). Affected dogs showed first clinical signs from 18 months to 9 years of age with the majority of dogs presented to veterinarians between 4 and 6 years of age. They showed first stumbling, truncal sway and ataxia exacerbated by lifting the head up and negotiating stairs, progressing to an obvious ataxia characterized by dysmetria, nystagmus, coarse intention tremor and falling with transient opisthotonus. Most dogs survived for 2 to 4 years before they were euthanized while they became totally unable to walk without falling repeatedly. Histophathologic findings included loss of Purkinje cells and thinning of the molecular and granular layers.

In 2004, Siso and collaborators showed that a cerebellar cortical degeneration seen in five ASTs and eight American Pit Bull Terriers (APBT) bred in the US could be classified as a neuronal ceroid lipofuscinosis (Siso et al. (2004) *Acta Neuropathol.* 108:386-392). Indeed, they performed light microscopic, immunocytochemical and ultrastructural investigations and found that the neuronal degeneration not only affected Purkinje cells of the cerebellum but that diffuse nerve cell loss and gliosis were observed in the thalamic nuclei. They reported an accumulation of yellow-brown granules within neurones. These granules exhibited yellow autofluorescence under ultraviolet light; they were positive following periodic-acid-Shiff (PAS) and Sudan black staining thus indicating that the neuronal degeneration in these five ASTs was associated with neuronal ceroid lipofuscinosis The same year, Olby and collaborators determined that the more consistent mode of inheritance of the disease in the established pedigree of AST from the US was autosomal recessive (Olby et al. (2004) *J. Vet. Intern. Med.* 18:201-208) but the implicated gene was not identified.

Dogs displaying symptoms of the disease are therefore homozygous for the causal mutation, and healthy carrier dogs clinically undetectable and being heterozygous for the causal mutation also exist. No predicting examination is currently available to determine the status of a dog towards NCL. Indeed, only the confrontation of the breed and the age of the dog, the presence of characteristic symptoms and an MRI exam of the brain enable for diagnosing NCL in an AST.

The appearance of this disease and the apparent increase in its prevalence are of great concern for the American Staffordshire Terrier and the American Pit Bull Terrier breeds because it is an incapacitating disease for which no cure is known. Moreover, the late onset of signs results in affected dogs being bred before they develop ataxia, potentially causing wide dissemination of the disease within the breed.

Accordingly, there is a need for genetic methods to identify healthy carrier and affected dogs before breeding, in order to stop the spreading of the disease. Determination of the causal mutation of the disease is necessary to design such a method.

In humans, NCLs have been attributed to mutations in six genes, namely PPT1 (palmitoyl-protein thioesterase 1), TPP1 (tripeptidyl peptidase 1), CLN3 (ceroid lipofuscinosis, neuronal 3), CLN5, CLN6 and CLN8 (Siintola et al. (2006) *Biochim. Biophys. Acta* 1762:857-864). Mutations in three additional genes are involved in NCLs in animals. In White Swedish Landrace sheep, a mutation in the cathepsin D (CTSD) gene causes autosomal recessive congenital ovine NCL (Tyynela et al. (2000) *EMBO J.* 19:2786-2792). Furthermore, null mutations in Clcn3 (chloride channel 3), Ppt2 (palrnitoyl-protein thioesterase 2) and Ctsf (cathepsin F) are responsible for various forms of NCLs in mice (Yoshikawa et al. (2002) *Genes Cells.* 7:597-605; Gupta et al. (2001) *Proc. Natl. Acad. Sci. USA* 98:1.3566-13571; Tang et al. (2006) *Mol. Cell. Biol.* 26:2309-2316). Canine NCLs have been diagnosed in at least 18 breeds, and previous studies have found a CLN8 missense mutation associated with NCL in English Setters (Katz et al.

(2005) *Biochem. Biophys. Res. Commun.* 327:541-547), a CLN5 nonsense mutation associated with NCL in Border Collies (Melville et al. (2005) *Genomics* 86:287-294), a CTSD missense mutation associated with NCL in American Bulldogs (Awano et al. (2006) *Mol/ Genet. Metab.* 89:254-260), and a TPP1 single nucleotide deletion at CLN2 associated with NCL in Dachshunds (Awano et al. (2006) *Mol. Genet. Metab.* 89:254260). No common mutation was therefore identified according to the breed.

Method of Diagnosing and/or Predicting Hereditary Cerebellar Ataxia

The present invention arises from the finding, by the inventors, that ASTs suffering from hereditary cerebellar ataxia displayed an adenosine (A) at nucleotide position 296 of the cDNA sequence of the arylsulfatase G gene, on both alleles of the gene, whereas healthy animals displayed either a guanine (G) at nucleotide position 296 of the cDNA sequence of the arylsulfatase G gene on both alleles of the gene, or a guanine on one allele and an adenosine on the other allele at nucleotide position 296 of the cDNA sequence of the arylsulfatase G gene. In other words, ASTs suffering from hereditary cerebellar ataxia were homozygous A/A at nucleotide position 296 of the cDNA sequence of the arylsulfatase G gene, whereas healthy animals were either homozygous G/G or heterozygous G/A at nucleotide position 296 of the cDNA sequence of the arylsulfatase G gene.

Thus, the present invention relates to an in vitro method for diagnosing and/or predicting hereditary cerebellar ataxia in a dog, comprising determining the presence or absence of an homozygous genetic variation in the arylsulfatase G gene sequence in a biological sample from said dog, as compared with the arylsulfatase G gene sequence of a healthy non-carrier dog, wherein the presence of said homozygous genetic variation indicates that said dog is or will be affected by hereditary cerebellar ataxia, said dog being of a breed selected in the group consisting of American Staffordshire Terrier, American Pit Bull Terrier and Pit Bull type.

The present invention also relates to an in vitro method for identifying a dog which is healthy carrier of hereditary cerebellar ataxia, comprising determining the presence or absence of an heterozygous genetic variation in the arylsulfatase G gene sequence in a biological sample from said dog, as compared with the arylsulfatase G gene sequence of a healthy non-carrier dog, wherein the presence of said heterozygous genetic variation indicates that said dog is healthy carrier of hereditary cerebellar ataxia, said dog being of a breed selected in the group consisting of American Staffordshire Terrier, American Pit Bull Terrier and Pit Bull type.

As used herein the arylsulfatase G (ARSG) gene refers to the dog arylsulfatase G gene (including the 5' regulatory region, the promoter, the introns, the exons and the 3' regulatory region) and to fragments thereof. The arylsulfatase G gene is located on chromosome 9 (CFA09), and is shown in Genbank accession number 480460. As known from one skilled in the art, a gene includes both transcribed and untranscribed regions. The transcribed region may include introns, which are spliced out of the mRNA, and 5'- and 3'untranslated (UTR) sequences along with the protein coding sequences (exons). Accordingly, as used herein, the genomic sequence of the ARSG gene contains 5'- and 3'UTR sequences, introns and exons. Typically, the dog genomic sequence of the ARSG gene is composed of 11 exons and 10 introns. The genomic sequence of the ARSG gene is represented herein by SEQ ID NO: 2. As used herein, the American Staffordshire Terrier cDNA sequence of the ARSG gene consists of the coding sequence of the gene lacking introns. Typically, the cDNA sequence of the ARSG gene is composed of the 11 exons of the genomic sequence. It is herein represented by SEQ ID NO: 1.

In the context of the present invention, the terms "genetic variation" and "polymorphism" are used indifferently and contemplate single nucleotide substitutions, insertions and deletions of nucleotides, repetitive sequences (such as microsatellites), and the total or partial absence of genes (e.g. null mutations). More preferably, a genetic variation according to the invention is a single nucleotide polymorphism (SNP). The term "single nucleotide polymorphism" in the context of the present invention includes single base nucleotide substitutions and short deletion and insertion polymorphisms. Preferably, a SNP according to the invention is an adenosine allele of the ARSG gene.

In order to make the reading easier, the presence of an adenosine (A) at nucleotide position 296 of the cDNA sequence of the ARSG gene, will be called "adenosine allele", and the presence of a guanine (G) at nucleotide position 296 of the cDNA sequence of the ARSG gene, will be called "guanine allele".

As defined above, the cDNA sequence of the ARSG gene consists of the exons of the genomic sequence. Accordingly, a determined nucleotide position of the cDNA sequence corresponds to a determined position of the genomic sequence. In the context of the invention, the nucleotide position 296 of the ARSG gene cDNA sequence of SEQ ID NO: 1 corresponds to the nucleotide position 22139 of the ARSG gene genomic sequence of SEQ ID NO: 2. As known from one skilled in the art, introns of a gene may display numerous polymorphisms between subjects. Accordingly, a determined nucleotide position of the cDNA sequence of a gene may not correspond exactly to the same nucleotide position of the genomic sequence of the gene from a subject to another. Moreover, as the 5'-UTR sequence of the ARSG gene has not been clearly identified, the nucleotide position of the genomic sequence corresponding to the nucleotide position 296 of the cDNA sequence may slightly vary. Such a correspondence is nevertheless easily determined by one skilled in the art.

In a particular embodiment, said genetic variation is determined on the transcript or the antisense strand of the ARSG gene. As known from one skilled in the art, the sequence of the antisense strand of a gene is complementary to the sequence of the coding strand. This coding strand is transcribed in RNA, which may be spliced to form mRNA. The sequence of said mRNA is complementary to the sequence corresponding to the juxtaposition of the exons sequences contained in the coding strand. Accordingly, in the context of the invention, an adenosine allele as defined above corresponds to the presence of an uridine (U) at nucleotide position 296 of the mRNA sequence of the ARSG gene or a thymidine (T) at nucleotide position 22139 of the antisense strand sequence of the ARSG gene, and a guanine allele as defined above corresponds to the presence of a cytosine (C) at nucleotide position 296 of the mRNA sequence of the ARSG gene or at nucleotide position 22139 of the antisense strand sequence of the ARSG gene.

In the context of the invention, a genetic variation may be homozygous or heterozygous. A homozygous genetic variation means that the same genetic variation is present on both alleles of the gene carrying said genetic variation. A heterozygous genetic variation means on the contrary that said genetic variation is only present on one allele of the gene carrying said genetic variation.

As used herein, the term "American Staffordshire Terrier" (or "Amstaff") refers to a dog belonging to group 3 section 3 of the Federation Cynologique Internationale classification, standard n° :286, published on December $1^{st}$, 1997. American Staffordshire Terriers display typically the following characteristics. They are 43 to 48 cm tall. They are muscular, stocky and not long-legged. Their coat is short, close, stiff to the touch and can be of any colour. Their head has a medium length with a broad skull, a distinct stop and strong jaws. Their eyes are dark and round. Their ears are set high, cropped or uncropped, and held rose. Their tail is short in comparison to size and low set.

As used herein, the term "American Pit Bull Terrier" refers to a dog belonging to the terrier group according to the United Kennel Club classification. It is typically a medium-sized dog, solidly built, with a short coat and smooth, well-defined muscle structure. American Pit Bull Terriers display typically the following characteristics. They are muscular and stocky. Their coat is short, stiff to the touch and may be black and brown-red, brown-yellow, or black and grey or white-black. Their head has a medium length with round uniformly coloured eyes, and high set, cropped or uncropped ears. Their tail is short compared to the body length. The American Pit Bull Terrier should be both powerful and agile, the actual weight and height being less important than the correct proportion of weight to height.

As used herein, the term "Pit Bull type" refers to dogs without pedigree having at least one American Staffordshire Terrier or at least one American Pit Bull Terrier in their parents or grand-parents.

According to the invention, dogs are of a breed selected in the group consisting of American Staffordshire Terrier, American Pit Bull Terrier and Pit Bull type. More preferably, they are of a breed selected among American Staffordshire Terrier and American Pit Bull Terrier. Most preferably, they are American Staffordshire Terrier.

The terms "hereditary cerebellar ataxia", "hereditary cerebellar cortical degeneration", "neuronal ceroid lipofuscinose" and "cerebellar abiotrophy" are used herein indifferently and refer to any inherited progressive neuropathy. Preferably, said disease is a cerebellar disease which is characterized by a neuronal cell loss or by the accumulation of autofluorescent cytoplasmic granules of lipopigments in cells. Hereditary cerebellar ataxia may affect any subject which is a mammal, in particular dogs or human beings, more particularly dogs.

As used herein, the term "diagnosing" includes determining, monitoring, confirming, subclassifying and predicting of the relevant disease, disorder, complication, or risk.

As used herein, the term "predicting" refers to making a finding that a dog has a significantly enhanced probability of developing a hereditary cerebellar ataxia.

In the context of the invention, the term "healthy non-carrier" refers to a subject that is not and will not be affected by hereditary cerebellar ataxia and that will never transmit the disease to its progeny. Typically, according to the invention, a subject which is healthy non-carrier of hereditary cerebellar ataxia is homozygous G/G at nucleotide position 296 of the cDNA sequence of the ARSG gene.

In the context of the invention, the term "healthy carrier" refers to a subject that can transmit the disease to its progeny but which does not develop the disease. Typically, according to the invention, a subject which is healthy carrier of hereditary cerebellar ataxia only carries a heterozygous genetic variation in the arylsulfatase G gene. As hereditary cerebellar ataxia is an autosomal recessive disease, said subject will not develop the disease. However, it has one chance on two to transmit the allele displaying the genetic variation to its progeny. Accordingly, if the progeny also receives an allele displaying the genetic variation from the other parent, which is healthy carrier of hereditary cerebellar ataxia or is or will be affected by hereditary cerebellar ataxia, said progeny will be affected by hereditary cerebellar ataxia.

As used herein, the term "biological sample" means a substance of biological origin. In particular the biological sample comprises nucleic acids from the subject to be diagnosed. Examples of biological samples include, but are not limited to, blood and components thereof such as plasma, platelets, subpopulations of blood cells and the like; organs such as kidney, liver, heart, lung, and the like, saliva and mouth epithelial cells.

Numerous methods allowing determining the presence of a genetic variation in a biological sample are well known from the one skilled in the art. These methods include, without being limited, hybridization methods with DNA probes specific of said genetic variation, such as comparative genomic hybridization (CGH), matrix-CGH, array-CGH, oligonucleotide arrays, representational oligonucleotide microarray (ROMA), high-throughput technologies for SNP genotyping, for example Affymetrix SNP chips, and amplification methods such as quantitative PCR and real-time PCR.

Preferably, the presence or absence of said genetic variation is determined by polymerase chain reaction (PCR) and pyrosequencing, by sequencing or by specific amplification of said genetic variation. Such methods are well known to one skilled in the art. In particular, pyrosequencing is a method of DNA sequencing based on the "sequencing by synthesis" principle, wherein a single strand of DNA is sequenced by synthesizing the complementary strand along it, one base pair at a time, and detecting which base was actually added at each step. An example of pyrosequencing method is described in Ahmadian et al. (2000) *Anal. Biochem.* 280:103-110. More preferably, the presence or absence of said genetic variation is determined by quantitative PCR or by realtime PCR.

Nucleic Acids, Probes, Primers and Uses Thereof

The present invention also relates to an isolated nucleic acid comprising a sequence at least 80% identical to the sequence selected in the group consisting of SEQ ID NO: 1 and SEQ ID NO: 2, a fragment of said sequence, or a complementary sequence thereof, wherein said nucleic acid comprises an adenosine at nucleotide position 296 of SEQ ID NO: 1 or an adenosine at nucleotide position 22139 of SEQ ID NO: 2.

Said isolated nucleic acid may comprise or consist of a sequence at least 85%, 90%, 95%, 96%, 97%, 98% or 99% identical to the sequence selected in the group consisting of SEQ ID NO: 1 and SEQ ID NO: 2, to a fragment of said sequence, or a complementary sequence thereof wherein said nucleic acid comprises an adenosine at nucleotide position 296 of SEQ ID NO: 1 or an adenosine at nucleotide position 22139 of SEQ ID NO: 2.

The percentage of sequence identity is calculated by comparing the sequence of said nucleic acid optimally aligned with the reference sequence, determining the number of positions at which the identical nucleic acid base (e.g., A, T, C, G, U, or I) occurs in both sequences to yield the number of matched positions, dividing the number of matched positions by the total number of positions of the reference sequence, and multiplying the result by 100 to yield the percentage of sequence identity. Optimal alignment may be performed by Needleman-Wunsch global alignment (Needleman and Wunsch (1970) *J. Mol. Biol.* 48:443-453)

"Isolated nucleic acid" refers herein to both RNA and DNA, including cDNA, genomic DNA, and synthetic DNA. Nucleic acids can have any three-dimensional structure. A nucleic acid can be double-stranded or single-stranded (i.e., a sense strand or an antisense strand). Non-limiting examples of nucleic acids include genes, gene fragments, exons, introns, messenger RNA (mRNA), transfer RNA (tRNA), ribosomal RNA, siRNA, micro-RNA, ribozymes, cDNA, recombinant nucleic acids, and branched nucleic acids. A nucleic acid may contain unconventional or modified nucleotides. Isolated nucleic acids according to the invention may be purified or recombinant.

The fragments may be of any length, e.g. at least 10, 15, 25, 50, 100, 500 or 1000 nucleotides long.

The invention also provides for the use of said nucleic acid for diagnosing and/or predicting hereditary cerebellar ataxia in a dog of a breed selected in the group consisting of American Staffordshire Terrier, American Pit Bull Terrier and Pit Bull type, and/or for identifying a dog which is healthy carrier of hereditary cerebellar ataxia, said dog being of a breed selected in the group consisting of American Staffordshire Terrier, American Pit Bull Terrier and Pit Bull type.

The present invention also relates to a method for diagnosing and/or predicting hereditary cerebellar ataxia in a dog of a breed selected in the group consisting of American Staffordshire Terrier, American Pit Bull Terrier and Pit Bull type, and/or for identifying a dog which is healthy carrier of hereditary cerebellar ataxia, said dog being of a breed selected in the group consisting of American Staffordshire Terrier, American Pit Bull Terrier and Pit Bull type, wherein a nucleic acid as defined above is used.

The present invention also relates to an isolated probe comprising a nucleic acid as defined above.

As used herein, a "probe" refers to an oligonucleotide capable of binding in a base-specific manner to a complementary strand of nucleic acid. Isolated probes according to the invention may be purified or recombinant. They may be labelled with a detectable moiety, i.e. a moiety capable of generating a detectable signal, such as a radioactive, calorimetric, fluorescent, chemiluminescent or electrochemiluminescent signal. Numerous such detectable moieties are known in the art. By way of example, the moiety may be a radioactive compound or a detectable enzyme (e.g., horseradish peroxidase (HRP)).

In a preferred embodiment, the probe according to the invention comprises or is constituted of from about 10 to about 1000 nucleotides. Preferably, it is a fragment comprising a contiguous span of at least 12 nucleotides of SEQ ID NO: 1. Most preferably, it is a fragment consisting of a contiguous span of at least 12 nucleotides of SEQ ID NO: 1.

The present invention further relates to an isolated primer comprising a fragment of the sequence selected in the group consisting of SEQ ID NO: 1 and SEQ ID NO: 2.

As used herein, the term "primer" refers to an oligonucleotide which is capable of annealing to a target sequence and serving as a point of initiation of DNA synthesis under conditions suitable for amplification of the primer extension product which is complementary to said target sequence. The primer is preferably single stranded for maximum efficiency in amplification. Preferably, the primer is an oligodeoxyribonucleotide. The length of the primer depends on several factors, including temperature and sequence of the primer, but must be long enough to initiate the synthesis of amplification products. Preferably the primer is from 10 to 35 nucleotides in length. A primer can further contain additional features which allow for detection, immobilization, or manipulation of the amplified product. The primer may furthermore comprise covalently-bound fluorescent dyes, which confer specific fluorescence properties to the hybrid consisting of the primer and the target-sequence or non covalently-bound fluorescent dyes which can interact with the double-stranded DNA/RNA to change the fluorescence properties. Fluorescent dyes which can be used are for example SYBR-green or ethidium bromide.

In a preferred embodiment, the 3' end of the primer according to the invention is located within 800 nucleotides, more preferably within 500 nucleotides, still preferably within 100 nucleotides upstream of nucleotide position 296 of SEQ ID NO: 1 or of nucleotide position 22139 of SEQ ID NO: 2.

In a particular embodiment, the primer according to the invention comprises a contiguous span of at least 12 nucleotides of SEQ ID NO: 1 or of SEQ ID NO: 2.

Preferably, the 3' end of the primer according to the invention is located at nucleotide position 296 of SEQ ID NO: 1 or at nucleotide position 22139 of SEQ ID NO: 2, or one nucleotide upstream of nucleotide position 296 of SEQ ID NO: 1, or one nucleotide upstream of nucleotide position 22139 of SEQ ID NO:2. More preferably, the 3' end of the primer according to the invention is located at nucleotide position 296 of SEQ ID NO: 1 or one nucleotide upstream of nucleotide position 296 of SEQ ID NO: 1.

Another object of the present invention relates to a pair of primers comprising a first and a second primer each comprising a fragment of the sequence SEQ ID NO: 1 or SEQ ID NO: 2, wherein
  a) said first primer hybridizes to a first DNA strand of said arylsulfatase G gene;
  b) said second primer hybridizes to the strand complementary to said first DNA strand of arylsulfatase G gene; and
  c) the 3' ends of said first and second primers are located within 500 nucleotides of nucleotide position 296 of SEQ ID NO: 1 or of nucleotide position 22139 of SEQ ID NO: 2.

In the context of the invention, the terms "hybridize" or "hybridization," as is known to those skilled in the art, refer to the binding of a nucleic acid molecule to a particular nucleotide sequence under suitable conditions, namely under stringent conditions.

The term "stringent conditions" or "high stringency conditions" as used herein corresponds to conditions that are suitable to produce binding pairs between nucleic acids having a determined level of complementarity, while being unsuitable to the formation of binding pairs between nucleic acids displaying a complementarity inferior to said determined level. Stringent conditions are the combination of both hybridization and wash conditions and are sequence dependent. These conditions may be modified according to methods known from those skilled in the art (Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York). Generally, high stringency conditions are selected to be about 5° C. lower than the thermal melting point (Tm), preferably at a temperature close to the Tm of perfectly base-paired duplexes (Andersen, Nucleic acid Hybridization, Springer, 1999, p. 54). Hybridization procedures are well known in the art and are described for example in Ausubel, F. M., Brent, R., Kingston, R. E., Moore, D. D.,Seidman, J. G., Smith, J. A., Struhl, K. eds. (1998) Current protocols in molecular biology. V. B. Chanda, series ed. New York: John Wiley & Sons.

High stringency conditions typically involve hybridizing at about 50° C. to about 68° C. in 5×SSC/5×Denhardt's solution/1.0% SDS, and washing in 0.2×SSC/0.1% SDS at about 60° C. to about 68° C.

In a preferred embodiment, the first primer of the pair of primers as defined above comprises a contiguous span of at least 12 nucleotides of SEQ ID NO: 1; and the second primer of the pair of primers as defined above comprises a contiguous span of at least 12 nucleotides of a sequence complementary to SEQ ID NO: 1.

More preferably, the 3' end of the first primer of the pair of primers as defined above is located at nucleotide position 296 of SEQ ID NO: 1 or at nucleotide position 22139 of SEQ ID NO: 2 or one nucleotide upstream of nucleotide position 296 of SEQ ID NO:1 or one nucleotide upstream of nucleotide position 22139 of SEQ ID NO: 2, and the 3' end of the second primer of the pair of primers as defined above is located at nucleotide position 296 of a sequence complementary to SEQ ID NO: 1, or at nucleotide position 22139 of a sequence complementary to SEQ ID NO: 2, or one nucleotide upstream of nucleotide position 296 of a sequence complementary to SEQ ID NO: 1, or one nucleotide upstream of nucleotide position 22139 of a sequence complementary to SEQ ID NO: 2.

Most preferably, the 3' end of the first primer of the pair of primers as defined above is located at nucleotide position 296 of SEQ ID NO: 1 or one nucleotide upstream of nucleotide position 296 of SEQ ID NO: 1 and the 3' end of the second primer of the pair of primers as defined above is located at nucleotide position 296 of a sequence complementary to SEQ ID NO: 1 or one nucleotide upstream of nucleotide position 296 of a sequence complementary to SEQ ID NO: 1.

The nucleic acids, the probes, the primers and the pairs of primers according to the invention can be used to determine the presence or absence of an homozygous genetic variation in the arylsulfatase G gene sequence in a biological sample from a dog to be diagnosed, wherein the presence of said homozygous genetic variation indicates that said dog is or will be affected by hereditary cerebellar ataxia. Preferably, the nucleic acids, the probes, the primers and the pairs of primers according to the invention are used to determine the presence or not of an adenosine allele at the nucleotide position 296 of the cDNA sequence of the arylsulfatase G gene or at the nucleotide position 22139 of the genomic sequence of the arylsulfatase G gene, more preferably of an adenosine allele at the nucleotide position 296 of SEQ ID NO: 1 or at the nucleotide position 22139 of SEQ ID NO: 2.

It also relates to the use of respectively a nucleic acid, a probe, a primer and a pair of primers as defined above for identifying a dog which is healthy carrier of hereditary cerebellar ataxia, said dog being of a breed selected in the group consisting of American Staffordshire Terrier, American Pit Bull Terrier and Pit Bull type.

Namely, the nucleic acids, the probes, the primers and the pairs of primers according to the invention can be used to determine the presence or absence of heterozygous genetic variation in the arylsulfatase G gene sequence in a biological sample from a dog to be diagnosed, wherein the presence of said heterozygous genetic variation indicates that said dog is healthy carrier of hereditary cerebellar ataxia. Preferably, the nucleic acids, the probes, the primers and the pairs of primers according to the invention are used to determine the presence or not of an adenosine allele at the nucleotide position 296 of the cDNA sequence of the arylsulfatase G gene or at the nucleotide position 22139 of the genomic sequence of the arylsulfatase G gene, more preferably of an adenosine allele at the nucleotide position 296 of SEQ ID NO: 1 or at the nucleotide position 22139 of SEQ ID NO: 2.

Arrays and Kits

The present invention also relates to an array for diagnosing and/or predicting hereditary cerebellar ataxia in a dog of a breed selected in the group consisting of American Staffordshire Terrier, American Pit Bull Terrier and Pit Bull type and/or for identifying a dog which is healthy carrier of hereditary cerebellar ataxia, said dog being of a breed selected in the group consisting of American Staffordshire Terrier, American Pit Bull Terrier and Pit Bull type, wherein said array comprises probes as defined above.

In a particular embodiment, the probes as defined above are assembled on a same solid support, preferably a standardized support. Its size can vary according to the apparatuses used to detect the presence or absence of a genetic variation as defined above.

Advantageously, the combination of probes according to the invention is in form of a DNA matrix, comprising a support on which probes likely to hybridize to target sequences are deposed, preferably in a standardized way. The size of such supports varies according to the preparation and detection methods used. Such small supports are also referred to array.

As used herein, the term "array" refers to a set of genes, fragment of genes, oligonucleotides deposited on a support (glass slide, nylon membrane . . . ) with a high density. Numerous scientific publications about the preparation and the use of arrays are available.

The present invention further relates to a kit for diagnosing and/or predicting hereditary cerebellar ataxia in a dog of a breed selected in the group consisting of American Staffordshire Terrier, American Pit Bull Terrier and Pit Bull type, and/or for identifying a dog which is healthy carrier of hereditary cerebellar ataxia, said dog being of a breed selected in the group consisting of American Staffordshire Terrier, American Pit Bull Terrier and Pit Bull type, wherein said kit comprises primers or a pair of primers as defined above.

Genotyping

The present invention also relates to the use of a nucleic acid as defined above, for genotyping a dog being of a breed selected in the group consisting of American Staffordshire Terrier, American Pit Bull Terrier and Pit Bull type, wherein said dog suffers of hereditary cerebellar ataxia.

The present invention further relates to a method for genotyping a dog being of a breed selected in the group consisting of American Staffordshire Terrier, American Pit Bull Terrier and Pit Bull type, wherein said dog suffers of hereditary cerebellar ataxia, wherein a nucleic acid as defined above is used.

As used herein, the term "genotyping" a dog involves determining at least one specific allele or specific nucleotide carried by a dog at at least one gene of interest.

In particular, in the context of the invention, said specific nucleotide is at the nucleotide position 296 of the arylsulfatase G gene cDNA sequence of SEQ ID NO: 1 or at the nucleotide position 22139 of the arylsulfatase G gene genomic sequence of SEQ ID NO: 2 and said gene of interest is arylsulfatase G gene.

Any well-known method of genotyping may be used in the frame of the present invention. Such methods include methods such as e.g. conventional dot blot analyzes, single strand conformational polymorphism analysis, denaturing gradient gel electrophoresis, heteroduplex analysis and mismatch cleavage detection. Another method for determining the identity of the nucleotide present at a particular polymorphic site employs a specialized exonuclease-resistant nucleotide derivative as described in U.S. Pat. No. 4,656,127. Oligonucleotide microarrays or solid-phase capturable dideoxynucleotides and mass spectrometry may also be used. Preferred methods involve directly determining the identity of the nucleotide present at a specific nucleotide position by sequencing assay, enzyme-based mismatch detection assay, or hybridization assay.

The present inventors identified the mutation in the arylsulfatase G gene defined above, associated with hereditary cerebellar ataxia, by sequencing a representative number of dogs suffering of hereditary cerebellar ataxia. Nevertheless, it cannot be excluded that other mutations in the arylsulfatase G gene exist that are associated with said disease. Accordingly, the present invention also relates to a method of identifying mutations in the arylsulfatase G gene associated with hereditary cerebellar ataxia, by genotyping a dog being of a breed selected in the group consisting of American Staffordshire Terrier, American Pit Bull Terrier and Pit Bull type, wherein said dog suffers of hereditary cerebellar ataxia.

The invention will be further illustrated by the following figures and examples.

FIGURES

FIG. 1 shows the genome-wide association mapping of the NCL of the AST. Results of the whole genome scan performed with the MSS2 (minimal screening set 2) panel and 38 healthy and 39 affected French dogs are displayed. A single locus with strong significance was identified on CFA09. The Bonferroni corrected —log(pvalue) were calculated with STRAT software and reported on the y axis.

Figure 2:
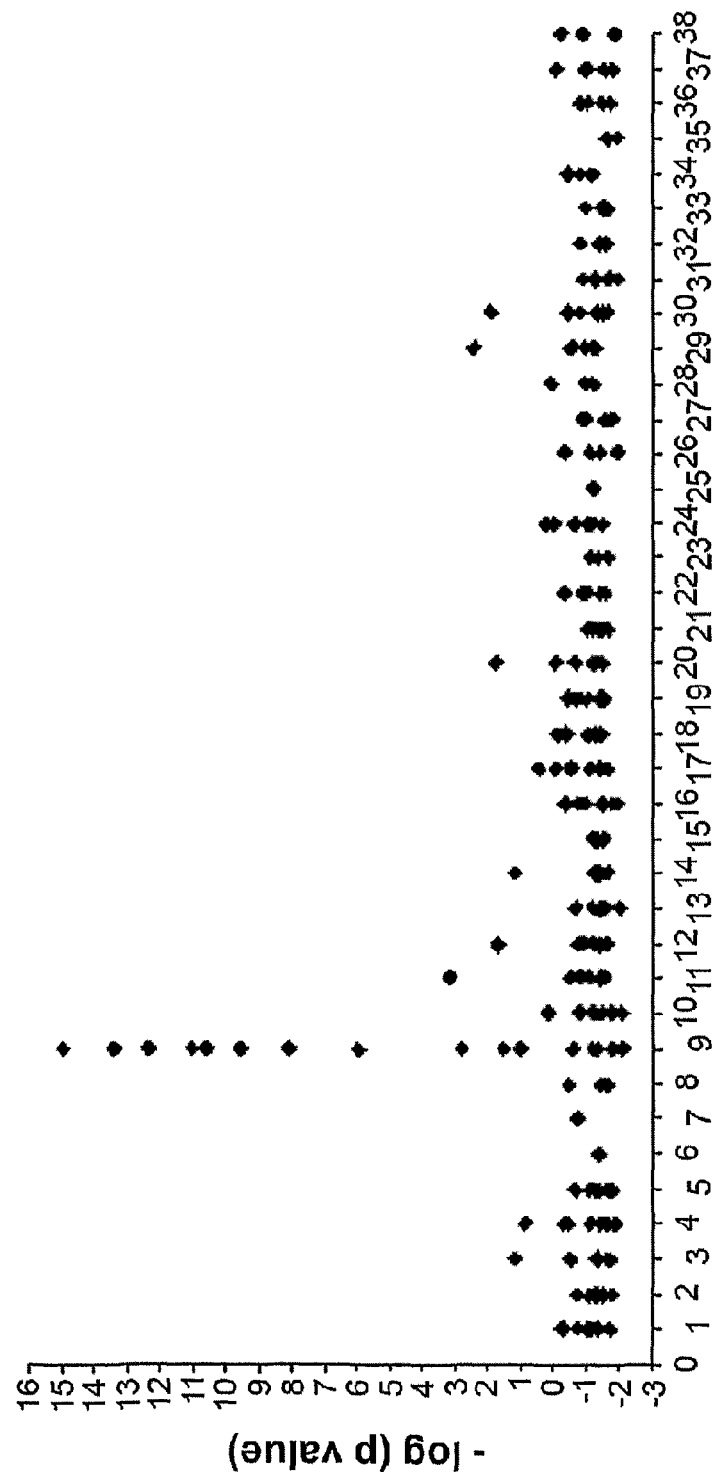

FIG. 2 shows the completed genome-wide association mapping of the NCL of the French AST. It displays the results of the whole genome scan with the MSS2 panel completed with 14 new SNPs and microsatellites markers located on CFA09. The Bonferroni corrected—log(pvalue) were calculated with STRAT software and reported on the y axis.

Figure 3:
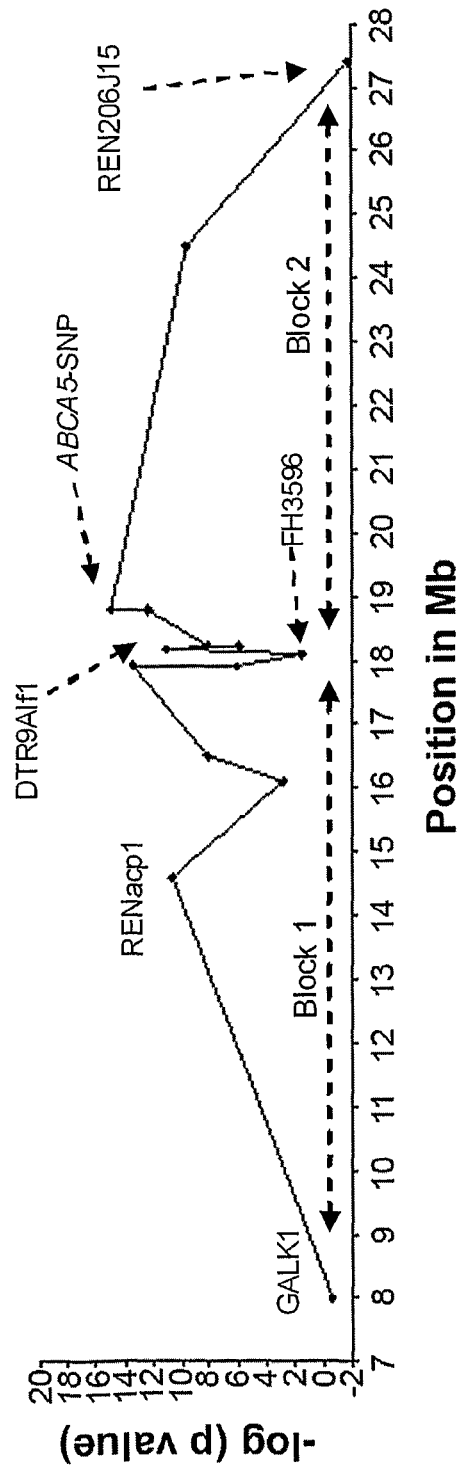

FIG. 3 shows the fine mapping of the NCL of the French AST. Significance of association was calculated with the STRAT software for markers within the CFA09 critical region (Bonferroni corrected pvalues; significance when— log(pvalue)≧3). The candidate region spans 19.3 Mb between markers GALK1 and REN206J15 and can be divided into two large blocks of markers. Block 1 spans 10 Mb between markers GALK1 and FH3596 while block 2 spans 9.3 Mb between markers FH3596 and REN206J15.

Figure 4:
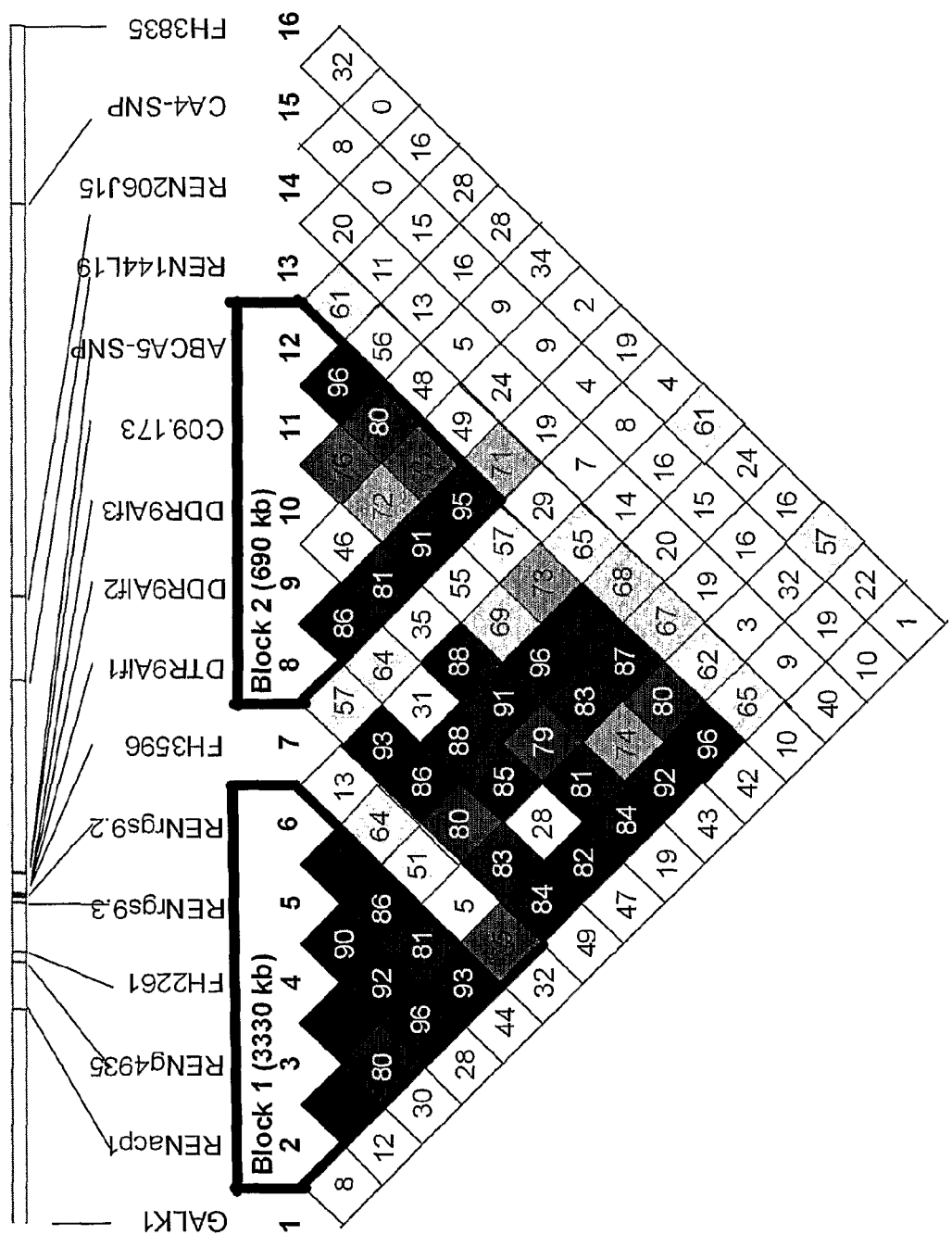

FIG. 4 shows the two blocks of markers defined by the two-point linkage disequilibrium (LD) analysis between 16 markers from CFA09 in French ASTs. Linkage disequilibrium (in LD score×100) between CFA09 markers is indicated in each square. A square with no value indicates a linkage of 100% between two markers: The position of each marker is indicated above its name. Analyses were performed with HAPLOVIEW software. The two blocks of markers defined by the fine mapping (FIG. 3) could be restricted to two haplotypic regions spanning 3.3 Mb for block 1 and 690 kb for block 2.

Figure 5:
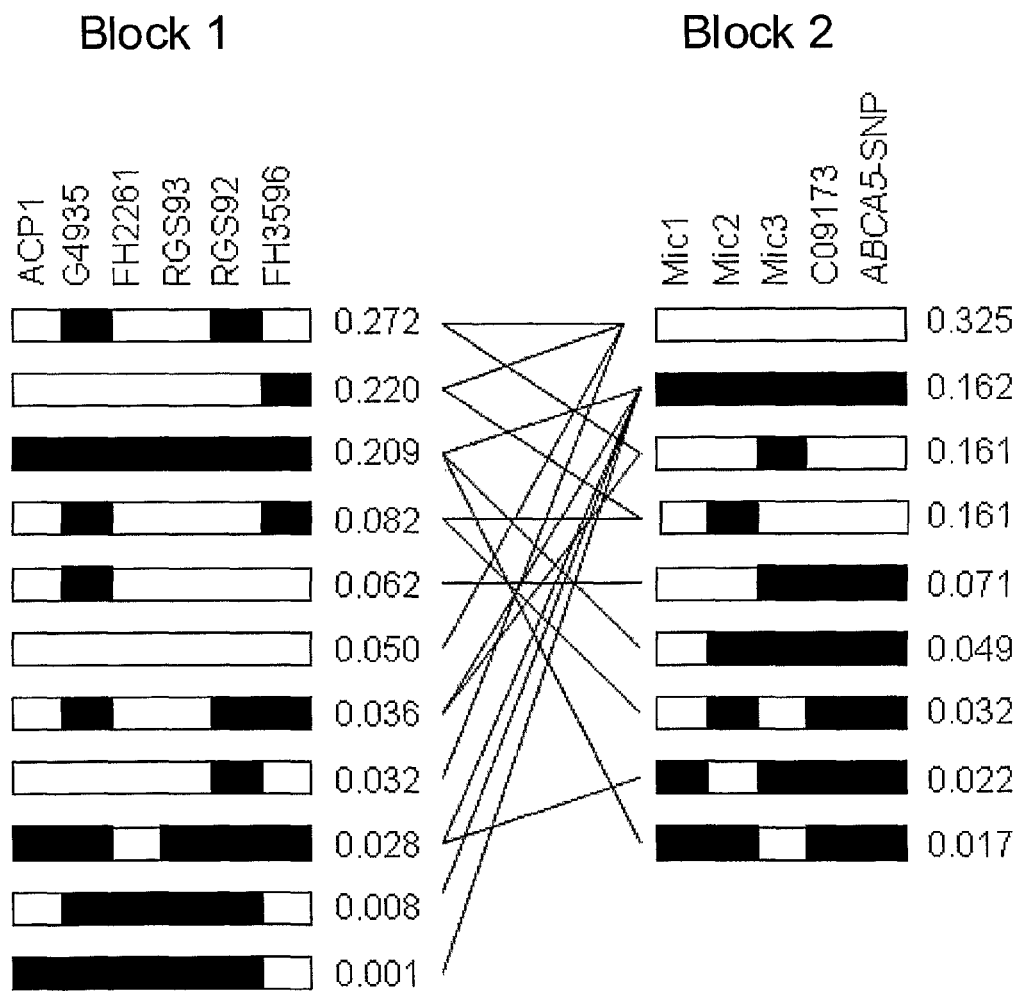
Figure 6:
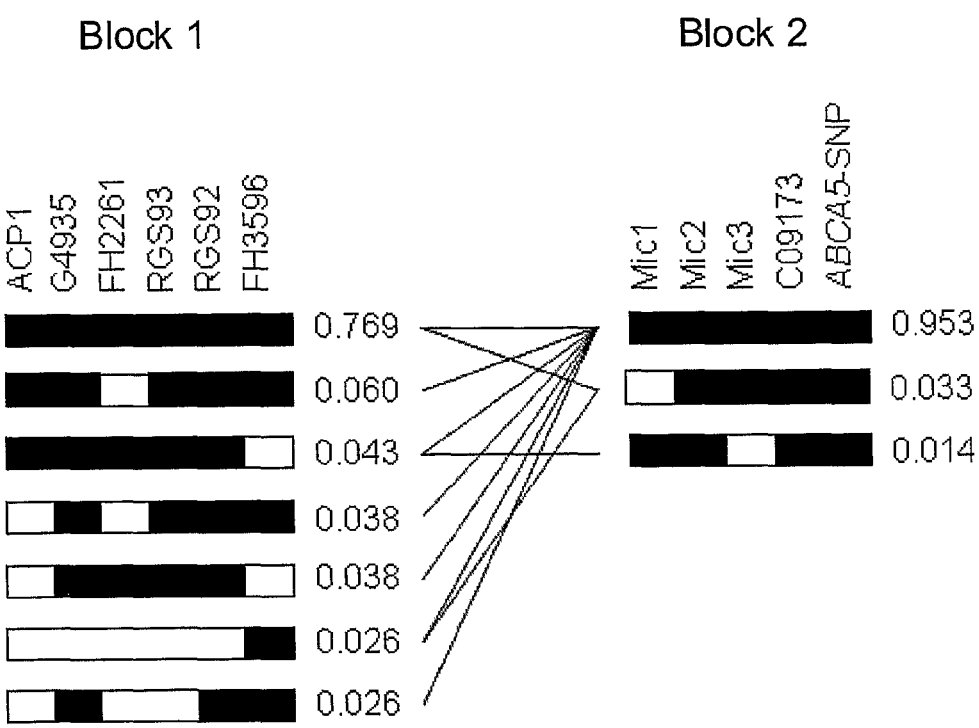

FIGS. 5 and 6 show the strong genotype-phenotype correlation of NCL to Block 1 and Block 2 haplotype. The disease AST allele is shown in black and the alternative allele in white. Frequency, indicated right to each haplotype, was calculated with HAPLOVIEW using the genotypes of the 77 French ASTs.

Figure 7:
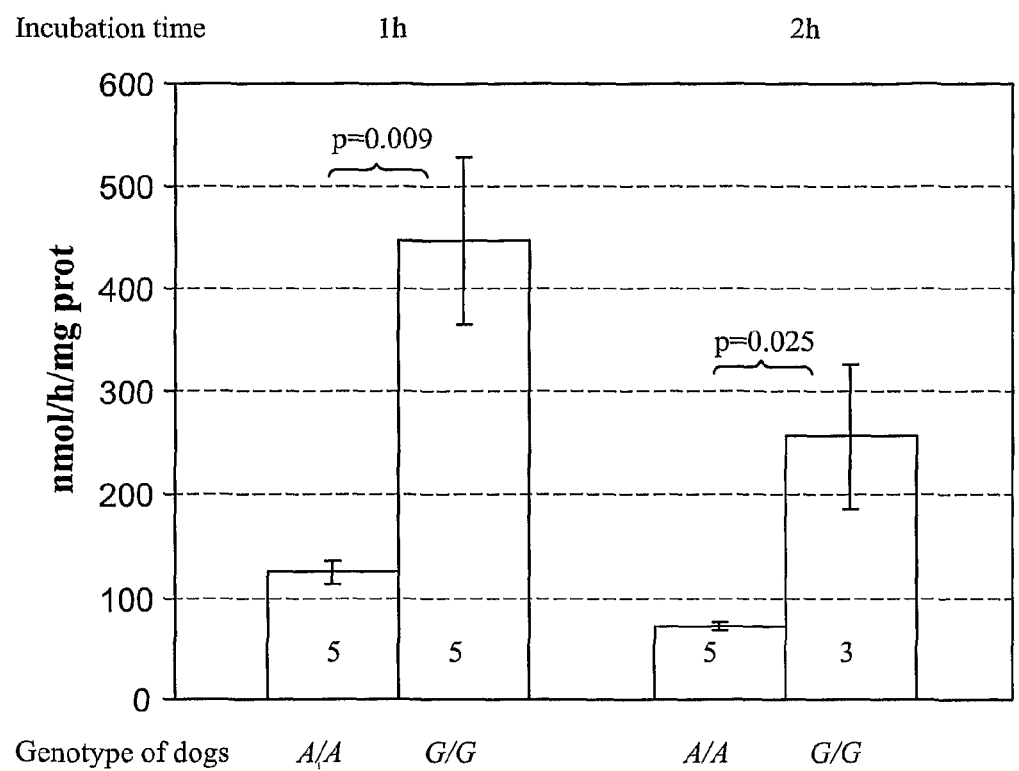

FIG. 7 shows histograms displaying the arylsulfatase activity (in nmol/h/mg of protein) measured after 1 (1h) or 2 hours (2h) of incubation with the substrate in homozygous affected (A/A) and healthy control (G/G) French ASTs. The number of dogs analyzed is given within each histogram and vertical bars represent the standard error of the mean, Mann-Whitney-Wilcoxon pvalues are indicated above the columns.

EXAMPLE

This example describes the identification of the genetic variation responsible for hereditary cerebellar ataxia or hereditary cerebellar cortical degeneration in ASTs.

Materials and methods

Dogs

A total of 104 affected dogs were included in this study. Seventy affected dogs were diagnosed by European or American board-certified Veterinary neurologists at the Alfort School or Lyon School of Veterinary Medicine, France and at the NC College of Veterinary Medicine, Raleigh, N.C., USA. For each dog, clinical history was collected and a complete clinical and neurological evaluation was performed. Routine hematology and serum biochemistry parameters were assessed. With owner consent, the dogs were anesthetized and the cerebrospinal fluid was sampled from the cerebello-medullary citern and routine analysis was performed. Brain examination was carried out using magnetic resonance imaging. Clinical feedbacks were continuously collected. Affected dogs diagnosed by veterinarians in private practice underwent complete physical and neurologic examinations, blood cell count and serum biochemistry. Healthy ASTs were recruited as controls. These healthy dogs were thirty eight≧3-year old French ASTs who followed the complete procedure and failed to exhibit any of the symptoms seen in affected dogs at the time of the initial genome scan. For all these dogs, clinical feedbacks from owners and veterinarians were continuously obtained and allowed the update our clinical database. None of them became affected.

Brain and cerebellum histology

Following their owner's request, 14 dogs aged 4-8 years were euthanized after they had reached the irreversible terminal stage of the disease. The whole brains with cerebellum were removed and weighed. The brains were cut in halves, soaked in 10% buffered formalin for 7 days and embedded in paraffin. Five μm-thick representative sections from midbrain, olfactory bulb, pons, cerebellum, (vermis), frontal lobe, caudate nucleus, basal ganglia, thalamus and occipital lobe were processed and stained with hematoxylin and eosin, Luxol fast blue and Periodic Acid-Schiff Reagent (PAS).

Determination of the mode of inheritance

Pedigrees of affected and healthy dogs were recovered; the number of affected siblings per litter was obtained from their owners. The observed and expected numbers of affected and healthy dogs in the litters were compared using a $\chi^2$ test.

MSS2 and SNP genotyping

DNA was isolated from ethylenediaminetetraacetic acid stabilized blood samples of dogs. PCR amplification of each of the 327 canine microsatellite markers of the Minimal Screening Set 2 (MSS2) (Clark et al. (2004) *Genomics* 84:550-554) was carried out separately on 30 ng of genomic DNA using a classical PCR protocol with AmpliTaqGOLD® DNA polymerase (Applied Biosystems). One μl of each fluorescent PCR product from each chromosome-specific panel was loaded onto a 3130 XL genetic analyser (Applied Biosystems) and resolved with an internal size standard (GeneScan 500 LIZ, PE Biosystems). Results were analysed using GeneMapper software v3.7 (Applied Biosystems).

SNP genotypes were determined using a pyrosequencing method adapted from Ahmandian et al. (2000) *Anal Biochem* 280:103-110, on a Biotage PSQ™ 96 pyrosequencer. PCR primers for the ABCA5-SNP were 5'-biotinyl-TTCCATC-CCTTTCACAGTCTTT-3' (SEQ ID NO: 3) with 5'ACGATGGTTTTCAAATCTTACCT-3' (SEQ ID NO: 4); and, the sequencing primer was 5'-GTTTTCAAATCTTAC-CTTCT-3' (SEQ ID NO: 5). PCR primers for the ARSG-SNP were 5'-biotinyl-CTCCTGGCCTGGCTTTCTGT-3' (SEQ ID NO: 6) with 5'ATCCCCGTGACGTAGCCG-3' (SEQ ID NO: 7); and, the sequencing primer was 5'TTGTGCGT-GACTCCG-3' (SEQ ID NO: 8). PCR primers for the CA4-SNP were 5'-CTCTTCTTTCGGGTGGACCT-3' (SEQ ID NO: 9) with 5'-biotynyl-CAGCAGACAGTAGGGAAACT-GAT-3' (SEQ ID NO: 10); and, the sequencing primer was 5'-GGAAGTGGTTCTTTGC-3' (SEQ ID NO: 11).

Association study

For genome-wide mapping, the inventors performed a case control association analysis. In a first step, genotypes at MSS2 loci were analysed using STRAT software. The p-values were corrected for the number of comparisons according to Bonferroni procedures. In a second step, fine mapping of the CFA09 critical region was performed using PLINK software. Individuals were tested for both a phenotype and a genotype at each locus. It was assumed that both genotype and phenotype were binary, denoting the alleles by A and non-A. A-class allele was defined as the disease associated allele (most frequent allele in the affected dog cohort). Multiallelic loci were accommodated by focusing on the A allele and grouping the remaining as non-A allele. The p-values were corrected for the number of comparisons according to Bonferroni procedures. Linkage disequilibrium analysis was performed using PLINK software and, finally, the disease associated haplotypes were identified using Haploview software (Purcell et al. (2007) *Am. J. Hum. Genet.* 81:559-575).

RT-PCR

A collection of organ samples (in particular from brain, muscle (biceps femoris), gut, liver, lung, oesophagus, kidney, pancreas, aorta, diaphragm and ovary) were collected and frozen. They were obtained from two dogs who were euthanized for medical reasons, namely a 7 year-old affected AST and a 4 year-old Labrador Retriever suffering from a non-neurological incurable disease. Also, biopsies of a biceps femoris and a lymph node from a living 5 year-old healthy AST were obtained under anesthesia. Poly(A)$^+$ RNA were extracted using the Ambion Poly(A)Purist MAG kit (Ambion). One hundred ng of Poly(A)$^+$mRNA were reverse-transcribed using the SuperScript III RT kit (Invitrogen). The cDNA were then amplified using the Q-Bio Taq DNA Polymerase (Qbiogen) and the primers listed in Table 1. PCR products were analysed by electrophoresis on a 1.5% agarose gel.

TABLE 1

Primers used for RT-PCR expression profiles of candidate genes

| Gene | RT-PCR oligonucleotides (forward and reverse) | Localization | Annealing temperature (° C.) | Product size (bp) |
|---|---|---|---|---|
| AMZ2 | 5'-CAAACAGTACGGCACTCTGAA-3' (SEQ ID NO: 12) | exon 1 | 56 | 1116 |
|  | 5'-GTGCAAGTGTTTATTTCAATAACTATG-3' (SEQ ID NO: 13) | exon 6 |  |  |
| SLC16A6 | 5'-TTTGTTCCAGAGCCAATGTTT-3' (SEQ ID NO: 14) | exon 1 | 56 | 1166 |
|  | 5'-GAAGGCTCGGCTGTAAATCTT-3' (SEQ ID NO: 15) | exon 6 |  |  |
| ARSG | 5'-GTTCCTGGGGGTGACTTTCT-3' (SEQ ID NO: 16) | exon 8 | 58 | 400 |
|  | 5'-ATCTGCCTGTGGGGAAATC-3' (SEQ ID NO: 17) | exon 11 |  |  |
| WIPI1 | 5'-GCTTCTCCTTCAACCAGGACT-3' (SEQ ID NO: 18) | exon 1 | 62 | 593 |
|  | 5'-TACAGAGAACACCCGGATGAC-3' (SEQ ID NO: 19) | exon 7 |  |  |
| FAM20A | 5'-CAAAGAGCAGCTCAACCTCAC-3' (SEQ ID NO: 20) | exon 1 | 60 | 687 |
|  | 5'-TCTTTTCCTGCCAGCGAGTA-3' (SEQ ID NO: 21) | exon 6 |  |  |
| ABCA8 | 5'-GTCAACAGACCTGGGCATTA-3' (SEQ ID NO: 22) | exon 1 | 58 | 395 |
|  | 5'-CGTGAACTTCAAATGATATGAGAATG-3' (SEQ ID NO: 23) | exon 3 |  |  |
| ABCA9 | 5'-GCACATAAGTGTCGGTCAGC-3' (SEQ ID NO: 24) | exon 1 | 58 | 378 |
|  | 5'-AAGAGGACTTTCACTGCATCTACA-3' (SEQ ID NO: 25) | exon 3 |  |  |
| ABCA6 | 5'-AAACTCAAGCACTTCTGTGCAA-3' (SEQ ID NO: 26) | exon 1 | 58 | 360 |
|  | 5'-TGTCATGAAAGATGATTCCAATG-3' (SEQ ID NO: 27) | exon 3 |  |  |
| ABCA5 | 5'-GGAGTTTTTAAAGATAATGGGACTTCA-3' (SEQ ID NO: 28) | exon 5 | 60 | 501 |
|  | 5'-TAGACGGCCAAGAGGACATAGAA-3' (SEQ ID NO: 29) | exon 8 |  |  |

TABLE 1-continued

Primers used for RT-PCR expression profiles of candidate genes

| Gene | RT-PCR oligonucleotides (forward and reverse) | Localization | Annealing temperature (° C.) | Product size (bp) |
|---|---|---|---|---|
| KCNJI2 | 5'-CTCTCCTGGCTGTTCTTTGG-3' (SEQ ID NO: 30)<br>5'-AAGTGGCTCTTCCGAAGGTT-3' (SEQ ID NO: 31) | exon 1<br>exon 1 | 60 | 386 |

Statistical analysis

Chi-square test ($\chi^2$) and non parametric Mann-Whitney-Wilcoxon test for small distributions were performed with StatView F-4.1 software (Abacus Concepts).

Enzymatic assays

ARSG activity towards p-nitrocatechol sulphate was assayed in leucocytes according to Frese et al. (2008) *J. Biol. Chem.* 283:11388-11395.

Results

Clinical and histopathological characterization of the disease

American Staffordshire Terriers (ASTs) suffering from locomotor ataxia are weekly seen in specialized pet medical centers. A cohort of 54 males and 50 females exhibiting locomotion disablements were analyzed in France (n=66) and the USA (n=38). Seventy dogs were directly evaluated by board-certified neurologists from a French School of Veterinary Medicine or the College of Veterinary Medicine, North Carolina State University and 14 who had been initially diagnosed by their regular veterinarian were confirmed by one of the inventors. They were mainly from France and the USA, with the exception of 3 dogs living in Belgium and one in Germany. The 66 identified affected French ASTs included 36 males and 30 females. Fifty-two were evaluated by a board-certified neurologist or an internist at Alfort; one was evaluated at the School of Veterinary Medicine in Lyon (France). Fourteen dogs were evaluated by their regular veterinarian and details of the findings were evaluated by the inventors. One of these 14 dogs was directly related (sibling) to an individual with confirmed disease. For 5 dogs, no pedigree information was available. Four dogs were not registered as ASTs in the pedigrees from the French Canine Association (Société Centrale Canine).

To test affected dogs against cerebellar cortical degeneration it was proposed to their owners a magnetic resonance imaging (MRI). Among the 54 dogs for which owners agreed to MRI examination, 53 exhibited significant cerebellar atrophy or enlarged cerebellar sulci. Interestingly, these features were not observed in one 4 year-old dog examined in the very early steps of the observed locomotor problems. Owners noticed the first neurologic signs manifested by their dogs when aged between 18 months and 8 years (between 21 months and 7 years for the French ASTs group). The majority of affected ASTs (70% [72% in the French ASTs group]) begun to show ataxia between 3 and 5 years of age. The first clinical signs of the disease included stumbling when negotiating stairs, walking uphill or downhill or turning corners. Later, the affected dogs developed ataxia with hypermetria and coarse intention tremor. They had difficulty in initiating movements and fall when shaking the head. When rolled onto their backs, dogs showed vertical, horizontal or rotary nystragmus. Mentation and behaviour remained normal. The affected ASTs were euthanized between 3 months and more than 9 years after they have been diagnosed. One affected AST, born in January 1999 was still alive in June 2008.

Post-mortem examination was performed on three 6, 7 and 8 year-old affected males and two 4 and 6 year-old affected females. Representative sections from several brain areas were prepared and stained with HE, Luxol Fast Blue and PAS. Luxol fast blue was used for staining of myelin and myelinated axons. PAS staining was used to identify carbohydrates like cerebrosides or glycogen in brain sections. At necropsy, affected ASTs had cerebellum atrophy and inconsistent unilateral enlargement of lateral ventricles. The most prominent histological finding seen in each of them was a marked loss of Purkinje cells in all areas of the cerebellum. Dystrophic neurones were observed in the center of the granular layer. Massive accumulation of lipofuscin pigments in neurones and macrophages of the cerebellum and cerebral cortex was observed in each of them. Remaining Purkinje cells had a massive accumulation of pigments. Such an accumulation was also noticed in neurones of the hypoglossal nucleus and motor ocular nerves, in pyramidal cells of hippocampus, and in occipital cortex and pyramidal cells of horn of Ammon. The most prominent accumulation was observed in thalamic neurones of posterior nuclei and pulvinar. Storage material appeared blue on HE-stained sections, pink on PAS-stained sections and blue-green on Luxol-Fast-Blue-stained sections. It was made of multiple granules that swelled and distorted the cells and displaced the nuclei and Nissl substance to the periphery of the cells. Storage material was observed in the cytoplasmic arms of axons and in macrophages located where Purkinje cells had disappeared. White matter appeared histologically normal in each necropsied dogs. The inventors concluded from these histopathological features that the locomotor ataxia frequently seen in AST is highly reminiscent of a storage disease called "Neuronal Ceroid Lipofuscinose" or "Neuronal Ceroid Lipofuscinosis" (NCL).

Inheritance

Pedigrees were recovered for 84 dogs. Dogs of both sexes were affected. The ratio of affected males (36) to females (30) was 1.2 to 1. In 2 litters, at least 2 littermates were affected. In 3 litters, at least 3 littermates were affected. Lastly, in 2 litters, 4 littermates were affected. In 4 families, one parent and at least one offspring were affected. The pedigrees of 73 dogs for which the inventors had full information concerning the status of the littermates of the propositus, were used to assess the mode of inheritance. Data are presented in Table 2.

TABLE 2

Numbers of affected and healthy dogs in AST litters
Minus one affected dog present per litter

| | Affected | | Healthy | |
|---|---|---|---|---|
| Parents | Observed | Expected | Observed | Expected |
| 2 healthy parents | 7 | 4.5 | 11 | 13.5 |
| Chi Square test | $\chi^2$ = 1.18 no statistical difference | | | |

TABLE 2-continued

Numbers of affected and healthy dogs in AST litters
Minus one affected dog present per litter

|  | Affected | | Healthy | |
|---|---|---|---|---|
| Parents | Observed | Expected | Observed | Expected |
| 1 affected parent | 12 | 13 | 14 | 13 |
| Chi Square test | $\chi^2 = 0.154$ no statistical difference | | | |
|  | No affected dogs in litters | | | |
| 1 affected parent | 27/27 healthy dogs in a total of 4 litters | | | |

Assuming an autosomal recessive mode of inheritance, no statistical difference was seen between the expected and the observed numbers of affected and healthy dogs for the two types of litters available (two healthy parents and one affected parent). Two litters of 8 healthy dogs each, 1 litter of 6 healthy dogs and 1 litter of 5 healthy dogs were born from couples of dogs including one affected parent. These data are in complete agreement with those of Olby et al. (2004) *J. Vet. Intern. Med.* 18:201-208, who analysed 37 relative dogs. A posteriori analysis of the complete panel of affected dogs (France, n=66 and US, n=35) showed that the clinical phenotype had a 22.8% penetrance at 3 years, 78.2% at 5 years and 100% at 8 years of age. In particular, penetrance was complete at 7 years of age in French ASTs and reduced to 78% and 24% at 5 and 3 years of age respectively, while in US bred ASTs penetrance was complete at 9 years of age (Olby et al., 2004). Expressivity of the disease was very variable, dogs been euthanized, while they became totally unable to walk without falling repeatedly, between a few month to more than 9 years after they have been diagnosed. One affected dog, diagnosed at 2 years of age, was 9 years of age and still alive in June 2008. But most ataxic ASTs survived for 2 to 4 years before they were euthanized.

The inventors therefore conducted mapping analyses by postulating an autosomal recessive mode of inheritance with complete penetrance in dogs aged more than 9 years and reduced penetrance in dogs less than 9 years of age and with variable expressivity. Finally, dogs from both sexes were affected and their relative number was not significantly different (males: n=54; females: n=50; $\chi^2$ =0.15), thus showing an identical penetrance in both genders.

Mapping of the morbidity locus on CFA09 by association study

A total of 77 French ASTs were recruited for a whole genome study: 39 (22 males, 17 females) exhibited clear signs of NCL while 38 (22 males, 16 females) were healthy. All healthy dogs were older than 3 years when recruited. The 77 ASTs were not related excepted for 2 affected siblings, 2 affected half-siblings, an affected mother and its healthy daughter and a healthy mother and its 3 healthy pups. The inventors therefore chose to perform a case-control study. Two hundred forty-seven autosomal microsatellites markers were selected from the MSS2 panel (Clark et al. (2004) *Genomics* 84:550-554) on two criteria: (i) their polymorphism in various breeds of dogs and (ii) the amplification accuracy under standard PCR conditions. The 77 ASTs were genotyped for the 247 markers. Two hundred thirty-one markers showed correct PCR amplification and were polymorphic in the case patients and control subjects. The coverage of the genome was 9.85 Mb. To determine if any of the markers were associated with the clinical signs of NCL, the inventors performed a case-control test using the program STRAT. This analysis revealed strong association between the clinical signs of the disease and C09.173 marker on canine chromosome 9 (CFA09) ($\chi^2$ test, Bonferroni corrected p-value =$4.10 \times 10^{-13}$) (FIG. 1). The inventors concluded that NCL locus was located on CFA09.

Limiting the critical interval by fine mapping and haplotype analysis

Because of the linkage of NCL locus with C09.173 marker, the inventors selected 17 additional CFA09 markers, either microsatellites or SNPs. Several of these markers were from the NCBI dog database, while others were identified in the inventors' laboratory (Table 3).

TABLE 3

Additional CFA09 markers tested for the whole genome scan
Microsatellites forward primers were 5'end labeled with
6-carboxyfluorescein (6-FAM). Annealing temperature
was a 61-51° C. touch down.

| Marker name | Primers (forward and reverse) | Product size (bp) | Position from centromere (Mb) | Polymorphism in AST dogs |
|---|---|---|---|---|
| ACP1 (RENacp1) | 5'-6-FAM-ACCCCTGTGCACCTCATCACTTA-3' (SEQ ID NO: 32) 5'-AGGTCACTGTCTGTACACGTAGTG-3' (SEQ ID NO: 33) | 86 | 14.63 | yes |
| G4935 (RENg4935) | 5'-6-FAM-ACATCAGGTGAAGAGCTTGC-3' (SEQ ID NO: 34) 5'-GAAGTTGGCTGGGGAAGG-3' (SEQ ID NO: 35) | 242 | 16.12 | yes |
| RGS93 (RENrgs9.3) | 5'-6-FAM-AGTTAGACTGCCTTCTGATGAAGTG-3' (SEQ ID NO: 36) 5'-6-FAM-TGTCTATCGATTCTTCCCAACTAAC-3' (SEQ ID NO: 37) | 151 | 17.94 | yes |

TABLE 3-continued

Additional CFA09 markers tested for the whole genome scan Microsatellites forward primers were 5'end labeled with 6-carboxyfluorescein (6-FAM). Annealing temperature was a 61-51° C. touch down.

| Marker name | Primers (forward and reverse) | Product size (bp) | Position from centromere (Mb) | Polymorphism in AST dogs |
|---|---|---|---|---|
| RGS92 (RENrgs9.2) | 5'-6-FAM-GCACGACTCCAGGAATATAGTAGAA-3' (SEQ ID NO: 38) 5'-TGGGACTTAAACGCTAAATTGTATG-3' (SEQ ID NO: 39) | 171 | 17.96 | yes |
| Ren198p23 | 5'-6-FAM-TTGTACATTATCTGTTCTACCTCGG-3' (SEQ ID NO: 40) 5'-TCTTCAGCAGGCCTTTTCTC-3' (SEQ ID NO: 41) | 132 | 18.09 | yes |
| FH3596 | 5'-6-FAM-ACATCAGGTGAAGAGCTTGC-3' (SEQ ID NO: 42) 5'-GAAGTTGGCTGGGGAAGG-3' (SEQ ID NO: 43) | 285 | 18.11 | yes |
| Mic1 (DTR9A1f1) | 5'-6-FAM-TTCCAGGGGCACTTTCTACTT-3' (SEQ ID NO: 44) 5'-TCTCCCTCTGCCTATGTCTCA-3' (SEQ ID NO: 45) | 191 | 18.18 | yes |
| Mic2 (DDR9A1f2) | 5'-6-FAM-GGGCGTTGAACAGATCAAATA-3' (SEQ ID NO: 46) 5'-TCATCTCCACACCAGGAGACT-3' (SEQ ID NO: 47) | 235 | 18.23 | yes |
| Mic3 (DDR9A1f3) | 5'-6-FAM-GGGCTCTGAGTCTGGTCTTTT-3' (SEQ ID NO: 48) 5'-ACGTATGTGCGTATCCCGTAT-3' (SEQ ID NO: 49) | 173 | 18.24 | yes |
| ABCA5-SNP | 5'-biotinyl-TTCCATCCCTTTCACAGTCTTT-3' (SEQ ID NO: 50) 5'-ACGATGGTTTTCAAATCTTACCT-3' (SEQ ID NO: 51) | 60 | 18.84 | yes |
| KCNJ2 | 5'-6-FAM-TATCTGGCGAATGAGATCCTCT-3' (SEQ ID NO: 52) 5'-CGTTTTCGTAGCAAAAGGAGTT-3' (SEQ ID NO: 53) | 193 | 19.60 | no |
| FH1014 | 5'-6-FAM-AGGCTATTAACCCCTGATCG-3' (SEQ ID NO: 54) 5'-CGATGCCTTACTTAAACAAACC-3' (SEQ ID NO: 55) | 245 | 22.87 | no |
| Ren144119 | 5'-6-FAM-TGTCATCCTGCATCCAATGT-3' (SEQ ID NO: 56) 5'-CAATTTACTTTTGGGCGTCA-3' (SEQ ID NO: 57) | 216 | 24.83 | yes |

TABLE 3-continued

Additional CFA09 markers tested for the whole genome scan Microsatellites forward primers were 5'end labeled with 6-carboxyfluorescein (6-FAM). Annealing temperature was a 61-51° C. touch down.

| Marker name | Primers (forward and reverse) | Product size (bp) | Position from centromere (Mb) | Polymorphism in AST dogs |
|---|---|---|---|---|
| Zubeca 3 | 5'-6-FAM-TCAGGCCTTTGATGATTTCA-3' (SEQ ID N: 58) 5'-CAGGGCTGGCATTTATGTAAG-3' (SEQ ID NO: 59) | 201 | 26.16 | no |
| Ren206j15 | 5'-6-FAM-CCCCCAACAATCAAATGTTTA-3' (SEQ ID NO: 60) 5'-AATGCAGCTATATGGGCCAC-3' (SEQ ID NO: 61) | 227 | 27.45 | yes |
| FH4059 | 5'-6-FAM-GGATCTGTGTTTCTTCGTTAGC-3' (SEQ ID NO: 62) 5'-TTGATTAAAGAGCAGCTTAGCC-3' (SEQ ID NO: 63) | 396 | 30.54 | yes |
| CA4-SNP | 5'-CTCTTCTTTCGGGTGGACCT-3' (SEQ ID NO: 64) 5'-biotynyl-CAGCAGACAGTAGGGAAACTGAT-3' (SEQ ID NO: 65) | 79 | 39.65 | yes |

These markers span a 25 Mb chromosomal region around C09.173. Fourteen of them were polymorphic in the studied dogs. The additional markers allowed to confirm the mapping of NCL locus onto canine chromosome 9 (FIG. 2). Interestingly, the strongest association was obtained for ABCA5-SNP, a synonymous SNP located within exon 36 of the ABCA5 gene (GeneBank ID: FM211813; $\chi^2$ test, Bonferroni corrected p-value=$1.10 \times 10^{-15}$). Furthermore, these markers narrowed the critical interval to a 19.30 Mb chromosomal segment extending from GALK1 ($\chi^2$ test, Bonferroni corrected p-value=3.40) to REN206J15 ($\chi^2$ test, Bonferroni corrected p-value=56.85) which could be divided into two regions of homozygosity (10 Mb and 9.3 Mb) interrupted by a region of 1 Mb. Block 1 covered the sequence between GALK1 and FH3596 ($\chi^2$ test, Bonferroni corrected p-value=0.026) and block 2 covered the sequence between FH3595 and REN206J15 (FIG. 3).

Using the HAPLOVIEW program, the inventors showed that these two blocks were in linkage disequilibrium on CFA09 and haplotype analysis revealed a 4.21 Mb region (14.63-18.84 Mb) that included two distinct narrowed blocks with perfect genotype-phenotype correlation (FIG. 4). Each of these two narrowed blocks included 5 markers (first narrowed block of 3.33 Mb [RENacpl—RGS92]; second narrowed block of 690 kb [DTR9A1f1—ABCA5-SNP]). The haplotype of the first narrowed block was present in 76.9% of affected AST and in 20.9% of healthy controls while the haplotype of the second narrowed block was present in 95.3% of affected AST and in 16.2% of healthy controls (FIG. 5, FIG. 6). From these data, the inventors concluded that the NCL causing gene location was located in the narrowed block 2 and more particularly in the vicinity of the ABCA5-SNP position.

Candidate gene selection

To search for candidate genes that could account for NCL in dogs, the inventors took advantage of the available annotation of the Dog genome. The 690 kb region contained 8 genes and 3 non annotated transcriptional units and the inventors included 5 additional genes from the flanking ends of the region. From the centromeric to the telomeric part of the region of interest, the 16 candidate genes were AA/22 (archaelysin family metallopeptidase 2), SLCA16A6 (solute carrier family 16, member 6), ARSG (arysulfatase G), WIP11 (WD repeat domain, phosphoinositide interacting 1), PRKARIA (protein kinase, cAMP-dependent, regulatory, type I, alpha), FAM20A (family with sequence similarity 20, member A), LOC610988, LOC610995, ABCA8 (ATP-binding cassette, sub family A, member 8), U6, ABCA9 (ATP-binding cassette, sub family A, member 9), ABCA6 (ATP-binding cassette, sub family A, member 6), ABCA5 (ATP-binding cassette, sub family A, member 5), MAP2K6 (mitogen-activated protein kinase kinase 6), KCNJ16 (potassium inwardly-rectifying channel, subfamily J, member 16) and KCNJ2 (potassium inwardly-rectifying channel, subfamily J, member 2). Each candidate gene was considered for its expression levels in mouse and human tissues, its molecular functions, its participation to biological processes and pathway, and lastly its expression in dog tissues. Their molecular function in biological processes and pathways were obtained from the Panther classification system and GeneCards database (Table 4). From the Gene Expression Atlas database (SymAtlas alias, Genomics Institute of the Novartis Research Foundation), all annotated genes but KCNJ16 seem ubiquitously expressed in human and mouse tissues and using a panel of ~10 organs collected from a 4 year-old female Labrador Retriever (brain, skeletal muscle, heart, gut, liver, lung, esophagus, kidney, pancreas, skin and ovary), the inventors confirmed that the 13 annotated genes are also ubiquitously expressed in canine tissues, with the exceptions of ABCA8 and ABCA9 that could not be detected in kidneys (Table 4).

TABLE 4

Candidate genes in the critical region

| Position in Mb | Gene | Name | Function | Expression in Human and Mouse | Expression in Dog |
|---|---|---|---|---|---|
| 18.12 | AMZ2 | Archaelysin family metallopeptidase 2 | Metallopeptidase | Ubiquitous | Ubiquitous |
| 18.14 | SLC16A6 | Solute carrier family 16, member 6 | Monocarboxylic acid transporter | Ubiquitous | Ubiquitous |
| 18.18 | ARSG | Arylsulfatase G | Sulphatase activity. Lysosomal enzyme | Ubiquitous | Ubiquitous |
| 18.24 | WIPI1 | WD repeat domain, phosphoinositide interacting 1 | WD40 repeat protein of 49 kDa interacting with phosphoinositides | Ubiquitous, high expression in heart | Ubiquitous |
| 18.31 | PRKAR1A | Protein kinase, cAMP-dependent, regulatory, type I, alpha (tissue-specific extinguisher 1) | Protein kinase. Tumor-suppressor gene. When mutated in humans PRKAR1A is responsible for the Carney complex. | Ubiquitous | Ubiquitous |
| 18.33 | FAM20A | Family with sequence similarity 20, member A | Murine FAM20A is a secreted protein expressed in hematopoietic cells | Ubiquitous | Ubiquitous |
| 18.43 | LOC610988 | Similar to 60S ribosomal protein L23a | Hypothetical ribosomal protein | Unknown | Not tested |
| 18.44 | LOC610995 | None | Unknown | Unknown | Not tested |
| 18.55 | ABCA8 | ATP-binding cassette, sub-family A (ABC1), member 8 | ABC transporter | Ubiquitous, high expression in olfactory bulb (Human) and liver (Mouse). | Ubiquitous except kidney |
| 18.57 | U6 | U6 spliceosomal RNA | Hypothetical spliceosomal RNA | Unknown | Not tested |
| 18.64 | ABCA9 | ATP-binding cassette, sub-family A (ABC1), member 9 | ABC transporter | Ubiquitous | Ubiquitous except kidney |
| 18.72 | ABCA6 | ATP-binding cassette, sub-family A (ABC1), member 6 | ABC transporter | Ubiquitous | Ubiquitous |
| 18.85 | ABCA5 | ATP-binding cassette, sub-family A (ABC1), member 5 | ABC transporter | Ubiquitous | Ubiquitous |
| 18.97 | MAP2K6 | Mitogen-activated protein kinase kinase 6 | Protein kinase. Activates p38 MAP kinase. | Ubiquitous | Ubiquitous |
| 19.57 | KCNJ16 | Potassium inwardly-rectifying channel, subfamily J, member 16 | Ion channel | Thyroid, kidney and pancreas | Ubiquitous |
| 19.60 | KCNJ2 | Potassium inwardly-rectifying channel, subfamily J, member 2 | Ion channel | Ubiquitous, high expression in whole blood in Human | Ubiquitous |

Semi-quantitative expression levels were also assessed by the inventors in a panel of tissues from a 7 year-old affected AST and no difference could be observed for any of them (data not shown). Using genomic DNA from 4 healthy and 4 affected AST, the inventors therefore decided to batch sequence and compare in the 2 groups of dogs the coding and intron-exon boundaries sequences of those genes primarily suspected to play a role in neuronal homeostasis.

They found no difference for KCNJ2, MAP2K6 and SLC16A6. One synonymous SNP was detected in the single exon of KCNJ16 [Genebank ID: FM211814] and was not associated with the disease. In addition to the previously described synonymous SNP in exon 36 of the ABCA5 (ABCA5-SNP) highly associated with the NCL locus, 2 non synonymous SNPs were detected in exons 14 and 17 [Genebank ID: FM211419 and FM211812] and were not linked to the disease. Finally, a single non-synonymous (G/A) SNP was detected in the exon 2 of the ARSG gene and in this panel of 8 dogs, specifically segregated with NCL. The inventors therefore tested the strength of its association with NCL using a larger group of dogs.

ARSG polymorphism in affected dogs

A large panel of dogs was thus genotyped for the SNP identified in the ARSG gene. First, 71 French healthy control ASTs and the 66 French and 38 US affected dogs allowed to confirm that the allele segregation of the SNP was compatible with the autosomal recessive inheritance of NCL. Indeed, 100% of affected dogs were A/A, all healthy ASTs were G/G or G/A, and only one clinically healthy dog was A/A (Table 5). Importantly, this dog shares a 2.77 Mb haplotype

[RENg4935 - ABCA5-SNP] with affected ASTs. He was born in September 2000 and because the owner did not give his consent, could not be MRI-assessed. His clinical status is continuously investigated by the inventors. The panel also included 525 non-NCL dogs from 9 putatively AST- related breeds, 132 dogs from additional 45 breeds and 3 French mongrels. None of the 1320 genotyped chromosomes contained the A allele which seemed therefore specific of the AST breed and more precisely associated with the NCL predisposition (Table 5).

TABLE 5

Genotypes for the ARSG-SNP a-Genotype frequencies for the ARSG-SNP in the healthy and affected ASTs groups.

| Clinical status of dogs | Healthy | | | Affected | | |
|---|---|---|---|---|---|---|
| Genotype at the ARSG-SNP locus | G/G | G/A | A/A | G/G | G/A | A/A |
| French American Staffordshire Terrier | 53.5% (n = 38) | 45.1% (n = 32) | 1.4% (n = 1) | 0 | 0 | 100% (n = 66) |
| US American Staffordshire Terrier | ND | ND | ND | 0 | 0 | 100 (n = 38) | b-Panel of Bulls and Terriers dogs potentially related to the AST breed and AST non related dogs with a confirmed G/G genotype.

| Breed | Number of dogs |
|---|---|
| Staffordshire Bull Terrier | 22 |
| American Bulldog | 18 |
| Bull Terrier | 139 |
| Bull Terrier Toy | 33 |
| Bullmastiff | 23 |
| Mastiff | 31 |
| English Bulldog | 82 |
| Dogo Argentino | 18 |
| German Boxer | 159 |
| American Cocker Spaniel | 2 |
| Australian Cattle Dog | 3 |
| Barzoi | 5 |
| Beagle | 5 |
| Beauceron | 2 |
| Belgian Shepherd Dog | 6 |
| Bernese Mountain Dog | 3 |
| Bichon | 1 |
| Bordeaux Dogge | 1 |
| Brittany Spaniel | 2 |
| Chow-Chow | 2 |
| Collie | 1 |
| Coton de Tulear | 2 |
| Dalmatien | 5 |
| Das chund | 5 |
| Drahthaar | 1 |
| English Cocker Spaniel | 2 |
| English Setter | 2 |
| Fox Terrier | 4 |
| French Bulldog | 4 |
| German Shepherd dog | 7 |
| German Short-haired Pointing Dog | 2 |

TABLE 5-continued

Genotypes for the ARSG-SNP

| Golden Retriever | 7 |
|---|---|
| Great Dane | 2 |
| Husky | 1 |
| Irish Setter | 2 |
| Jack Russell Terrier | 4 |
| Labrador Retriever | 8 |
| Leonberger | 5 |
| Lhassa Apso | 1 |
| Malamute | 1 |
| Newfoundland | 1 |
| Poodle | 5 |
| Pyrenean Mountain Dog | 3 |
| Rottweiler | 5 |
| Saluki | 1 |
| Samoyede | 2 |
| Schnauzer | 1 |
| Shar Pei | 6 |
| Shih Tzu | 2 |
| Tatra Shepherd Dog | 1 |
| Tibet Dogge | 1 |
| Tibetan Terrier | 2 |
| Whippet | 1 |
| Yorkshire Terrier | 3 |
| Mongrel | 3 |

The number of dogs is indicated into brackets.
ND: not determined.
Exhaustive list of Bulls and Terriers dogs potentially related to the AST breed (bolded) and AST non related dogs which have been genotyped for the ARSG SNP. With no exception, these dogs were all G/G.

The ARSG SNP is located at position 296 of the open reading frame and causes the substitution of an histidine for the arginine 99 (Arg99His) in the protein [Genebank ID: FM246885].

To evaluate the functional importance of the Arg99 substitution, the inventors searched whether this residue had been under a positive selective pressure by aligning the sequence of the canine ARSG protein with known metazoan orthologs and with biochemically characterized human ARS family members, namely ARSA, ARSB, ARSC (alias name is STS steroid sulfatase), ARSD, ARSE and ARSF. Global alignments attested that canine and human ARSG are highly conserved (86%), as are canine and murine proteins (79%). In addition, the inventors observed a 100% conservation between the canine ARSG and all the human ARS members for the 10 critical residues known to operate in the catalytic activity of these proteins. Referring to positions in human ARSA (Ghosh (2007) Cell. Mol. Life Sci. 64:2013-2022; Ghosh (2005) Methods Enzymol. 400:273-293), these residues are Asp29, Asp30, HFGS69 (hydroxyformylglycine sulphate 69, the post-translationally modified cysteine 69), Arg73, Lys123, His125, His229, Asp281, Gln282 and Lys303. Although Arg99 (Arg84 refering to human ARSA) was not previously identified as a key component of the catalytic activity, the inventors observed that it is included in a domain of 10 residues displaying a high alignment score between human ARS and ARSG from Dog, Human, Mouse, Chicken, Zebrafish, Fugu, and two species of worms (*Caenorhabditis elegans* and *Ciona intestinalis*). Indeed, 5 of these 10 residues, including Arg99, are conserved. Altogether, these data highly suggested that Arg99 is a critical residue for ARSG activity and that its substitution may impair long-term neuronal survival in AST dogs.

Reduced arylsulfatase activity in affected dogs

In many instances, missense mutations lead to a rapid degradation of the encoded enzyme in the endoplasmic reticulum (Ellgaard et al. (1999) *Science* 286:1882-1888). Before this hypothesis could be directly tested using an antibody and biochemical cellular tests under characterization and because the inventors found the canine ARSG gene ubiquitously expressed, they decided to evaluate the impact of the Arg99His substitution on leucocytes arylsulfatase activity using a method adapted from Frese et al. (Frese et al. (2008) *J. Biol. Chem.* 283:11388-11395). In addition, unwanted compensatory activity by redundant ARS from the family was avoided by the use of pH conditions for STS, ARSF and ARSI (Puca et al. (1997) *Genomics* 42:192-199;, Oshikawa et al. (2009) *Mol. Vis.* 15:482-494) and specific inhibitors for ARSE (warfarin (Franco et al. (1995) Cell 81:1525)), ARSB (chloride ions (Bostick et al. (1978) *Clin. Chem.* 24:1305-1316)). Leucocyte's arylsulfatase activity from 5 A/A homozygous affected ASTs was compared with leucocytes activity of 5 homozygous G/G healthy ASTs, taken as the 100% reference activity level. The inventors observed that after one hour of incubation, the arylsulfatase activity of leucocytes from affected dogs was significantly reduced to 24.7% of the normal activity (Mann-Whitney-Wilcoxon p-values=0.009; FIG. 7) and that after 2 hours of incubation, the activity remained reduced to 28.5% (Mann-Whitney-Wilcoxon p-values=0.025; FIG. 7). Therefore, leucocyte arylsulfatase activity from affected dogs carrying an Arg99His substitution in ARSG could not reach a normal level, strongly suggesting that the GIA mutation detected in the exon 2 of the ARSG gene of American Staffordshire terriers is the disease-causing mutation.

Accordingly, the inventors have demonstrated that the presence of an homozygous A allele in the arylsulfatase G gene of ASTs instead of a G allele is associated with hereditary cerebellar ataxia or hereditary cerebellar cortical degeneration, and that the determination of this allele would allow to diagnose and/or predict hereditary cerebellar ataxia or hereditary cerebellar cortical degeneration in dogs.

The invention claimed is:

1. An in vitro method for diagnosing and/or predicting hereditary cerebellar ataxia in a dog, comprising :
    obtaining a biological sample from the dog,
    determining in the biological sample the presence of a homozygous adenosine allele at the nucleotide position 296 of the arylsulfatase G gene cDNA sequence of SEQ ID NO: 1, and
    diagnosing and/or predicting the dog is or will be affected by hereditary cerebellar ataxia when the homozygous adenosine allele is detected,
    wherein said dog is selected from the group consisting of American Staffordshire Terrier, American Pit Bull Terrier and Pit Bull type.

2. A method according to claim 1, wherein the presence of the homozygous adenosine allele is determined by polymerase chain reaction (PCR) and pyrosequencing, by sequencing or by specific amplification of said allele.

3. An in vitro method for identifying a dog which is healthy carrier of hereditary cerebellar ataxia, comprising:
    obtaining a biological sample from the dog,
    determining in the biological sample the presence of a heterozygous adenosine allele at the nucleotide position 296 of the arylsulfatase G gene cDNA sequence of SEQ ID NO: 1, and
    identifying the dog as a healthy carrier of hereditary cerebellar ataxia when the heterozygous adenosine allele is detected,
    wherein said dog is selected from the group consisting of American Staffordshire Terrier, American Pit Bull Terrier and Pit Bull type.

4. A method according to claim 3, wherein the presence of the heterozygous adenosine allele is determined by polymerase chain reaction (PCR) and pyrosequencing, by sequencing or by specific amplification of said allele.

* * * * *

SEQUENCE LISTING

```
<160> NUMBER OF SEQ ID NOS: 65

<210> SEQ ID NO 1
<211> LENGTH: 1608
<212> TYPE: DNA
<213> ORGANISM: Canis lupus familiaris
<220> FEATURE:
<221> NAME/KEY: allele
<222> LOCATION: (296)..(296)
<223> OTHER INFORMATION: guanine allele

<400> SEQUENCE: 1
atgggctggc tttttctgaa ggttctgttc ctggggggtga ctttcttggg atgcctttat      60 cccttgtgg atttttgccc cagtggggaa acaagaggcc agaagccaaa ttttgtgatc       120
attttggcag atgacatggg gtggggtgac ctgggagcaa actgggcaga aacgaaggac      180
accgccaacc ttgataagat ggctgcagaa ggaatgaggt ttgtggactt ccacgcagct      240
gcctccacct gctcgccctc tcgggcctcc ctgctcaccg gccggctggg cctccgcaac      300
ggagtcacgc acaactttgc ggtcacctct gtgggggggcc ttccgctcaa cgagaccacc      360
ttggctgagg tgctgcagca agccggctac gtcacgggga tgataggcaa atggcacctc      420
gggcaccatg gcccttatca ccccaacttc cgtggttttg attactactt tggaatccca      480
tacagccatg atatgggctg cactgatacc ccgggctaca accaccctcc ttgtccagcg      540
tgtccacggg gcgacagacc atcaagaagc cttgagaggg actgttacac ggatgtggcc      600
cttcctctgt atgaaaacct caacatcgtg gagcagcccg tgaacctgag cagcctggca      660
cacaaatatg ctgagaaagc tatccagttc atccagcatg caagcgccag cggaaggccc      720
ttcctgctgt acatgggcct ggctcacatg cacgtgccca tatccaggac ccagctctca      780
gcagtcctac ggggtcgaag gccatacggt gcaggtctcc gggagatgga cagcctggtg      840
ggccagatca aggacaaagt tgaccgcaca gccaaagaga acacattcct ctggttcaca      900
ggagacaatg gcccgtgggc tcagaagtgt gagctggcag gtagcgtggg tcccttcact      960
ggattgtggc aaactcatca aggggggcagt ccagccaagc agaccacctg ggaaggaggc     1020
caccgcgtcc cggctctggc ttactggcct gggagagttc ccgtcaatgt caccagcact     1080
gccctgttaa gtgtgctgga catcttcccc accgtggtag ctctggctgg ggccagcctg     1140
ccccaggacc gacactttga cggtttggat gcctccgagg tgctctttgg ctggtcgcag     1200
actgggcaca gggtgctgtt tcaccccaac agcggggctg ctggagagtt cggagcccctt    1260
```

| | |
|---|---:|
| cagacggtcc gcctggggtc ttacaaggcc ttctacgtca gcggcggagc caaagcctgt | 1320 |
| gatggggacg tcgacgggga gcagcatcat gaccctcccc ttattttaa cctggaagat | 1380 |
| gatgttgcag aagctgtgcc tctagataga ggtagcgccg aataccaggg cgtcctgccc | 1440 |
| aaggtcagag agattcttgc agatgttctt ctagacattg ctggggacaa cacctccaga | 1500 |
| gcggattaca ctcgccatcc ttcggtgacc ccctgctgca atccccacca cgtcgcctgc | 1560 |
| cgttgccaag ccaccggatg gaccgatttc cccacaggca gatgttag | 1608 |

<210> SEQ ID NO 2
<211> LENGTH: 65300
<212> TYPE: DNA
<213> ORGANISM: Canis lupus

<400> SEQUENCE: 2

| | |
|---|---:|
| atgggctggc tttttctgaa ggttctgttc ctggggtga cttcttggg atgcctttat | 60 |
| cccccttgtgg attttgccc cagtggggaa acaagaggcc agaagccaaa ttttgtgatc | 120 |
| attttggcag atgacatggg gtggggtgac ctgggagcaa actgggcaga aacgaaggac | 180 |
| accgccaacc ttgataagat ggctgcagaa ggaatgaggt gagtcttgag ggtgccaagc | 240 |
| cagcatctct gtggatgtct ggctccctgc gggagagggc agcggaaagc acttaaagaa | 300 |
| caattgatgg gtccgtgctg atttagttaa ttgattaatt ctgtttgaaa ctagtacagc | 360 |
| atcttgaaga aatccatcca ttcatccatc tgataacatt agggatgtgt gtgcgtgtgc | 420 |
| gtgggtgcat gtgctaggag ctgggaatac ggaggtgaac aagatccctc tggtacttaa | 480 |
| catctgtgtg agggatgag ttaaaaggaa agtaggaact acaactgagc acatgagccc | 540 |
| gcatcaggga gttttgggag tctgcaaggt aggccgtgga acccagcctg ggccagttc | 600 |
| aggggagcag atgacctttg aagagccact gagtcagcga ggcccacaaa ggtaagagga | 660 |
| cttgtctgtg agcggatggg acttactgct ccatggaagg gcacaccatc cagggaaggg | 720 |
| cctgtgcatc cgagcgggtc tggaggttca taagccccct tcccgctcgg aaagagaaca | 780 |
| tgtatgagtg tttagcctgc tgggtaggca tctcacgctg acgccagtcc agctgctggt | 840 |
| ctagctcaga ttcccacctg tgctgtgtcc tgtgcctccg tccagtgggg tggggatcgg | 900 |
| tccggctagc tggttgggac accacgtggg gcatcactgc agtacttcag ccacttgtag | 960 |
| cctccagcct ggggcttccc tggtgataga gtctcggggt ccctgcatct ggtctcaccc | 1020 |
| actcgagtcc gtcctcctca ccttggccaa actgaaagtt ctagaacact cctccattcc | 1080 |
| aatgtttcag tggcattttg tggccctagg gatgcaaacc aagctctgga cagcagcttc | 1140 |
| caagaccagc ccctcctcca cattggtact caacccgcgt ctccaccccc acccccaccc | 1200 |
| cccaccccc accttcactt gttgtctctg tctgggtctc ccgtatgggc ctccgtcttc | 1260 |
| cagggcact ttctacttcc aatgatgcat cagtttcttc cttccttcct tccttccttc | 1320 |
| cttccttcct tccttccttc cttccttcct tccttccttc cttccttcct tccttccttt | 1380 |
| ccttccctct ttctttctta agatttgctt ttatttattc atgagagacg cagagagagg | 1440 |
| ctgagacata ggcagaggga gaagcagact ccccatgggg agcctgtgtg ggacttgatc | 1500 |
| ccaggacccc gggatcacac cctgagccaa aggcagatgc tctgagccac tgagcccccc | 1560 |
| aggcatccct gcttggtcag ttcctactca ccacctggga ccctagtgcc tcttgaggtc | 1620 |
| cccgggaaag cttccgggga tgctgcctgg gttccctgct ggggttctct gctaaccccc | 1680 |
| ttgctgcttt tcatggtgat tgtgtaacca cctcaccccc tgtgtcaggt tggataggat | 1740 |
| gctcccccc caattgatgc ccacctggaa actcagaata tgacctcgtt tggaaacagg | 1800 |

```
gacttgtttc ctgtttttag tatttagtta tggatttttt ttgaagattt atgtatttat    1860
ttgagacaga gcacaagtgg ggggtgtggg agagagaaac agactcccaa ttaagcaggg    1920
aacccgatgc agggctccat cccaggacct caggatcatg acctgaacca aaggcagaca    1980
cttcatcaac tgagccaccc aggcgcccct tagttatgga tcttaatgat accaccctcc    2040
atggagagtg ggtcctaaat ccaatgacca ctgtgcccat ataagaagag agaagaatgc    2100
agagagacac tcagaggagg tgacctaagg cagaagcagg gaacgcagtg atgtgtccgc    2160
aggctgagaa tgccaaggat cgctggcaac cgcaagacgc caggagagag gcgtgggaca    2220
gattctctct ctgagcctcc agaaggaacc aagcctactg acatcttgat ttcagacttc    2280
cagcctccag acccttggga aaatgacatt tctgtcattt gaagcctcta gtgctaattt    2340
gctctggcag ccacaggaaa atcctacaac tcccttctag ccctggtctt caggaggaaa    2400
aatgcctggt ctcttcttcc cctcttgtat tcctagcaca gagcattgtg cctggcaccc    2460
agtaggcagt tgataagtca ctgtttatca gtgaatgggc tttaggtcaa gataccttga    2520
catgtcaatc caattttgca tgttggattc ccaccccctc ccccgggaga gatttaatcc    2580
attgcattta ctaaatcctc aaagggaaca ggattgccaa atgcttaaga acttctgctt    2640
ttagtgtcaa gtgggttcgt ggggaagtat ctggcccatt atttaaaccg agatttctgg    2700
ggcctggacc ttccccttac ggctgtcccc accctctcat cctgtgcaga aacagcacct    2760
cgtatgcaga tgcaagcacc gtttggtggg ctctcctatt tcttcctccc tttatgaaaa    2820
tgttctctcc atttgagcct gtgacagggg ccaggcggct ggccctctgg ccccatgtcg    2880
gcagcggctc ttctctctgt gctttgttga caggaaagca ggcttcctgt gaggccacgg    2940
gttgattcat cgctggcttc tcccccctgcc tactcacggc cagtggggaa ccatgacttt    3000
cagacgagaa ctggttgcca aacagggtct ctgggcgact tgagaaagtg tctttgtttt    3060
tttattgtct ctttttttatt agggtattgt ttcctaagac tctcacaaca aatgactata    3120
tactgtgtgg cttaaagcaa ctcacattaa tcctctcaca ggtcaggagg ctagaagtcc    3180
tgaatcaaga tgtcggcagg gttggaaact tctggaagct ccgaggcaga attggtgccc    3240
tgcccctctt gtttctggtg gctgcaggcg gtccttggcc tcctgggcct gtggatgcat    3300
cactccgttg tctgcctcca ctgttccatg gggctcaccc tgtgtgtgtg tgtctaaatc    3360
cccttcttct cataaggctg ccgccactgg ctttcgggcc catcctaatc cactatgacc    3420
tcattgcaac ttgattacat ctgcaaagtc ctatttccaa atgaggtcat attcccaggt    3480
tctgggttga cgtgaaattt gggggagatg ctagtcaacc cagaacaatt agctatcccg    3540
cataggtctt tagccctgct cctaacatca tctgcaatgt ggcaggtgct tgatgaacga    3600
ttgttgcttt gaagactaaa tatcctgctt aagaagttgg tctcaggttc aaatcccagc    3660
tctactactt tccatctatg tgactctgga caacttacat cattccttgg ggacagtggt    3720
agcacccgtc tcataggatg ttgtggggat tagattaagt catccatgca ggcaattagc    3780
acagagcctg gctcacgata gacacagata tatgtgagct atggttattt ttggtattgg    3840
tcttagaaat aatatccatt tgaattgttg atgtgaattg ctactctgc ataatgaaag     3900 atttaaacgg taaatcgtgg aaggaggagt gggttccaga gacaaatccc tgttaatctg    3960
gatgtggacc atccacacta agccaacatc tgtatttgaa tcaaatgtga cagttgtgat    4020
aatagctaac ccgtcctgtg cctatgtgag gttccaggct ctgggcatca ctccggttaa    4080
ttctggccac cacccatgtt tctcttcttt cagaagagat gaggtgagga aatcaagatc    4140
aagccatttg tcctcttggg atctgcttga gtctgttcag tgctagacca agtccccaag    4200
```

```
gcaacattta agtgtctcca taacattcct tgccagcaca caccattagt gtggattttt    4260
cttcttcccc atttggttat ggtagatgtg atttgccaaa tttatgaatg gaatgggccc    4320
cattcacaac atgacccgga tgtcattgtt gcagaacaaa aggattccct ggggaaagaa    4380
aggcagagct gttagtgcct caattttggt tcctttacag acctcttaac ttccatttat    4440
gtagtggtga aggagggatc gtggcctgaa accccacagt cttgagggtt atgacagagc    4500
tatgtcattt atggtagctc aggcctaaga gcatctcatc atgttatcac acaggggtaa    4560
actgaggcca gagagaagtg aagtattttt actactctgg tcgctttcca gcaggtgggg    4620
gcaggttatc tagtttgcac ttgtcagtag gttcacccga caacctgact ttcgcccttg    4680
acctggtggg ctgggcgttt tgtcactgtg ctgtgcaaat ctgagctgag agctactgtt    4740
gaacatttga agtttaaga ataataagat aatccaaaga aaataaaaat gtcagaattc    4800
aggtgaaaag gctagggatt tagtaatcag ctaatactta aaccacttgg agggactccc    4860
aggctggctt agaagggagt tgataggaca ctgtaggctc attcacttgt gcaaattgac    4920
ttgcaagtac gttacctttg caccttgatt tctttccatc ctgttccgcc ccttctcagt    4980
ccccagtcta atctgagtca agtcaatgct gctgctgagt agaggcagtg acttagctag    5040
gaatcaaaga tcgatattca cccctggaag gtcagaggct ctcgggggct tgagtctgtt    5100
tctagaaagg gcctcagtga agaatgaatt gatctgtcaa atcagtcaaa caccttctgt    5160
gatttctgtt ctcggcattg cttttggca aacgttcatt catcctgtta cctctcggag    5220
ttttctcagc tgtcccactg cctccggggt tttgcaatga tcccaaggaa gctgggaacc    5280
aggctgccat tcataactgc aggggatggt aatgaggtct tcctgagagc tagggtagaa    5340
agaacattct gagtgaggct tatcttgata agggaaagtt tccctcccca ccatgcagtc    5400
cccttccagc tttatctcca tccgctggta cagtgattca cttgatctta gccaaaaggc    5460
tgagaagcga ttggtacagt gattcagact tagggttgag ggagaaaacc tcttggcctg    5520
tgatcttcac tgcttagaga aatctgctca gcatcccagg acaggtgatt ttatctcttg    5580
gcccttaggt cagtaggtcc aatggacata aaatcatgca atgcccacct accaaccagg    5640
caggccaagg tgaagcttac atgaaaggtt ctgtaggatt tagccatgtg gttctgtgta    5700
atagaatggg gacctgcagg aatgcaatca tctagataac acccaatctt agagaaaagg    5760
agctgaaata ttagccaatg aggccttggt gccagcctgg ttcacaagtg caagttcaaa    5820
attgcctgtc tgatggctat tgtgcatttt tgttaagtct cccgacaaga gtcatttgac    5880
aaggaatctc tgctaagagc ccatcatagg acaaatgctg gaagatccta gccagctgtg    5940
ccctaagagg cttccagcca ggtggtaaat aagacaaaag aagcagcttt tatttttatg    6000
tatgtattta tcttttgcaga tttatttatt catttgaaag agaatgaggg atgcctgggt    6060
ggctcagtgg ttgagcatct gcctttggct caggtcatga tcccagggtc ctgggatcaa    6120
gtcctgcatt gggctcacca tagggagcct gcttctccct ctgcctgtat ctctgcctct    6180
cttctgtgt ctctcatgag taaataaata ataagcaaaa tcttagattg agtacaggga    6240
aaggggcaga ggaagaggga gagtctcaag cagactgtgc taaacacaga gcctgatgtg    6300
gggcctgatc ccatgacccc aagatcacaa ccctgagatc atgacttgag ccaagaccaa    6360
gagtcagata cccaagtgac tgtatcaccc aggcacccca agacatgcag cctttagcat    6420
gcagaaggga gatgtgctgt atgagcagga accctgtacc tcctgcccca gggctttaat    6480
aacctgata gaatggatag aattgaagcc tctgggatag aattagcacg ttacttatcc    6540
cttggtcaca gtcaagaatg agaaaggtcc atgctgggct tcttgccttt tgatgagaga    6600
```

```
acccagagca agaagcatgt tgaagacagc cctatggggc tgcaggaaga gagagtccat    6660
ttctcccgag ggaagccaag aggtacttac ttgataaagg acttcactgt tgagaccttta    6720 aagaggaata ggaattagaa gaaggggag gaaaccatgt tatagtaaga gggaaaaact    6780
tgagcaaaga cccaaaaatg ccctttcact ggacacatat tcctggaggt tcccccaggc    6840
actctcccag gtgctgggaa tgtatcccaa tccaaacaat aagaagccct tactttccag    6900
ggtgaccatt ccagtggttg agtgtgactg ggacggaggt ggaagtgagg ctgggccaat    6960
ggacctggcc gctggtgaag ggccttgtgt gcatgctcaa gtgtttggac ttggtcctgg    7020
aggcagtggg ggccttgagg agtgaagtca ttggcctgca tttgagatgg attgctccag    7080
cttaccaggg gtggcccatg ctggcagctg ggagggcagt gggcagattg caggagcctc    7140
caggatagtg tatggctcag ggttgtggca gtggggaggt gtccaatcta ggaggtactg    7200
ggatgcctgt gtgtgcatgt gttcatgctt cttgtcctgt gtctagtgtg tgtccttcct    7260
ggagtgtgaa tgtactcata tccacagtga gaatgtggaa gggaagcgg gaaattgcca    7320 aggatcatac caagctcagc tgcgataatc ttttatttt attttatttt ttttaaaga    7380 acagagtatg agtggatgga gggaaggatg gatggataga tggaaagatg gaaggatgga    7440
tggattaaag aaaggatgga tggatgaatg aaagactaga tggatggatg aatgaaagac    7500 tgatggggg atccctgggt ggcgcagcgg tttggcgcct gccttttggcc cagggcgcga    7560 tcctggagac ccgggatcga atcccacgtc gggctcccgg cgcatggagc ctgcttctcc    7620
ctctgcctgt gtctctgcct ctctctctct ctctgtgact atcataaata aataaaaatt    7680
aaaaaaaaaa aaagaaagac tgatggaagg aagtatggaa ggatggatgg atggatagat    7740
ggaaggatgg atggttggaa gtatggatgg atgaaaggat ggatggagga gtaaaaaaaa    7800
acacatcaag tttgctcttt gctgccacac ttgcatgtag tttacaaagg gcttgcctat    7860
cagttccctc aatgaccca cctgacaact ttctgagcgt gaacttggcg gtcttcccat    7920
ttcacagaag gcaacacgga ggccatgctg tgctcggtga gtcccaccaa agtgtttctc    7980
cagctctcac ctcccacttc atccctctac atgcaaaggc cacagcgaat aatttttaaa    8040 acctgttct gcctccaaga cttttaaatta tgaatggagc aaagatagcc tttattccag    8100
gcacacagca atttagagag ttaccacgga aagcctcatc atctatttta aattcctcct    8160 aaaatgaagac tggacacgct caacctcgca acattatgtc cctccagggc tttcggggca    8220
gcgtttccag cactgacgtt ttccgatcct aatacacgta atttatgcga tggcaagttg    8280 cttttggtttc tgtctggctg tgtcttcatc tgcgccgatt ttcctgttaa caggctgctg    8340
taatgtctgg ctctgtattt ccagcttgcc ttcacagtgt attttcaggc tttaattagg    8400
acccctgttg gtgaactggc ctgagcctgc ccagatagat ttgggggaaa acaaaagctt    8460
tccaaatagc aagaccattt tatcgcttat taattagtct ctgccaaaca gagacagagg    8520
ctgcgagaga ggaaaggtga cggcaggtc agttcactgg gccgcctggg gtgttgtgag    8580
gttttttttt gggggggggg gcgggtggaa aggtagcaag agtatggtca gggctctcca    8640
aagaccttgc aataaaggag agaagattgt ttctgagcgt taagctgtgt gagctttaac    8700
ccaaggtggg gaaagaattg aaccctaaaa agcatcagct tgagcgattt tgtgcaaaat    8760
ggacgaatgt acgttttcca atcaaatgac cccttcaagt tttgtttgct cgctcaccag    8820
atgttgctgg ggtggttcca tgccagcaag gcacgccgct gggggctgcg cttggaactc    8880 taacccccgtc ctcgtaggac ccaccgtctg ggaggactg gaggttacat gtgttggagg    8940
aatgcactaa cactgttccc ccgagggtgg tggtgtgtgt tccaggggag cccacagcca    9000
```

```
ggctagtcgt taaagacagg caagcaggga cagcgtctag gcaatgggag tactggtcag    9060
ctcgggctag tgtaacaaat acaatagaat gagtggctta acagtagga  attgttttc     9120 atagttctgg aggctaggaa gtccaagatc agggtgccag tggggtccag ttctgctgag    9180
gaccctcctg gccgcagatg gccaccttct ctcactgtgt ctcacatgga ggagagaggg    9240
agagaggaag agagacctct ggtctcttcc tcttgtcaga gaacactaa  tcctatcata    9300 gggatcccac cctcctgacc tcatctaaac ccgattacct cccaaagctc ctacctacaa    9360
atgccatcat attagaggtt agggcttcaa tgcaaacatt gggtccatag tgccagggaa    9420
gaaaattgtg catcccaaac ccactgacaa gcctcagtct acagaggaca gaatttccct    9480
aagcttagcg gactgaaggg ttttctgtg  gcccattaga attctcgtag cattgattac    9540
ctccacactc accaaggcaa actttggatt ctgatttccg ctgtaattca tgcacaagaa    9600
gagaacctgt tgactgctct gacactggtt tctgcaccca tccctggaag ctagttggga    9660
gacgggcatt ctggtgtctc tctcaagctc atatgggttg tgtggatgtg agtcaggccc    9720
ttggggctgg caccaccaag ggtgagtctc gggacctccc tagcccaaga ctagccactt    9780
acccaaggca attccctctg ggtttacctt accaacctct gggttggcct agttccagct    9840
accttctctc agatgtgaag ggagtagaag gagcatggga ttttggttgg gcaggcctgc    9900
gttcaagttc tagctctgtc atttccccaa tacgggggcc tatagtcttg cctgtggcac    9960
agtgcgtggg caggacaagc tgcatctgta cccgtgccaa ctctgtggtc ttgggaaagc   10020
tgcttgagct ctatctgcct cacctcccct acctgtaaga tgggaatcct cgtgatttga   10080
aatcatatat gcaatatgat tggggtggga gtcacttgac aaatgacagc tatttttact   10140
ctgataagac agacaaaggt aatgccatt  tataccttag gtctccgctt ccgtgtagct   10200
tcttttgaga agcacttaac atgtgtgtat gtgcaccttg tagagcccag gaacttcctg   10260
tcctgcttcc tgtcctcaga gctctctcac acattgggat cctccaccac ccttattgag   10320 cttgggcaa  cttgagggca gggcttgaca gtgtcctctg ttatattctg ggctcctatc   10380
ctattgtacg cacaccgtca tagccaggac tgattctaag tggcagcagc ccagctcagc   10440
cagcctaagc acaaaagagg cgaagctttt gttcataaat aaactctgca gagacccgt    10500 cttgtgtctg ggcttttggg ccagttgctt attctttcag gttcctccat gtgatgggag   10560
aggtggccct tgccctacat cagagcttgc ggttcaaagg gaacaagaga gctattcctc   10620
actgtccggt tcagaaaatt ccagattgaa gggcacctgg gtggctcagt ggttgaggtc   10680
tgcctttagc tcagggcatg atcctggggt cctgggatcg agtccgcatc aggctcccag   10740
tagggagcct gctactccct ctgcctatgc ctctgcctct ctctctgtct ctcatgaata   10800 aataaatct  taaaaaaag  aaaaaagaa  aagaaagaa  aagaaatcc  caggttggat   10860 tctgaatagc cctgcctggg tcacgggctg tgggcccgat ccttgaggat gagaggttgt   10920
gctactcggc ttagcccacg gcagagtctc atgcccatgt tggggtgggt gggtggggg    10980 taggacgcgg gcatcagcct aagagtcatg tggaagggt  gggtgggaa  gatgcccgcc   11040 tggtccagcc cagatattgt caggtgaatg tctaccttca gacaagaaag ggctgccagg   11100
aagtttcatg tgccaaagtc cagactagaa gccaaagtcc agactcatca ttgggggggt   11160
tggctggagg acggggcgg  ggggaagggc gggaggaaac agtgatgatg ctcactggtg   11220
aaggacaggt aggaatttgg aaggacaaga ggaaaaggca gactttctgg gctgaggtgt   11280
cacagagtcg aggtgtcgga gaggtgcgtg tgggacatgt gggagggagg gggggcaagg   11340
gctgccagct gctccgggaa caggagtcct gttgggctga gctcctgggc tacgtagggt   11400
```

```
ggaggggtag ggtcctggag ctgccatgac aaagtaggac aaacagagtg gcttaaaaca  11460
acagccgtct ctcctctcac gcttctggaa ggctggaagc gagaactcaa gatgctggca  11520
gagccatgct ttccctgaag ttctaggggtg gtttccttcc tcgcctcttc caacttctga  11580
gaaccccagg cgttcttcag ctcgaggccg tgtcactcca tcctatgcct ttgtcatcat  11640
gtgaccacct tccccctgtg tgtctctgtc ttctcgtggc attctctctg tctctctcct  11700
cttcttatca ggacaccagt cagaagaggt tgaggactca ccccaatcca gcatgacctc  11760
accttgacta ttacatcccc aatgactcta tttccaaata aggtcccatt cgcaggtccg  11820
gggtggggag cttagaact tcaacctgtc tttttagggg acacagttca gcccacatta  11880
ggcagcagtg actcagggggg ttgaagaagt aggttgagcc agagcatgga gggccttgat  11940
ggccacacag aagggagtca ctgaagactt gaggtccggg gatggcctga cccactggtg  12000
tgcatgctag caggggctgg aggagtgagc ctggcatctc agaaggtcac cgaagtgatc  12060
tgggtgaggg acaacggctg tatagctgcg gggtgacatt gtttggagtg ggaggagctg  12120
aaagaggtga gaagtggcgg aaggacttga aaatagtatc tcagtctcca gccaggttta  12180
ctgggaggga tgtggacatg gggtcttgga gggaggatgc tgagcttggt cctgtgcaca  12240
ctgaggctga ggtgacgtgt gacgacatac ctgcggcagt gaatgtgatg cctgggtagt  12300
atgaacagca gcggggggcc ccgcctcccc cacaccccgc ccattggtgc ccagtgcact  12360
gctctcctac ccacctagaa tgttctctct ccccaccatt tagtgagtcc tgacaccgat  12420
taccttgact atagtgaatt tttaattcca ggtagagaac ctggaactct gctagatgct  12480
ttgtgcacat catcccactg aatccctcaa ataagctggt gaagtagggg tgttatgctc  12540
attttgcaga ggtagatact gaggcctaga tttagttacc tgtcttatct cacactagag  12600
ggagtggagg ctgggatttc acacagagct gtttgtctac atgtttatca ttcctatcac  12660
tctgcctccc atagctcttg ctttaaattt ctctgacgag gctcatcttg tcttcgtatc  12720
cacatgtcct aacacctcta aagttgagct actcaatgga aaggctgtgg ttcctaccac  12780
tagctccccc agcaagccct gatgtggttg gctgacctcc actgaggctc ctggcagttg  12840
gaggtgacca gaggggtgcc ctaccccaag ggccactcct atgttgtgct ctcagagaat  12900
tgctttccct ggaattgtac aggacacaca caccactg gggtaagact gccctgggga  12960
ctccagttgc ctggggcccc atctggctgt ctctggggct gagaggaacc cgatcttgga  13020
aatcctgtgg cccatttggc cctttgtgtg tgctccagct cctgggctgg acagctctga  13080 tggagggggct ctagaccacc ataatgactt tggatttact cagattgtag tgagaaccta  13140
ttagagggct tccagccaga aattaatgtt agctgataaa cagttttttca gattactttg  13200 gcttccccat ggaaaatagg gggaagggga actgggagca ggaatggaag tggggagcag  13260
ggttgccaca tacagctggg cagattgtgt actgctcaac gccggacaac agcatgaatg  13320
gcatccctgg caattctaca acatgatggc tctggggaga caatatagac tatggtgctt  13380
gtcttggtgc aagatggtag aagctgggac taggatgtta gcaggtagac ggagagaaat  13440
ggatagattc tagatctctt tggcagtaga gtcctattaa gaatgtgctg atggtttggc  13500
tgtggagggg gaagagaaga gaggaatcaa gatgactcct ttggactgag taatcgagtg  13560
agaggtggtg ccatttactg agatggggaa gacgggaagg ggaggaacag gtgtgcaggg  13620
acaaatctaa agcagaacca gataaacttg cagagaccgg cagagaaaac aaccatgggc  13680
cagatgggag caacgtctgg ggcccaagac cagtgggcct ttctcttcgt gctctgggaa  13740
gcccagtggg cccaggggcg actggggtct gagacagaat gggtagtagt gggcagggcc  13800
```

```
gttctatggg cgtgtgacct gtgcagccac acggggcccc atgctttagg agggccctgc    13860
tcttggctta aagctctgtc actgccatct tgaaatgctt agtaaatttg gagcaagggc    13920
tccctcgttt tctcttgcac agggccgggc aaattgcaca gctggttgtc ttgcagtaaa    13980
gagatgacac caacaggcct gggccagccc gcacagagct tacagaacat gcagattcaa    14040
cccagggtga atcccggagc aagagatgct cacacatgct gtgtatgtaa agtgcctggg    14100
ttgataagca ttaactggga gtgataagaa ttattacaag ggacatttag gagtgtgagc    14160 tgggagggggt catgggcctc aatctgggga ggcagagaac agaaaaggcc gggcagagat    14220
ggatgtttgt cttgggagca acaatgtgct ctgcaaggtg gaacctggtt tggaattcga    14280
agagtgggag ctgccggctg cctgcaccag ccaggacccc tgtgtcccca ggatgtctgg    14340
caggcgggga tgctttggag aagccccgc ctggaaatg ggtgcatagg gattgaggga     14400
gggaaacagt gtgtcttcca gccccggggg actgagggcc cagaaggaat gtcggcaggg    14460
gtgggaagcc agcgccctg ggctccctga ggcctggagg gaggcctcgc cccacacctg     14520
ttacccagcg gcgcatgctt gggcacccac cttccccgcc ctcgttcagt cagatggagg    14580
tacccacagc ctgcttccaa gagtggctgc aggcccaagc ctgtgcttct ggaacttcac    14640
ggtgccatgc cactgctccc ggatcatggc ccctcgttgc catttgtagc cttgaaagat    14700
ggcctgaggg agctaaccta ccttctgggt gagttctgtg gggtggaggc tgtgggaacc    14760
agcaggtgtg ggctgaggat gggtggctgg ccccgaggaa gccccgtgga ggactcttct    14820
ttccagaaac atgaattccc agaacccctgg cctgctccag agaccccaga ggtgctgagt    14880
gtggcctctt agttccaggc agaactccaa tgagaccaga tgatcaggtg cctggttttt    14940
ctcttgaagg ctttttggga ttggaggctc tcgggccaac cctgaattaa tcaaaccagt    15000
gttttatcat gttatttcaa gaagctcttc tgacgcccgg ttagcaattc tctcatttca    15060
cagccagctg cattttggag atgtgtgtgt gtgtgtgtgt gtttgtgcgc acgtgtgtgc    15120
gcgtgcgtga cccccaccag tctttggatg aagtctcaaa gcttcttctt atgccagcac    15180
cctgctcccc ctcccttacc cggagtctga gggactgggc atgtctcctc tctgcttaaa    15240
gtcctcactc tatctcttgg aggggtctc ctcccgagac agtgggtctg tgcagtgggt     15300
accccaaccc ctcccccttcg gcttttccaga cacactctgg acttcctagt ggaagcagtg    15360
tggttaagtg gcacccacat gggatttgga attggatggg cctgagttta aacgctgcca    15420
tggaaacctg gctgtgctgg gtaacgctgg gggccggcgt ggagcgcaat gcctgggtac    15480
agaccttggc tcctccgtgc gcggcagtgt gttgtgctgc ctcagtctcc ccatctatag    15540
tgggagtgct taccgcagca catcctaggg ctgccgtgtt agatgagttg acacccgtaa    15600
cacggtgctg cataagggat cacaaccatt cgtggtgaag cagaaatgac ctagaaaggc    15660
ttttgtgcag aaactaaact gtaaggtcac tggggacagg gactgttctct ttacttcctg    15720 agaatctgtc acagatctgc ccctgcttac tgtctactca ttattttggg gttaaattag    15780
atgaattggt acatcaccac ctgagttata aatgagcatt ttctcatctt gcggactgca    15840
gacccgacac ccagctttgt gggccttttc tcctacctga gagagtctttt tctggcattt    15900 gtctctgaat ccgtaagcct cggatagctt gttttttttt tttttttttca ttgaagcgac    15960 attcttatga cataaaacta accacttttaa agcagatgac tctgtgacat tcagtacgtt    16020
tattgttttt taagattttt atttattcat gagggacaca gagagaaacg cagagttcca    16080
agcagaggga gaagcaggct ccatgcaggg agcctgattt gggactcgat ccctggaccc    16140
cgggatcacc acctgagctg aaggcagatg ctcaaccact gagccacccc ggcgcctcta    16200
```

```
gaacatttag aatgtggtac ggctactgcc tctatgcagt ttcaaaatat tttcatcatc   16260
ctaaaaggaa accccatccc cacccatgaa gcagagtctc cccattcccc accctgcctc   16320
cagcctgttt tccgtctctg tggatttacc aatctggggc atccgtataa gcagaattgt   16380
acagtatgtg gccttttgtg accggcgcct tccactcgtg tcatgttttc aaggttcacc   16440
cacgtcgtag caggtgtcag tggttggttc cttttcgtgg gtgaaaccca tccacaccat   16500
tccagagtgt ggatgtgccg catttcgttg gtccacaccc cccgctgaga gccagctggg   16560
ccacggccac cgtcccgcca cggctggtag gagcacgcag gatctgtccg agtacctgcc   16620
ctcactttc ctggggaatc cagtcctggt ggtggaatcg ctgggtcacc tgccatcggt   16680
ctgccagatt tttaaagttt tgccttatga tctctaggct ctagtgtagt atattgagag   16740
agagaaagag agagagagag agagaaaggg aaaggaacaa gggaagagga aaccacggcg   16800
ttgccgacac gccttgcagt cctgactgcc ctccagggcc atcaccctg cagatgccaa    16860
ggtcatggtg aagggcaggg tgtccagggc cctccctgct ggctgtcacc gggctagggg   16920
tagctgcgtc gtagggcgtc tgggagggc gtgaaaacat gacagacttc cagggctttc    16980
cttaggccag ttggccctgg tggctggaga gaggccgtag gtggtgtccc ttctaagcac   17040
tgtgttttaa cccccctctgt cccaagtctt ctgccagaat tgtgtgctca gagaaacagg   17100
gatttgtatg ccttccttcc cccactttct tatcccaggc tggctcctat gagggcatag   17160
aaaaaaaaga aaatgtttcc aggtcggtct aagcacccca agcaagcatg gccctgggtg   17220
ggctgcccag gcaagtgaca gtctcagttg agggctgctg tcaagtagtt tgggggccacc  17280
accgtccagg ggttatggca gaaaccagag gcctgaatgg aggtggcagg tgacgagccc   17340
gccaggctct gtggtgtgta ggaagggagt atttaaacat gcactgctct ctgcgacctc   17400
acctccttgc tctcacatgg gtccctgat gttctatctc atgacccttc acatcatgac    17460
gctaatgctt gcagcccca tgcaacctcc aaaacttgtg gtgaacctgt tcagggaaac    17520
tctgctcctc tgcactccct ccccgcccca caccttccaa tgacacttcc cagtaatgat   17580
tattttgagg tttggttgca tgttccataa gttgctggga agacacctcc ccttccctcc   17640
ctgttccatc ctctccctc ccctaccccc tgtatttag gagctggagg taagcagcca    17700
gcaacgtagg caaagccctc ctcacaggga gcttgcatgg aggaaggatg actcaaaacg   17760
aaaggatgca aaaataaacc agatgattgg ggttggggtc agtgctacca agtaggcccc   17820
agggtgcctg attagagcac agcagaggcc cccttgcagg gaaagagggg aggaaaggcc   17880
atgcaaagat gcaggagagc gtgccaggcc gaggctgacc ttgggaagga gctggcactt   17940
tgcagaccca acagaagact gtgtgctggg gccgtggag ggaggaagg ggaggcccat     18000
aagatgggct gtgggggact gggtattag agagcggacc aggcaatcat ctcaggatat    18060
taggcagtgg tcagaggggc acttgaaagc cccctggtg gggatccctg ggtggctcag    18120
tggtttagca tctgccttca gcccagggca tgatcctgga gacccaggat caagtcccac   18180
atcgggttcc ctgcatggag cctgcttctc cctctgcctg tgtctctgcc tctctctctg   18240
tctctgtgtg tctctcatga atgaataaat aaaaattaaa aaaaaaagc cccccctggc    18300
tgttggggga ggatgtgtcc tatgtggaga ggagggaga ggcatggagc cctgctttgc    18360
tgtgctgacc tggcgtctgt gggccagtcc ctcatcccac cagacctggg gcttcatgct   18420
gacctgggtg gcaggtcagc ttgcgggccc agcttggggc accccgacat gcacacttcc   18480
aatgtgccag gctgtacctg aagccacccc tccacccctc cctcccctcc ctaccttccg   18540
gtccacctca gctcccaacc ctgctgctgc cctgctcgtt ctagactcca gatcgacacc   18600
```

```
cttttgaaac ttacaatatt aagcattatt gactttttaa tattaaaaaa aaatctcaaa   18660
catgatagaa aatgaaaaga ggggcagccc gggtggctca gcggtttagc gctgccttca   18720
gcccagagcc tgatcctaga gacctgggat cgagtcctga gttgggcttt ctgcatggag   18780
cctgcttctc cctctgcctg tgtctctgcc tctctctctg tgtgtctctc atgagtaaat   18840
gaataaaata ttaaaaaaaa agaaaatgaa aagaatagtc aaataaacac gagtatactc   18900
aaccgttaat accattctgc cattttttgtt tgtccttgtt ctatctataa ataaggtggt   18960
ggtgtttttc ctgagccatg tgaaagtgc agctgtgctc ttttattata aacactatag    19020
catgcatctc ttaagaataa aaacattcat agtgtaataa cttccttagt gtaataaaaa   19080
tgtattcttt taaaaaaaga ttttatttat ttattcatga gagacacata cagagagagg   19140
cagatgcata agcagaggga gaagcaggct ccctgcggga agcctgatgt gggacttgat   19200
cccaggaccc cggattgcat cctgagccaa aggcagacgc tcaaccactg agccatccag   19260
gtgcccctaa aaatacattc ttaatgtaat aaaaaatgtg gtatacatag accacaggag   19320
actattcagc tgtaaaaaaa gaaggaaatc ctgccatttg tgacaacatg gatagacctt   19380
ggggacatga tattaggtaa aaggagaaag acagggaagc ccaggtggct cagcagttta   19440
gtgcctgcct tcagcccagg gcctgatcct ggatactggg gatcaagtcc cacgtcaggc   19500
tccctgcatg gagcctgctt ctccctctgc ctgagtctct gcttctctct ctctctctct   19560
gtgtctctca tgaataaata aataaaatct taaaaaaaaa ggagaaagac aaatattata   19620
tgatttcatg tgtatgtgga atctaaaaaa gccaaactca cagatgcaga aacagattg   19680 gcaggtgccg ggggtgtggg tgggggagat gggtgcaggg ggttaaaagg tacaaactcc   19740
cagtcatgag ataagtaggt tctaggcatg tagtacacag catggtgact ctggttaaca   19800
atactgtatt gtatgtgtga aagttgctaa gagactagat cttataatcc tcatcacaag   19860
aaaaaaaaat catagctatg ggaagtgatg gccattcacc aaatttactg tggcgatcac   19920
ttcccagtat atacatgtga caaatcatta tgttgtacac cttcagtgga tacaatgtta   19980
tatgccaatg caactggaag aaaaaaaaag aacaaaaaca ttcttctaca tggtcataat   20040
caagaaaatg gacagcgatc ccctgatgtc atcttatatc cagcccacac taaatttccc   20100
cgattagccc tcaaatgtgc tgtaagtata tttgaactgg gatccagcca aggatcatgt   20160
atcacatttg gtttgtctct tcaatgtcct gtagtataga atatcctcct ctatcccatt   20220
tttcccttgg atattgactt tttgaagaac tgcaccagtt gtagaatgtc atagaatgtg   20280
cagaatggtt tgttagaata tttccttgtg gtgtcattta acttgttctt ctattagtta   20340
catttcctat aacctggaca ttgggtccag aggtctgatt agattcagtt taaatattct   20400
tgacaagaat ccttgatgag ggcagcccag gtggctcagc ggtttagtgc caccttcagc   20460
ccagggtgtg atcctggaga cctgggatcg agtcccacat cgggctccct gcatggagcc   20520
tgcttctccc tctgcctgtg tctctgcctc tctctctctc tctttcatat gaataaataa   20580 ataaatatt ttaaaaatc ttaaaaaaa aagaatcct tgacaagatc aacttcctat        20640
catcccatca ggagacacac aggttgccct attacgagtg acatgaagtt tattcatatt   20700
tcttgatggt agagaaatgg ctagacttct tatatatttc tccacagtat ctaaaaaagg   20760
gttgagcatc caacaaagtg taataaatac agctggttct tgttattggc agtcgttgct   20820
ctataaagtc actgagaaca ctgagttacg gaatactgaa ccattgcttc tagggcatct   20880
acagagttag gttcctgtgg gccttttgtt acgttttgt caaagatca gtacagaacc       20940 ctgttttatt tatttatttt taaagattta ttttacttat ttgggagaga cagagagcaa   21000
```

```
gagagagtga gcaagagaga gagcatgagc gaggggaggg gacgggcaga ggggaagcag    21060
actttctgca gagcagaacc catcccagga cccggggatc atgacctgag ccaaaggcag    21120
atgtttaacc gactgagcca cccaggcaac cccagaacct tgttttctgt gtgtttctgt    21180
ttaaagacat cttatttaac agagttttg attcattaac attgagctga tggccaacaa    21240
cactgtaatt ccttcctgaa tgaagcttat ctagcacttg tatttctctc taaggcacat    21300
gacgtctctc taaggctgta gtagccagcc cttcatccct acacttgagg gccattttac    21360
cattttattt tattttttta aagattttat ttattcatga gagacacaca gagagaggca    21420
gagacacagg cagagggaga agcaggctcc ctgcggggag ccccatgcag gacttgatct    21480
caggaccccg ggatcacacc ctgagccaga ggcagacgct caactgctga gccacccagg    21540
catccccatt ttgccacttt aaacagtaga atcaccaaca gaaagcacaa aaatgcacaa    21600
actatagcac tcagtagact gtggaaagta ggacacttgc ttacagtatg aaagccaaaa    21660
caagaagggg tcacctttgt catcctcagc tagagatgtg catatgggga aacacaaagt    21720 tttgaacgc cttggaatgt ccatgggtaa cctcataaga accacgagta ttgattttgg    21780
aagatacaga cagattttag caggtcgatg aattcaaaat gtggaaactt tggataaaga    21840
ggatccataa atacactgga ttaaaccaat ccgagccagc catgtgaccct tgagttagtt    21900 gcattacctc tctgagcttc attttcctaa cctgtccctc tgcagggtgg tctttgagct    21960
tttcccaaca ctggaatcct gggaactggg tgggaattga acttctcctg gcctggcttt    22020
ctgtggatgg agggaccaca accccttttc tttcccggca ggtttgtgga cttccacgca    22080
gctgcctcca cctgctcgcc ctctcgggcc tccctgctca ccggccggct gggcctccgc    22140
aacggagtca cgcacaactt tgcggtcacc tctgtggggg gccttccgct caacgagacc    22200
accttggctg aggtgctgca gcaagccggc tacgtcacgg ggatgatagg taaccccgat    22260
gctccacagc ctgggatccc catctcccac aacacttctt gcagtgcctg cttcgtctct    22320
gtgtagcccc ggcatgcggc cacctcttct gctcctctct gcttgtcttt atttcttgct    22380
gcgtaaggtt ggaaagcttt tagctgtaag taactgaaaa cacctaacag ggaacgaaac    22440
catacatgga gatattttcc ttctattata acaaccttag aggtgagtga tggccttcgt    22500
tggctcggca gctcaagaaa tccatttcta tttctctgct ctgctatctg taggatggta    22560 gccttttgtcc tcatgcttgt tgctcttggt tgcaacagcg gggcttctgt accactcacc    22620
agaacctggc ttcacgggag gaaaaacagc ggggaggagg tgcgggcctc gtgtgttggc    22680
ttctacccgg aaagccaatc ttttctcaga ctcgccccac cttccctgca gaaagaaatg    22740
cacttaaagt cttattggtg ggtttgtgtg gccacgctcc gctgcaagga agcctgggag    22800
gccgggctca gggttgtact gatgggcttg gattggggca cgtgtctctg atcccctaac    22860
aaatccaaag ttctggtagc tggatgagtg ggggaggcat ggggggcaggt gaggcaagca    22920 gcagcacctg ccacacaggc cttttaggat ttttgtgggt ccctcttgct caacatttcc    22980
tacatgcgtg gcagcgggct aggttttttat ttgcatcagg gtacggagat gccttctgag    23040
atggtgattg gccccgtgac gagtgtaaga aagccgagct cggtgctgcc tagacgggag    23100
caggtgggtc caggcaggtg tgactgctct gatgcttggg cctcactgct gctcctccct    23160
ccggaggccg aggcaacgcg ccagtcccag cagcgtcctc gggctgcctg tgcttgttat    23220
tctgactttc agagagctgg gtcccgtggg ggttcctgcc tcgctctcca gtatgtgaag    23280
tggcaaggga ggctgtgcaa ccagcaggat ggcagcgcgg gtcccgggg gcagtgatcg    23340 gtgcctggag ctcccctgtt cacctgcagg aggctccagt tttgggtgtt gggcctgcct    23400
```

```
cctcctcttc tgggtcaagg agcccgacca actcctacag agtggagtgg ggcattcgtg   23460
gtcccagggg ggcaagcccc agtgggagga ggtataaatt aagatcctgc tttttcaatc   23520
cctttctggc catacccga ggtatcaggt atcgttactg tgaagcctcc ctgtgggctg    23580
agtcttctta gcggccccat ccccttgcatc cgagtcatgc tcataggcag gaagggtttg  23640
gcccttgggg ctcccgact ctaaagtttc atgaggcaac aggggactgg gatcttcctg    23700
agctgagctg gatctcactc acccttccct cttcatacct ttgaactcca agtgagcagc   23760
tgcttacata ttaaccgttc aggggctccg gtctcccctc actgctcatt ccacctttg    23820 caaattagag cgagaatagt caactacaac catgtgttga caagatgcac ttcctacaag   23880
catgcttatg ggaaaaaatc aaaacccctc caaaagaaca tcaagacctt tgccccacc   23940 cacacttcac ttctaacctc atccacggtc atgttttcac ctaggttgtt ttttttttaa   24000
gattttattt aatttattca tgagacacag agagagagag agagagagag gtagagacac   24060
aggcagaggg agaagcaggg tccatgcagg gagcccgatg caggactcaa tcccaggacc   24120
ccggggtcat gacctgagcc aaagacagat gctcaaccac tgaaccaccc aggtgtccca   24180 ttttaccta gttgaataca ccacttggtc ctccttttag cccctgccta ttgttttata    24240
tttctatgta atataatttt acatatttac aatagcttca aaaatttag aaataactta    24300 aacactttaa tataagttag ggtttccatg taatgcttag tccaaaccta tattacgttt   24360
ccaaacctac agagcagttg caaaaaggga acaataggca ctcacatgcc cttttcctag   24420
attccctgat tattacctt tgttacgtgt gtttgcctct aaaagatagc ttggtagtat    24480
tttgcccaga ccacgtgaaa taatttccgt agccatatgc ttcctcggtg gcccgtttct   24540 ttcttccct tgggtgtcat tcaatggccc tcttcaatc tttgcaccac attctttcct    24600 ttgcccttg cctcgtggtg gtttccctgg ggtcctcaga gcggagtag caggttgggg    24660 aattcaaaca aggccagggc ttctggcaca catcacacag tcattctccc ccctgaacaa   24720
acacatgcac agagcaagga gcagccgtgg gagtccaggt gagcatctct gcgctgggac   24780
agccctggga ggggggaggtg gtcttcggtc cggcctcctc gggctgctgc tggtggccag  24840
agaggaaggt gatggaacca ggagggaagt cggcatctcc tcggctgtcc ggggccccac   24900
gcttgttctg ggcctctgca ggtcccctgc acaggagggc agagcaggtg cgaagacgtg   24960
gggctgctgt gggcactgag ccctcttgta ggagcagaag ctcagcctgc tggctccttt   25020
gggcccccag taaaggcttg tcttccttt ctctgtgtgc gttcctgcgg aggtgctgag   25080
tcatccctgc ttgctttctg tgtcccctg gggtccctct gagtcccaga gagcaaggct   25140
tggctctcac acggcatttg cagggtctct gattgtcctc tgtcaagggc aacactgatg   25200
gaggagtgag tatgtgtgat cagcccccc aaggcactgg gagcccccgc ggggattcct   25260
ctgaacgtct ctctcttgct ttcctacagg caaatggcac ctcgggcacc atggccctta   25320 tcacccaac ttccgtggta agaattcttt ggggaacgt gttacctggg aaacagaaag    25380
caaagacctt ggtgggatag gactccaata atgttgaagc catcctgctc ctggggcaca   25440
tccctcctga gttagggcat cttcatctca gggtcactta ggagcatttg ggggaccag    25500 ggctcccgtt ggttgtctca cattcttctc tcctggcatc tttcttgccc ccgcccctc    25560 cttggtgcct gccagccctc tggctttctc atcgtgagcc catcaagtgt ccatatcttg   25620
agacacattt ggcacctgtg aggtccagat ctgtctagtg tgcaaagaaa tcaagcttgt   25680
ccagcgggtt cacagaagca ggccctaaat tcaaacagga gatgttccct cttgccttct   25740
tcctgcagct attcactgcc tcagactcct gattctctgg ccttggggat taggccagga   25800
```

```
tcaagctgcc tgagccaatt atctgaaaat cagtttgctg atcgatgact tctctgaatg   25860
tccaattccc caaattatta ttattattat tagtattatt ttaaagatta tttatttat    25920 tatttatgta ttcatgagag acacacacag agagagagag agagagaggc agagacacag   25980
gcagagggag aagcaggctc catgtaggga gccagacgtg ggactctatc ccgggtctcc   26040
aggatcacac cccggactga aggcggcgct aaaccgctga gccacagggg ctgccccaat   26100
tccccaaatt attgatggtt tttccaaagt tgtggtcacc tctgcgctcc tccctgaccc   26160
gcctcttcta tttcagatgg gaacccacag acgttctctt gcaagtgatt tatcgtgatc   26220
tcaacttctg aggcttctcc ctggttcctc cctggcacgt gcttcccagc tgctcttgct   26280
attttatcag caaatgggtg gccctttcct taaatgttct ctattttgca gactttcccc   26340
caagccccaa tatagctcca tgggaagagg ctgcagtgct ctcccctaga cctgaggaac   26400
tgtttgcatc tgaagatttt tgcatttcaa tggcttctag agaaccagcc ttcagccttg   26460
ggctgcaacc agccttcagc cttgggctcc cattggccaa caccttgtcc aactcctttc   26520 tccctctgg ggctccctcc aaccccctgt cttcccttgt gccctgtttt tcagttgggc    26580
ttccatggca tcttccacat atgcttttta aagagtgaca ggtgaaggaa gtgaagactt   26640
ggcttttcca ctaaaaatga ccacagaccc tattttccc gcatggtgtt gcttcctcct    26700
tgacaaatga ggaggttgaa ctagattgag gtgttgacaa tttgagtcaa ctggagtctg   26760
gtgctggggg gatggatcct gagactggat actgctcagc aggaagtggt gccattttgg   26820
atttgtggtg tctcccattg ggactgagaa gagagagcac ctgccataca tttgtatcct   26880
tggaccagat agtctcaaaa agtctcctgc cttgggcatt cagaggtttt cttgattcct   26940
atctctgagt tcacttgtgt cccctcctgc ttcttgtact cctttcctgg tgcactgtcc   27000
catactccat taccctcatc caaacctctt atagtttaat ctctatatat cttacttccc   27060
cttcaatccc ttgagggcag agtattttat tccttaaagt gccatgcatg tacttgattt   27120
tcatcaaata cttagtgagt gtgttcataa tcgccctggg gacggtaggt gtgcaatact   27180
tctctccact tcctcccact ctgggttaac tctaatccca agatgttttg caaatctagt   27240
cttacagcca gaacccagca aggtattttc tttgcatact acaaagggat attaatcaaa   27300
tcctctttta attacatact ccatagcact gcagtattaa atcatagaaa attaaatttt   27360
tgtcctaggt gtaagaatgc aggctcatag aacagaagcc aagtgggggt gctcaccagt   27420
tgcttctctt ccaggttttg attactactt tggaatccca tacagccatg atatgggctg   27480
cactgatacc ccgggctaca accacccctcc ttgtccagcg tgtccacggg gcgacagacc  27540
atcaaggtaa tcccatctaa ggaactggca gtgggctcca gagcaaggtg aagtcctaag   27600
ggtgtagtcc attaggagta aatgaggaag gtcacaggag acaattaagc cagtaaaaaa   27660
gagtatgttt agtgccaatt taaatgcatt atttgcatgg ggagtgagaa aacttttagc   27720
aaaggtgagg tcagcaaaag tattttattg gacttgtcca gtttcctggg atttttttagc  27780 tcagctggga agagcctggt gctgccatgg acttaccctg gtaaagcctc gctcccccctc  27840 tgcctgctag actactcatc tggcctagac accagacata cgagggatag agaaagggga   27900
agaacacaca cagggctgct tacaatctcc ccccactccc cgatcccct ggcaaagaag    27960 ccaacattcc agctctgaaa tgccatgcag tcactcaaca ggatgcttga acatcatatt   28020
ccatgagatg gggaaatcct caagccatac tagtaaggga aaaagcaga aacaaatca     28080 ttagcagtgt gatcttaact acctctgtat ccacaccttc acagccctac cgagtgggac   28140
tcaaaggaaa tcagccaaag tggtaactgg ctcactccct ctggttgtgg gtttcttttt   28200
```

```
tctttcttgt tgtattttcc aaatattcag gagtgagcag gtagtgcgtt tgttatagaa    28260
aaagatgcgg gaagccttgg gtggctcagc tgttgagcat ctgcctttgg ctcagggcct    28320
gatcccaaat tccctggatc gagtcctaca tcggtctcct tgcatggagc ctgcttctct    28380
ttcctctgcc tgtgtctctg cctctctctc tgtgcatgtc tctcatgaat aaattaaata    28440
aaatcttaaa aaaaaaaaa gatgctaaat tttattcagg taatagagtc acacaaacca    28500
ggtgccctgc ttgctcagcc catgctctgt gattgtttat aaggtcacag gtgtctgagc    28560
caccgaggga agacagtctc agctggctcc ttaataacac cacaatcgtt aatatagtaa    28620
tggccattta ttgagaaatt gttatagtct aggcactctg catgtttgtc tgcaatccac    28680
atgacctgac tgttgtataa ggcaggtatc tgacctgatt ttataagtga ggagcctgta    28740
aagggacagg tcaggatctg cttgcccagg tcaccctgca gctgtaatag gtggaggtaa    28800
tggctctggt ctgggtccct ctgagaccag agcccacgtg ctgctcaaag catgggtgct    28860
tgcctggcag cgtggccatc acctgggcgc ttgctagaag agcagcacgg aagatccccc    28920
aggcctcagg tctgcatttt caaaagatat gcaggtgata tttgtgtgca cgttgcggca    28980
ggagacgtga agccatagca catcttgctg ctgtccctac cacctgtggc ctgtacagca    29040
cacctgtggg cacacctgga catattgtgg catgacctat gtcagccagg tccctttaaa    29100
tccatgttaa atcaaacaga aaaaaaaaag cttgggttg gtgggggaa gaggtagaga    29160 ctgtgggtga tggcggagtt gccacaaagt cataacaacc tgaaaaactt gacactgacc    29220
gtgcggttgg cattatgatg cctagtacgg tgataatctt ttctcccttt ttcaaaaatt    29280
gtggtccttg gcgattattt atcccagtct gacctcgtgt cctaagcttt tataaagggg    29340
catgtgtgca tctaggtaca atgggggttt tcatgtcttt ccagtccttc cctgcaccat    29400
gaggacagtt tccttctctg agatgtctct tggtccccct tctctcccca tggttcgcag    29460
ctcctccccc cgtcctctgt ggcagccagg gctgagggcc tgagtgatga tggggttgct    29520
agtatgctgg gcagcatgca ggagcgccaa cactcactgt cttgttctgt cctttcaaga    29580
cctcatcaga ggtcacgggc actcgtcaca taaggagagt tggccctaag agcttaggta    29640
acttgctcac aggtctagct cacagctaga gtcattactc agccactcat gttggggcat    29700
tcactctcag gttcatctcc atctgtaaga ccaaggactg ggttttgtt tttgttttt    29760 ttgttttttt ccagaagata taactggctt gactcccact ttttctagtt gctaaagctt    29820
ctccaaattc tccaaacatg ctttgaaata tttaaaacta tccccagtca tctgtcttat    29880
tgtccaacgt catttcacgt gaagtcctga tggttgtcct aggaaagcac caagcattgt    29940
gccccattga cagaagtcat catttaggga ggtcggcgga aaatgccggg gatggggct    30000 attgatgggc tgtgggactc cgcttgagta atttagtttg tttggagctc agtttctctc    30060
ccaaccaaat gggagtaata atgtacgcag ctcacggaag tcttcgtgag cattgctgag    30120
tggccaggct tgtccgagga gcataaacat ctgttagaag gaaagggaag aagatatttt    30180
attggttttg tacttggagg aaatggcaga ctggaaaaat catctggggc cgggttatta    30240
aatgttttgt gttcacgttc atcgctgcat aaaagcgttt tgctctacac cgtggctact    30300
taggttgtgg aaataaatac cgtctgtggt ttccacacag aagccttgag agggactgtt    30360
acacggatgt ggcccttcct ctgtatgaaa acctcaacat cgtggagcag cccgtgaacc    30420
tgagcagcct ggcacacaaa tatgctgaga aagctatcca gttcatccag catgcaaggt    30480
aagagccccc tgcccccac cccgcacccc agggctgccc cctgctccca ccaccatgt    30540 cccctggcct cagcacccctt cccaacctcg gtggagttcc atcgcccaac agagatggat    30600
```

-continued

```
gcatgcatgt tcctataaa taaaactaga caacagtttc ccctggaatc tccaggcctg    30660
ggttcgaggc tcctctggta tgttcccaga gttctgggag cttccccctg ccctgctca    30720
gatcatgcac tattgtcatc atcgttttgt cctctcctct aagctcctgg acggtagggc    30780
ctgctgctgg atcctgggca ctcaagacgt ttgttgattc attaattggc aggatgtatt    30840
agcgttgtac tgctgctcta acaaacttat caccaactta tcagctaaaa caacagcagt    30900
ttattctccc acagatctgg agtttgtgtg tccaaaataa gtcttatggg gctaacatca    30960
aggtatcagc agggctatct ccttctggag cttccagggg agaaatgttt cttgcttctt    31020
ccatcttctg gtggctgctg gcatcccttg gcttagggcc acatcattct aatatctgtt    31080
tctattgccc ctttgccttc ttgtcttctg tagtcaaatc tccctctgcc tgtctctttt    31140
ttttttttaa ctttattttt ttatttattt atgatagtca cagagagaga gagagaggca    31200
gagacatagg cagaggaaga accaggctcc atgcaccggg agcctgacgt gggattcgat    31260
cctggatctc caggatcgcg ccctgggcca aggcaggcg ctaaacccgc tgcgccaccc    31320
agggttccct ctgcctctct cttttaagga cacttgtgat tatgttgaga gtcttccagg    31380
tgaatccgag atagtttccc tatctccaga accttaattc aattgcatct acagcatctc    31440
tcttgctata aaggtaaca ctcgcagatt ccagggatga gccccagata cctttgggga    31500
ccgttattca atgtaacaca cagggttttgc aaattctagc atctacaggg ccctggtagc    31560
ttacagaggg aagcaggctg agtgtcaggc tttagggagt ggtgggggct gtggtgaact    31620
tgaaagcaca ggcccccatct aagggaacag ctgctacctt gctctagctg cccgtggctt    31680
ctttagggga tgggagccaa gaccgtcaga tcctttatt tcataagaca cacaagatac    31740
ctggcccggg tgtgaaatct cctgatcttt aaatgttaga aatgactcat taaaaataac    31800
gaaaaccaaa aagcagaagc aggccacacc cctgggtgct catgcgcagg ctgtgggtg    31860
taagcatgtg atcatacacg gtcatcctgc ccctaccacc ttggccttgc tctgacccctt    31920
catagctgcc tttgctctgg cctctaatga gcctcagtgt gctcagctca tctttctccc    31980
tgggctgcaa actcctccag ggcagtagaa cagtttccag caggttcttt gctattccct    32040
atagccttag cctaagaggg cgagaaaaaa tgtgtcacat gcctgtttgc ttgtgcagaa    32100
ttaaaagggg actccacctg tggataactg agcgtattgg tctttaaatg tataagaatc    32160
cctcccaacc ccttgctcag ccgcagattt ttctagagag cagggcaaca ggcagagcag    32220
aggcagcgat ttattctcga taataaaaac tacttatggc ctaaatctgg ggaacagcct    32280
gttgggcttt caggggccgc attttttaag tgttttgggg ctctcagaaa cactggcctt    32340
ttttcacatg gctgagatga acaggcaag ccccttctcc catctggaga gctgaacaca    32400
tgtctgttcc ctggagcttc aggatggctc aggtccctgt gccctgtgac aggtggacgc    32460
ttcatggctg gtggggacag tctgcagtgt tttagacagc agagcactct cagaggagga    32520
gtgggagccc actgggatg ggggacggct tcaagctctc aagtgggcac agggctgttc    32580
atccaccagt taactaatca cttaccaggc agatgcatga ataatctcct tatcgtatga    32640
aaaaggtgaa gagtttgcta atttattaat tagctatttt taaaaatat tttatttact    32700
tattcatgaa agacacacac agagagaggc agagacacag gcagagggag aagcagcctc    32760
catggaggga gcctgacgtg ggactcgatc ccaggtctcc agattcaagc cctgggccga    32820
aggcagacgc tcaaccactg agctacccgg gcgtccctat taattagcta ttaagtgaag    32880
agtcacatga atcccttggg tgtgctgatt tctttaggat ttgacttgcc aattcatcca    32940
tgattttttgg agcatcagca agaaaggtcc ccagatctgt actcctcctc tgtgacgctt    33000
```

```
gcccccgggg ccaggccctc cctaacctgg gcccgtttgt cagaactatg ggaagtctcc    33060
agagtggggt ttcctgctcc tccttggcaa gaggcttctt tgaaaatttc tactctctta    33120
gatctttagt cgaatgcaga ctcctgccta gcagcgtgcc caaagctaac cccggatctg    33180
ggtgttttaa acagcaggcg tagctcttac ctggcaaaaa aggagaaagc agatgtcatg    33240
ggctcctggg tcatggagct gccagtcccg tgtgcatccc agggtctggg atgatggcac    33300
gctgagcccg aatatgaaat acggggcctg acaagggtga gggtgctggg ctcaggcctg    33360
agcaatagct tagggtactt gaagtcagag tgcgtggtag gcgaggcaga gtgttcatca    33420
ctcagaacaa ggtcccgggg ggacacctgg gtggctcagc ggtttggcac ctgccttcga    33480
cccagggtgt gatcctggag accccggatt gagtcccatg tcaggctccc tgaatggggc    33540
ctgcttctct ctttctgcct ctctctctgt atctctcatg aataaataaa taaaatctta    33600
aaaaaaaaaa aaaaaagaa caaggtcccg gggatacaca ggtgccaaac gagccctctc    33660 cacccccacct gtctgggctg gagccaagaa gccgtgtcaa ggctttgatt ccctccctca    33720
cttgactcga ccccacccca gcattgccgt ctccctgctg gtctgcccct cacctgtacc    33780
caccaacctg cccctgaat cagggctctg cgttcgacta tgagctcatg ccctccccc    33840 ccccaaccca tgctttcctc tctctcctgt ggaaatagtc cgatgaatac agagtgagga    33900
aaagaaggag ctaagggata gtgggacctg gagtcttgct ctcctgcagc ttctccctgg    33960
ccctgttgca cctgctccag cggccaccag cacagcccac ctgtagcccc ccatctgtag    34020
gcttcaaagt cttaaggatc tcttgcctta ccccaaagcc agctcagttc ccccattaca    34080
ctgtcccaca gcgccctata tatagttctt ctccatcact cctactaatt tgcaaataat    34140
tatcggatta cttttttagt tgcattttcc cctcctgttt ccaattagat gtgaagctcc    34200
aagaagttga aaatcatctc tatcatgttc cttgctctgt gcccactgcc tgagggctag    34260
ttagagctta ataaatattc cttgagtgag tgagtgactt tatcttgccc tgaaggcgtg    34320
caggtgttgt gctagggata caaacgtgaa ttagatctgt ccttgctttt gagtggctcc    34380
caggctggtg gagaaacaga tttgtgggaa gctggtgtta acagtgtgta ttatcaatac    34440
tgatgagtac ggtgagggag gggagcagga caccatccgt gacctgggag cacaggaggc    34500
atgttggtgg cttagagctg gatcttaagc actgagtaag tatttatagg caggatacca    34560
gggaggtgac tgccaggaga ggaatagcat gaccagggca caggaaggca gaaggtgagg    34620
cgtttgggaa gctggcatgt atagagaggg tctctgagag gaaggagggg aaggctggaa    34680
gggacccagg ctgggaatgg ccttgaatgc tgggctgctg ggttgggggcc aacccagagg   34740 gctatagtcg agctcctccc atgtgcttct aaagaggaac tgggttcaca actgggtttg    34800
agagcactgt ctgtaacact gaagcccga gaaacatgga gaaatgtggg ggcaagccat    34860
tccagagaca cccctttatcc agagccagaa accaaccagg cagatgccta gccctccttg    34920 ctaccccgg ccggtctggc tctctggcca gacgcccact gggggccttt catgacaggt    34980 gggtgcccc cacccaccac tttctatttc cgatcagatt attattttg aaaaagattg    35040 tatttattta ttcatgagag acacacagag agaggcagag acacaggcag agggagatgt    35100
aggctccctg cggggagccc gaagcgggac tcgatcccag gaccccggga gcacgacctg    35160
agctgaaggt caaccactga gccacccagg cgcctctcac atgatttatt taattgcatt    35220 tatatcatttt aatctttaat catggccgta tctaacaact ggtttgcaaa attcctggag    35280
ttggggcgtg cctttatggta tctacctgtt agaaaaaagc accccctctg ggtgctgct    35340 gatccctgct ggagcaccca ggttggccag ggcactgcag ggctggaatt aggcatctat    35400
```

```
tcatcgtctc ggcgggacgt cctggtgcag gacacaactt atacaactgt actttatcgt   35460
ccccagacac taagtcagca ctacccaatg gaactcttca caaggatgag aatgttctct   35520
atctgtgctg tccaagatgg tagccaccgg ccacctgtgg ctactgagca tctgacagag   35580
tcggcttggg caaccgaaac atacaatttt aatatatgtg tatagtgata aatatacata   35640
acagaatatt tcccttccta atcgtacatt tcggtggcat taaatacatt cacgttgtta   35700
tacaaccatc accaccatcc atctgcagaa ctttttcat catcccaaac tgaagctctg   35760
tactcagtag acaccagttt gcccttcctt tcagtcccta gttcccatca ttctactttc   35820
tatctctatg aagttgacca ctcttggtac cttctctagg tagagtcata cagtatttgt   35880
cctttggcga ctggcttatt tcacttagca cagtgtcttc aagactcatc tgtgttgtag   35940
ctgctgagac actgaattct taattttact taattttcat tcactgaggg gtgcctgggt   36000
ggttcagtca gttaagcacc tgccttcgac tcgggtcatg atcccagggt cctgggattg   36060
agccccacat cgggctccct gcccagcagg aagtctgctt ctccctctct ctgctcatgc   36120
tctctctctc tctctctctg ttcctcctct caaataaata aataaaatct taacaaaatt   36180
ttttcattta ttgaaatcta agccacatac aagtcgtggc tgctgctttg gacaacgcag   36240
ccctggaaat attgcagaga aactgtcggt taagatgaag aggagtcccc tgtctcagga   36300
cttgtgttct gagttttatg cctgtcgaca ggcacagccc taatcaggga ggcccgggat   36360
cgggatgcaa gaggctctgc aaggtgtggt ttgaggcaga gctggggact ctcagagcta   36420
tggggtggtg taaattgggg taagctaaat aattgagagc cagcttgaaa atacaatcgt   36480
gggggagctg gtgtaaagcg agccatgctc cgatcacctc tctgtaccaa cttgatggtg   36540
ttgtcctttt gtccttaata catacccctga aagatgtgct cccccatagg tgtggtctgt   36600 ggatgggct ccatggaggt ccctgctgct tcaggagggg cgaggctgga attctgcggc   36660
tggctggatc ccgttcctta cctgggaatg gaggtggggg acagccagga agcagaggcc   36720
gcccaggctc cctccactcc caagagggga agcatcaggg tccagacggg ggcagccagc   36780
gcctgagcca ctaacagagc cttgacctag atgtttccag tactcatgtg tgtccctgga   36840
attgcctgtg gtcaacatga gtcattcatt catctcctag aaagggccga ggctgggaat   36900
ggatgtgacg acctggatgc cattaaagag cagatccggt tttaaaatat gtttgtactg   36960
gattctagag tgtggcattt aggagccaag gctttgctgt cagctgtggc atttaggagc   37020
caaggctttg ctgtcagcca gatgagagtt ttaatccaga tcgtatcact tactagttag   37080
gtagccgtag acaagtcctt tttgtctccc tgggcctctg atgcttcatc tgggaaagga   37140
actggagggt tattgtgagg gtgaaaatag gcagcacgaa tcgggtttca taagctctca   37200
gccaataata aaggacagtg acaattatta cgatgactcc cagtttgtaa ctggctgacc   37260
cggtgacctc cacgttccct tggaaggttg tagacctgtg tgtattcctg aacacgtggg   37320
gcagaaggtg ttctgggact tttctctgag gcaaaggaga gccacggaga caatggacga   37380
gccagcaggg ccttccggag agttacctct tggctttccc attgcagcgc cagcggaagg   37440
cccttcctgc tgtacatggg cctggctcac atgcacgtgc ccatatccag gacccagctc   37500
tcagcagtcc tacggggtcg aaggccatac ggtgcaggtc tccgggagat ggacagcctg   37560
gtgggccaga tcaaggacaa agttgaccgc acagccaaag agaacacatt cctctggttc   37620
acaggtgaag tagtaaaacc cagctagctc cctgagatct aatggataac cctgcccatg   37680
cccccttgga agagcagaat ctggctaagg gatcctcttt cacagggcag gggcctggct   37740
ttgaacttgg cgtcctgcta gtgtttgttg gcctgagtgc tgagcacctg tccactgggg   37800
```

```
cctccgaggc tgagcccctg gaaaagtttg tgcagagagc aaggtaccct gctggcctct    37860
tccgtattgg tttagggcca tctgggtagt gactttgaca ttgcaaatcc gtgtagtcct    37920
tgggtggttc tgaggttccc tcctcaccat cgtcccagtc ccagagacgc cagctgccac    37980
cggtggtcac accttttggc cgagtgcgct gaactagtga gctgtttaaa gggcctacgc    38040
aggcattgtg ggtcctgggt gccttttctgg aattgggggg agtggtggtt ggaagcgctg    38100
ctctcggggc aggcagagac ctgggtttga aactgctcag aacttggaaa aggcacttta    38160
ccttctctga gccggtttcc tcacgtgcaa aactgagctc acaccagcat ctactgctta    38220
gcgtgttgga cgatcctgag atcctgtaag ggaggcgctg ggtgcgtcag gctctcagga    38280
aagagctgca gggctgagga tagtaaaagc aaaggagaag gtaaaagcat ctgagacaag    38340
aggctcgctc gccctgggc tcacctgggc cagggaaagc ccacctcttg gaagcccagc    38400
ctcatagaac aagtcattct tcgggggcag ggatcatgtt tatttttaca gcttcttctc    38460
cttcccagcg ccctgctctg cacggagatg tgggaccagg gagggagcat cggcaaaagt    38520
gtccacaggc cagttgatcg ctacctgttg cttctttttgg tttccaggag acaatggccc    38580
gtgggctcag aagtgtgagc tggcaggtag cgtgggtccc ttcactggat tgtggcaaac    38640
tcatcaaggt aggggctcaa ctgggggttgg tgcatcccac tgggggatgct gagcccaggt    38700 agggctgtgg ggtctgtctc ggggaggatc aactcatacg caggcttctt ggccatcatc    38760
atgatagtca aagttgctca ccagccacca gctcccaggg aaggaataaa ctgagagatg    38820
agagtttcta ttaagcttgg acccaccccct ttctctcctt ctatctccta ccgcccccgg    38880
gctccctcag ggcatgaact ctgagtccag gaaccttcca acaaatacac tttaccttga    38940
catttatccc actgccttta ctcatcctcc ttcttttctt ttctttcctt tttattttttt    39000 ttcactcatc cctccctcca tccaaccatg aattcattcc attcatttag gagacattca    39060
gggcataata cacaaggttt tgatatacat aatccctaaa ccttacaacg ttggaaagta    39120
ggtagtagcg cctctgtttg cagatgaagg agagcctcag agacatgtgc tcggggacct    39180
caccttctaa cacagctact gccctgggga caatctggca gaaaggacca aaggcttgga    39240
acacaggccg gtggatgcat cagttcttcc ggattagcca agtgcaaatg ctgtatgtga    39300
aaggatgctc attgcatggt ttttaaata tttttttaag attttattta tctattcatg    39360
agagacacac agaggcagag acataggcag agggagaagc aggttccctg aggggaaccc    39420
aatgtgggac tcaaccccca aaccccgaga tcacgcagtg agctgaaggc agatgctcaa    39480
ccactgagcc gcccaggtgc cccacatagt ttttaacaaa caaaccaaaa aaaccaagaa    39540
gttgggtatt acccaaggat ccagcaagag aggagtgctt aaggaaatgg tgacatgcac    39600
atttaaggaa attctaagga actgctgaaa tgatgcatat tattaacctg gaaacattca    39660
tcttaaatac tttttcagtga ataaagcagg ttacagagcg atatataaag tatgatctta    39720
ttctatgaaa ataagctacc aattctcaga aaaatcttga gagagttatg ggcagttgat    39780
aaaacatgag aggtggttac ctttggggag gggaaggagg atctaaatgt gattttttt    39840 ttttcctcac aacaacctgg tcttatttgt gtcctacaag attaaaataa aattctggaa    39900
ggtgcttata tccaagggggt tcagaggtgg gcttgggggg atcaccccct ccctgggctg    39960
ggctttccct actgaccagc tcctgagcta tggcattcac tgtctccagg tcagaggaca    40020
cagactgttt ttcctattag tctggcagtt acctagaaag tagaacttttt gtgcatctca    40080 cggttgggga cgagaaggaa gtgctgatgc ttcattttttt ttttgtcacc tttaacctgg    40140
tgtctgttca gatctcttga gaacttcaca agtgggtggc tgcccttgac tatagccagg    40200
```

```
tgctgtgcct ggagattcca gctggggatc aggagaactg ggggccgcct cccccctgac   40260
ctgcttggtg accagtgggc ttcatcggtc agggtgttgt gtctctctat acgtattgat   40320
ctctttgact agtcccgttc gggaatgttc tctggaaaaa cgagcagaca aaggtgcccg   40380
gactgggggt agagagatac agtgggagct ggagtagtt ttgcattagc tgatcctcct   40440 ctccataccct gggatacct cagaccaggc tactggccct aatgctcagt tggaaagcct   40500
gaaggagcct ggaattggaa ctctccagtg taaaattcca gaaagctatg agaccttgg   40560 atgggtctc catgtaccag taagtggctc tgtagatagc cctctgttcc ctaagaaggt   40620
gacctctgat ctcctatcta gaccagcctt atcttgtctc tctccccttt atgcagtttt   40680
tgaaatcacg aattaggttt tgtgatgggg agtggggtcc tgttctgtga ggggagtact   40740
ttgccctgtg agaaacagaa ttatgagggc cgcctgggtg gctcagtcag ttaagagtct   40800
ggctcttggt ttccgctcag acgtgatct cagggttggg ggatggagcc ccacgtaagg   40860
cttggtgctc agcatggatt ctgcttggga ttctctcttt tcccacctgc ccctcccct   40920 gccttctttc aaataaataa ataaaatctt taaaaaaaaa acaaacaaac aattagggc   40980 acctggtggc tcagtggttg agcgtctgcc tctggctcag gtcgtgatcc cggggtcctg   41040
ggatcaagtc ccacatctgg ctccccacag ggagcctact tttccctctg cctatgtctc   41100
tgcctctttc tctgtatctc tcatgaataa acaaataaaa tcttaaaaaa aaaacaccc   41160 acaattatga tgagctgggc agcctccact tctcctttcc ttggtttgac cttcaggcat   41220
ttgttgagca cctactctgt gccagcaagt ggggatgcaa agatcaacaa agccccaggc   41280
tttatggagt gactgtctag agcagtgttt ctcagatttt atttttttta aagattttat   41340
ttatttatta cggggagaga gagagtgcac acacataagc agaggggag ggacagaagg   41400 agaaacagac ttctgataag caggaagcct gactccaggc tcgatcccag gaccctgaga   41460
tcatgacctg agctgaaggc agacacttaa tcagctgagc caccctaggtg ttcctgtttc   41520 tcagattttta ttaattaatt aattaattta tttatttatt tattttttgtt gttgttattg   41580 ttgttgttgt tgttttctcag attttaacat gcagacagtc ctctgggat cctctagttc   41640 agactcagta gttctgggat aaccatgagc atgttgcatt tctaacaggc tcctaggtga   41700
cactgaaatg tttggtccag gaatcactcc tagaaccacc aactagaata tccacgtgga   41760
aaccatatga atctagaact ttcagatgga gaccagaagt taccaagcta tggccttgga   41820
ctggcaacag taacgctacc tgagaacttg ttagaagtgc aaattctagg gcctcacccc   41880
agacctgctg agtcacaaac tctggggagg gaccctggct acctgtgttt taccttgtcc   41940
ttcagatgat ttttggtgca ggttaaaatc tgggtgccac ctgtcgagag ctaccctgtc   42000
tcgtacacct ggcgcctgg ccacgctgca agggcccaga agccacatat ggctggtggc   42060
taccatagtg gacagtgtga acagagacca tttccatcac tgcaggcagt tctgttggac   42120
tgtgctggga gcctccactt cagcaggaga ttgtaatatg ggtaaggact ccatgataaa   42180
gaggagcacg aggacatctc atccacatga gaaagacaca ggaaggcttc ctggggttgt   42240
ttgagttttg aagaatgagt aggccacagc tagggatgtg caggggaggg gttcgtgagc   42300
agccccggga agcggcggga agagcacagc acaggagctg cctagttgtg tgtgtgtcca   42360
gagctcgtag aagtgggtcg tgtaggggaa ggcgaggcag gagtgagagc cggggctggt   42420
ggtcaagggt cttttgtttc agacagacca tttaggcctt gattctaaag aaacatggat   42480
tcgtggaaac gttttatgaa taaaggcgac attttttcgat tttttatttg aagtgagatt   42540
ctgggacaga agatggaccc tcttagtgtg tacaactcac tggcattgag cacattcact   42600
```

```
gcagagcccc cagacatctc cccgcccag agaaaaccac ataccccctaa acacttgcct   42660 cccatctctc actcttttctg gcctcttgct caatttttaag acatccctct taggttggtg   42720
gggctgaggg cagagagagg gacaaggcta gacccgtttc catcaagccc tgggtgataa   42780
atgaggacag caggtgactg aatccccagc aatatccctg cactcaaaga atgccagggt   42840
aggaggacac ctccgcgatc tttgttccaa ccaccctgtt ggccacacga ggaaactgag   42900
gtggagcagg gcggagggct ttctgaggcc agccattggc caaggggggcc ttgtcatctg   42960 accccccacca gctcataacc caacctacac catggctgta gtcacacctt gttctactcg   43020
gctaactgct cagccgtctg gaaaatcctg tgttgcttct ttggacttca cggttgtcaa   43080
gaaaaatgtc tttggctccc ataacagtgt gaatctttct aaatctgcag gagtctgagt   43140
ggagaggtgg agggagctca tggctttgga agccccaatg gggctccaat ctcaaccccca   43200 cttacaaatc ggtgcccacc gggcccctcc cctggacagc ccagtttcct ccctctgtaa   43260
ggtaggactg tagacccccac ttgctggatg gatgggagca tcagatgggg tgctgcccac   43320
catcatcaga tgggggcacc cagccttgtg cgtgtcctct actaaccccc atgattctct   43380
gcgtcttcat tccagctga gtcaactggt tggtgttaat taagctaaac tggtcagtat   43440
tagtgtctag ccctaccgaa ggctgcgggc aacttaaata acatacggag gacttccaa   43500 gtgtttggag cctcagtctt ggaaacttttg ttctgaagct ggatttcagt cttctcattt   43560
catactctgg cgaatctgga tcttttttact tggaacacat gttttacaat acgtgtacgt   43620
cgggggtcac cgcagtgcct ttggcaccaa gtccggttca ttgtgggata gtctgttaac   43680
agtcgtcggg aaagccaaac cggttggtat tactgtctgg ccctcccaga aatagctagt   43740
agcatctgag gatgaaaaat gaatgaagta tctccaggaa acagtctggc ttaactattt   43800
ttgaaaatat aacttttccc cctctcagct gctctagatg ttgctttaca cggaaacgga   43860
aaatgggatt tttcacagct acagcatgtg tgcgtgtttc atctgatcca gcagagccaa   43920
actattcata tcgaataaaa ttataatatt aatcacttaa aaaagagaga gagagagaga   43980
gagagagaac actctttctc taggagcgag gcagatacac ctgtggcttc ctgtggtgcc   44040
agtggggcaa ggagctgagt tctcagtggg gtggggggccg gatgccatgc tcttcttttc   44100
tcaggaaagc ctgaaggtga acttggccta gggggtgaac acttcccctt cctcattctc   44160
caaaccggct tccatttggg gctccccac agccctcctc ctcctctctg ctcaaagcac   44220
cgcttggtgg gggggtggct ctggaaagtc aggctgagcc tgcgtggcag gagctgtgtg   44280
ccagggctca ggtcacggga gggaggctgg gggtccctct ggaccgcctg ctcctcctcg   44340
tccaggttcc tcttcagtgg gatgccttca catcctgctg taaggggccc gggtcttgag   44400
agcagatgaa agggagaagg cagtcagtgt tttcgcaacg gagtaggaca aacagtaccc   44460
agagccctgc ttctttctcc ccgcagccag cccgctacgt caggccacgc gctgccttcc   44520
cctgttcccg ggccccagg ccccctcct cgtcttccct ttcctttcct ggccaagccg   44580
ccttgctcag ctgatgggat gaggcagcgt ctcctggagt catctctgca ccctgtgcag   44640
gagtgaggat gctcctctgg gcttggcctg caccccctgca gggatgaaga gaaactgaac   44700
gcgggtggag ggggtgctgg gcccgagcag agcagagtgc ccctgctttc tcccaaagag   44760
gacccgcggg tgcctgcccc ctgctgcccc agcgtggccc tggccccggag cagcaggccc   44820 tcccttcccc actccagacc tatttcctac ccgggacaca accagcagct tgtttgcccc   44880
ctaaccgact gctcctctgt ctggaaaatc tttccttgtt ttatttgaag agcagaactg   44940
ttccttcctc ccccttggtg atgaggaaac attctgttga atttggcatc ctcagcttct   45000
```

```
aggagacctt ggttgtttgt aatttgatgc tatcaggttg ttgcgtaagc tttcccactg    45060
ggaagcggct ccgcatcctg ggccttctgt tccgcttggg gcaggggtg gggtggagag     45120 aggtcagagg tggggctggg tgagggagag ggagagcgga caagagatgt tggctgttgg    45180
ccctgctggg gggcagggcc agctggttgg gggacccagt ggaagtcaaa ttgtgtctcc    45240
ttccgggacg ttggccaccc ggcttggaat gtccccatca ccccgctcaa ggccaccca    45300 ggccagccag agtcctccat ccaaacagag gcccgtctgc cctgtgtttc tagaaaacta    45360
gtatgctgcg ggtatccttg gcaaggacac gtatttatat ttagaaacaa aggctgcttc    45420
tttagaaggt tagagaatgc acactcctcg ggacaggcgt gtcccacctg agtcacaaat    45480
acaaacgcca ggcaggtaat gtggacgagc aaatgtttgt tttcctaagt ggtgggcagc    45540
acgttagagg ttcagtagac tgcagagagg gccccgtcta atgacattca gaattagttc    45600
agaaaatccc gttcgtgcca aacccaactg tcagagggct gaattcagcg tgtgagctgc    45660
cagcttgcaa cttctgctgt ttaccctccg taggttgttt cgttttttgtt tgtttgtttg    45720 ttgagcttct ttggacggcg gcgtctgtca ggcacttcct gcaggtgctg tgcagggga    45780 ccttgctttg gagcttgata cacatgatct tctgtggctt tgcccacctc ccccgtgaga    45840
taggcacaat catctttcc ccctcagagc tgagggaggg taagaatcct gcccaaggcc    45900
acatgtcgag aatggccctg gatgtagaac ccgggcctgc tggactccag aggcatcctc    45960
cctcccatct tgctaatatt cctcaaactc tgctcctcag gccactggca tcggaatcag    46020
ctggcatcag aaccccactc taggcttatt aagtcagaat cgcttggggg ggggtcttct    46080
ggtggttctc ttgtattgag cgagcccctt cctttagccg ggctgccctt gtgactcagt    46140
gacgtcgagt aggccgcgag gggaaagacc tccacttcca ggcgcgggcg gtggcgggga    46200
gtcgtgcccg gcctccccgt ctgccctgca tcacggaatg ccacttcact tccgcagcca    46260
ggggaggaca agtaagcaaa ttcatgaatc atggttctgt ttatgttttg gttgctgagg    46320
ctaaatattt atggctttaa gtaagaggtt ctgccttaat gagagtcata actaaccacg    46380
agcgcactaa aatgtgttct cacgaccata agacgtgcat ttctccaaag agagccagat    46440
gtaacgggca ctttgaatgg gctggtgcca ctgatcaaag tctgaaggtt tatctaaact    46500
ggccaatagc tttcgaaatc caaaagtgca cacgagttcg atggatgggc ttcgccatta    46560 ggttactga gagtaacagg tttacattta cgatcctatg gcataaaggt gtaaggtgt     46620 gggcaatatg aaacacacgc ttaaaagcg ggtaagccac atttaatttt tttttaaga    46680 ttttatttag ttattcatga gagacagaga gagagagagg cagagacaca ggcagaggga    46740
gaagcaggct cctcacaggg aacccaatgt gggactcgac cccggaacct cggggatcac    46800
gacctgagcc aaaggcagat gctcaactgc tgagcccgc aggcatccca agccacctt     46860 gattttgaaa cgcactgtgt ccacttcctg attttgcccc ttgctcttgt cctagatgga    46920
cgttctccca tcttcagata ttaactattt ttagatattt accttagaa gatagcaatg    46980 tccaggtacc atcccaggca aatgaaccta aaattctgg gaaggaaac ttggcctggg      47040 tattttttaa aagctcccct agtcgggggg cacttgatgg gatgagcact gggtgttatg    47100
ctatatgttg gcaagttgaa ctccaataaa aaaaatttt tttaaagtaa ataaaaaatt    47160 catttgaaa tgaaaacaaa caaacaaaaa ctccccttgt catcctaata tacattcagg    47220
gatgggtggg agccactgtg ctagaagctt tgatgggtca ggggctggct atgtagttag    47280
acttggatgc aaatcctggc cctggcgttt gctagctgtg tgacctttga caaattggtt    47340
aatctctctg agcctcggtg tcttcgtctc aaaaatgggg ataatagtgc ctagtttgca    47400
```

```
aggttgtcag taggattaaa tgggataatg cagggaagca cttagcgtca tgcttcgagg   47460
tactttaact tggtgcatag ggaaggctca acaaatacga gatattgtgg ttactgtggt   47520
tattacattt agctcagaat gagtttcctt tcgtatcatt gcagagtatt gggggggcagg   47580 cgctcagcct tagctgtgca gataaactga aggaaacact gttagatgtt tctgaaattc   47640
agactccaca actctgggca ccccacagag gatgccagtg ggatcttttt aagtttgtcc   47700
actatgcagt cagccaatga gatactggga tttagagcaa gacaattcca tgctaagggg   47760
gatttaagaa aaaaaatgta aatttgcaat taacacacca tgttatgtta gtctcaggtg   47820
tacaatgtaa taattcaaca agggagattt actttctttt ttaaaggatt ttatttattc   47880
atgagagaca cagagagaga gaaagaggca gagacacagg cagagcgaga agcaggctcc   47940
atgcggggag cccaatgcag gactcgatcc caggaccccc aggatcacga cctgagctga   48000
aggcagccgc tcaaccactg agccacccag gcatcccagg ggaatctttt ttttataatt   48060
gcttactcat tctctggact cctttaagat aaattctgct acagtaggaa gtctgtgggc   48120
ctggctggaa tatgtaattg tgtctttctg ttaaagccag aagccagggt gcagccggcg   48180
ctggctggct ggtcttgacg acacagagtg gggatcgctc ctcaagtggt catactgggg   48240
ggcttctccc agccatcctc ttcctcctgg ctccagaacc tctccatgtg ggctctccac   48300
tgcactgaca cacatacttt ttataactgg ctggattcct tcgaatccct ccagcttcc    48360 acccgctgct gaaataaggc aaacgtattg aacaattttt ttctctgaga accaaattag   48420
gaggatcagt tgcctgaaaa agagccacac aaaaggtggt gggggacaag cagagcccct   48480
cgtggtgaag atcaaccagc aaatgtatta atggggagct agtatgttct tctgaaaaca   48540
tgctgggggc agagaccaag cctggtaccc atgcccacct ccgggtaggc ccttggctcc   48600
tgccttcccg ttggctgtcg gaattctggg cttgcctctc agcactgggg gcttcactgg   48660
tccttagcat ctggcctcaa agactaagcc aatctgtttg aattttgtgc agtgtggata   48720
tgcaaagaaa caggctccat gctttcaccc acctgtcccc ccaggcttcc atacagatgt   48780
ccctccccgg ggagggggaat tatctgcaga gctctagcac gtgcagttgg gatgcttcct   48840
ctctgctctt tggccttgag ctgcagcttg agttatgcat tccaaggcca cgtgggagtg   48900
catttcaggc ttgccgcagc tctggattct gttccatgtg cgtgaaaaat tgagagtggg   48960
ctccgaacgc atttctggga ggtgtggctt tcgacaaacg agcaaagagc ttcccgcttt   49020
gcctgccgaa ctccacttgg ttttgagagt cccacacccc tgagcataaa cagtccatag   49080
atgtgagttg ttttatgttt tgtttcttac ttcaacactt gggggactcc aaagctggtt   49140
aggagaaaat cccaagaatg ctgagcattt ccggtgggac gtgctgggcc ggggacatta   49200
gaggttctgt ttgctgcagt gtgagtgcag agcgacagac gccctggtct tgtagccccc   49260
tcctgcccat catcgccgct ttcatagcca tgccagccaa acatggggag gttgcatgac   49320
cacgatatgt gtgagccaca tacagcgtct gccttggaag ggctttctac acgctaactt   49380
tgtggaatcc ttggctcagt gggatgaggg tggggtgtgt gtgggagtgg tgggatggtc   49440
atggctaatt caacgctaca tgaattcagg atgtttccat aaaacatgac ctcatctctt   49500
ccagcccgct ggtcatcgtt agactggtgg tcacttttga gtagtggtta tgaaaataat   49560
tccttttaat taccaaagtg gaaattcata gattgcacat agattgttct taccccaccc   49620
acccaccccc aaagccccccc aagaggcaag aggtcggagc tattactaat gctgtctcta   49680
cgacatgaga acaactcatt aagtcaaaga aaaacaaagc gaagcgaagc aaacagaaat   49740
acaacaataa aatccatgcc aggtcagttg ttgggcgttg aacagatcaa atagctgggg   49800
```

```
gagtttctgc ctttctgtct tttcaaataa ttgtaaatat gtgtgtatat atatatatat   49860
atatatatat atatatatat atatatattt agcctaaaca gtcatatgag cagtcggaag   49920
acaaagtcct ttttattcaa cgtatttgtt aaatacctac cattcctggt tgtaggagac   49980
tgatggagtc tcctggtgtg gagatgacac catcagcgag tcaatgaaca aacctcagac   50040
aattaaaagt gttaaaagta tcatgaagaa aataaagtga cctggttcca cagagagtga   50100
cagcagcacc tgtttatcta tgttaatcc aggaaaataa aagcacagaa tgcaagatgt    50160
tagctagagg agtaaaaata gctggttact aaagaagtca tccgttggtt ggagggatcg   50220
gaagctctca gggtgccttt agaaaaggcc cgtggtgcta gagacctgac tgcatgtgtc   50280
ctgtcgcagg gggcagtcca gccaagcaga ccacctggga aggaggccac cgcgtcccgg   50340
ctctggctta ctggcctggg agagttcccg tcaatgtcac cagcactgcc ctgttaaggt   50400
atgagaccca aactatcttg aaatgttggg attcagagca agaaaatcat gaatcgacgc   50460
tttaatggcc aaaaacccca agaagagaga ccccttcgg ccacctgccc tggccaggtg     50520
ttcccaggta cctgtcctac ttacagcaag agtggctctt tcccagccat cctctggggg   50580
tcatgttgga gtgaagaggg gcctgggtgg gtttcatggc ctcgacgtgg agacaggacg   50640
gtgtctgctg acgctgcggt ggcagagaag ttagcagcag catctcccct tttggtctgg   50700
gctcagctga cgggagagaa tagaccattg aagccataat tattccatcc tcggggtga    50760 gggcaggtgg cctcaggatg cctgtgtgaa gccagcttat catcagcaat cacatgggcc   50820
caataaagga atctaggtgt ccccctgccc tggaggggag ggagaggagg tggccccaat   50880
gggctgacca ggaaagaatg aaccctaggt gaggacatgc ctacctgtgg ccttgaagcc   50940
tccctttcag tgaggtgagc tgatgggctg ccccctttac tagaaggatg actctaaaat   51000
gtgataatat cccacccccc gactcttatc ttgttatctt aaggcagatc caggaggccg   51060
tctcctcggc acagcacgtg gtgtggtgtg ccattctcag ggcacttgca tgcagctctc   51120
tgtatgaccc agtcttacga tgggaacttg tcactcactc cgttgggac ttcctctctg     51180 tggttctgct cttgtactca ctgacaaggg ggactgggtg ctactcttgt gctcagagct   51240
tttgggctgg ttagagacga atgtgttagt tccacaggct ctctcatcag ccgaatgagt   51300
tgtagcctaa agaacccagc ctcacagagg aaaacaagac tcctgggctc cttccagcat   51360
ccccagacct ggtggggagc agggaggaag gctggagccc aggcgaaggt aaacagctct   51420
gatggccaga ggcgggtggg taggcactgt ccctggcagc ccggggtggg ggtggggta    51480 cgggggggcag gccccagggc tcggctcagc cctgcccaat acagtcagga gggggcagcg   51540
tgttgtcagg ggggtgccag caggtgtgac aacaacagcg tgggctggag tccgtgatgt   51600
caggctggcc gggaagaggg ccagatgggc tgcttttat ggggctgact tggtgcagtc     51660
gggccaagtg ttcacaggct gggccgcaca tgcacaaata actgggcaat ctctcaagtt   51720
ccagccccaa aaaccgagcg cgtgcttctc atctgagaag gctgtttgca cccacagtcg   51780
gccgtcgcag cagcagtgca ataacattgc tccattaatg atttaaggcc tctgaggggg   51840
cacctatctt agggatata gccaggtggc tgaaaaaagg tgagtcttgg tacaagataa     51900
cgtctgcttg agggcccctg gagtttcgcc aggacaatac caatgtcacc ccatcagctc   51960
cccgtaacat gttttttgtt gttgtttgt ttgtttgttt gtttgttttt ggtgcgaaag     52020
tagactcaac tgtagcagga aagtttgtgt ccatagaatt cacctcctag ctgttgcccc   52080
acatgaatcg atccacgtat agcaagctgg ggtggagtgt ccttactgcc aggacaggcc   52140
actgtgtctc tgctgctctt ttccgtgact cctgcaggct cagctctaag gaggatagcc   52200
```

```
tcatgatccg tttttaataa accaaggaga ctgcttcatg tccttgggag cccagccagg    52260
ctctcccacc cagggtgctt atcacctttg ccagcacttt attcctcgga tggatataga    52320
tcttcttcta gaacagagat aactcccctg aaccattcag agctaagccc ttacacctca    52380
attctggtgg ccctgagaag tcacgggaag agagtagaca gcttgatata gatacgtgaa    52440
tacacaaacg taacaagtgt gttgggggga ggggatagc aagggaagag ggatccacac     52500
tgactccatt ggttcccttt tagagatggt cactgttaac gaaagttcca ccgcacaccc    52560
atgtcatgta gtgaggtcaa agaaaggcct caccgtctcc tggcccccaa gcccagtgac    52620
acaatcacag agtgagggaa atctattcat tcattcacca aatttttttt aattttatt     52680
tatttatgat agtcacagag agagagagag agagagagag agagatagag agagaggcag    52740
agacacaggc agagggagaa gcaggctcca tgcaccagga gcccgacgtg ggactcgatc    52800
ccaggtctcc aggatcgcac cctgggccaa aggcaggcgc caaactgctg cgccacccag    52860
ggatccccat tcaccaaatt tttattgttg tgtccagctg tggggcaggc attgctctgg    52920
ggaccgggga tggagtagtg agcagatggg acaaagttcc tgacaaaggt gaggagctaa    52980
cctgccccca ggagagcagg gctttggttt cacacgtcaa aaggggccgg tggtttgaac    53040
ctcagactct aatgcgggac agctcagcct tggcactgtt gaccttttgg gcaggcgcat    53100
cctgtttgga ggcctctgct gcacacacac cgtaggatgt tgagtagcct ctacccactt    53160
gttgccaatg gcaaccccc acccccaccc aagtcgtgac aaccagtgtc tccaggcagc    53220
accagatgtg ccctgggagg gcagactcgt gctggtggag aaccatagtc tgtgatctct    53280
catcgccata tgcaaagagg taaagattgt gccctgcgtc tcggagccgg gagactgcca    53340
tctgtgttca gaacagagaa tcccagattc cggggacaaa tacaaggtga ccggatctct    53400
aaaggttccg cttagccagg agagcacaca gtccctgggg ccgcctcgtg gctgtctccg    53460
gataccctgca gtgctgtcag ttgtgtggaa gggtgactcg cctgcctctg tactgtcccc    53520
aggcccaggc ccagaagtcc atgttcacat cagtgtcctg tggtttaggt gtcaccatga    53580
gagcaaggtc tagccacata tctccttca gggtccccca ctctttcctg tggacagtgg     53640
gcaggggagc gggagatggg gagggtctc acacccaccc ctgctcctag ctgtgctctg     53700
ctacgtaacc tgtgtgtgtg ctctgtgctg ggggggtggt gggtcctgac actctgggac    53760
ccccatgttc cctggaaaca gtgcagtggg ggttctgctg ggctctaaga gggacccgag    53820
gtgggggtct gggggcagct gcagcctctc aactgctcgc agaggggctt aggccaggaa    53880
ggggtgcata cctgctttc caggggctcg cgagagggaa atccgacagg aagagactaa     53940
caactaaatg gggagctgct cccacgtcct agggacagtt ctcactgtcc tgcgacctgg    54000
aggaagttct gttgtctcct ccctctgtgt tcaggcccac gcaccctcaa tccttcccct    54060
ggcaacccc ttgtccttcc cacttcccgt cttcagatca caccgccttt tcccagatat     54120
aacctcccca gcttctagga aacacctccc ttcccagccc ttccctctgc cctgggatgc    54180
tctcccccta ggacagccca gcacggcccg tccccagttc ccatccacac atggcctctg    54240
ctgctggtca gccccagcga gctcctggcg ggacccctcgg accctccggc atcctcctcc   54300
tggtcggtcg cccgctctct acgcccaggt tcctatggca acaccttgga taggaacaca    54360
aacatgcaca cttcctccga caactttca gtgccctggg ctggcggaag ccatatgaag     54420
aaagaaagaa acgctttcat atgggcagcg gaacctgcaa aggcggcccc ctgcccactc    54480
tgatggcagc attttgtgtc actgtgcaga gaaacctcag gcccaggggg gtttcatccc    54540
tccagaagcc agggctgact tgtcccttag gctggggagg gtcagagcca ggcccatgaa    54600
```

```
attttttaggg atacagattt ttaatttctt ctaaaatcag aaggagaaaa aaaaccccaa    54660
cttttatgtt ggaaaaatgg tttaatatct actatttcta tgtgcgtctt tcagtcaaca    54720
cagttgtgaa atatgatttt acatattttg tatggaagca gcagcccaca aagatcccac    54780
gaaagtcaga atgtggccct gcccaaagcc tccatcccaa gtggcatcag ccacagaaac    54840
ttgaaaatgt aggttctagg ttttttgtgt ctctttctcg aagctttcga tgactcccag    54900
gaccagtttc ttgggtgggt tttgaggttt ggagcagctg ggctcccttc ggtggcttct    54960
gtaggacact ggtttcctct aaactcacac ctaggctggg ggcccagctc tgggatgggg    55020
gcgcccacct ccgggctggc actgggacta tagtgtgccc aggaggccct ccctcttcca    55080
aggctaacct cgggggcttg gcttcctccg agacagaagg aaagccttgg tggtagcttg    55140
ggcttggtga tcaatgctgg actggcgagt cgggtcgtcg agatgtttg aagactctcg    55200 tgggccgagg ttttctttgt cctctgggag gacgaggtac ctctcaggat cctgagcagt    55260
tctgagatgc tagggtccca caaacagtag acttcgggct ttattccatt aggatgtgaa    55320
acctcatgac actgggggag aaaaatataa gatagaaaaa gaaagtatgc cgtacattcc    55380
gatctaacac agatcctgtt tttcgtgctc gctgttgtga cccctctgtg gcaccagcct    55440
ctcttagggg tgctatctag agaaagctag agccaagggg ccccagccgt gtggccttct    55500
cggactgtgc tgcagtgctc ggcgctgccc agcttttccc aggatccttg gaccctggac    55560
gggtttctgg actgtgccgg attccattag tgcttactct gcactccttg actttgcctg    55620
tgtgagatgc cagctcctgg aacacgtatc tcgagagata agccaccagc tgtgtggacc    55680
gtgaaagttg aaggcaaccc agaaacagtc tgtgccatgg tccagggaga ggttctgtcc    55740
agggctgtag gcagagccac atggtgggta aagctcagt cctttcccca gcccctcttg    55800
ctgggcagag aacccctccc caaacttcag ggtggtggca gtgggaggtg cagcccctga    55860
ggcctcccta aaagtgtgcc cgaagtgtgg cactgtgccc agcctcaggc caatggggcc    55920
tctctcccgg gggagtgccc ctcgcctggc cctgcgttcc tgactgcatc acatcccact    55980
gactcagttg gcctggccca tggatataaa cagctttgtt gaaaggacag tccatttgtt    56040
tatgctggag agtttttttt tcctgacaaa gcacagcagg ctggcaggag atgtgcccta    56100
gaagagagta aaattgtacc acatgacttc aaaaaaatca cattaacaaa attcaccaag    56160
atggtaacag tggctacctt cgggtaatgc acccatcgtg cattgttctc tcttttatat    56220
ttctggatgt tctattttt ttttcacata aacatttact attttgtaat gaggaaaaag    56280
taagtgaaat aaagggggtgg aatgtgtcac atactatggc attttaaaca aagactaaat    56340
atttgtgatc cagagacccg gggaaggaat aatgaagtgt acgttctcca gcaggtacct    56400
gtcacacagt gtcccctctc agctagtggc tgcggcctac ctggtgacag gtggaacccc    56460
tttgttctta ggtaggtcca taggggtgct tttgtgaata attattttt aaaaaatatt    56520 ttatttattt gagagagcga gagatggaga gcacaagtgg gaggaggggc agaaagagag    56580
ggagaagcag actctgtgct gagcagagtg tccaacacag ggctcgatcc caggaccctg    56640
ggagatgctc aaccattgga accacccagg caccctctt gtgaataatc ataacacaaa    56700
cacccaatga gcccttccag agtgccaggt cttcttctct atgccttatc tgtgtgcctc    56760
atccacacag tactttctga agtgggcact atcatcatgc ccattttaga aaatagaaaa    56820
tgaaggcatt aagaagccag atagatacaa ccctgggatt cgagtccagt taactctcag    56880
ccaccgggcc tgggtgcgaa accactgtgc cattctgctt cttccagaag aagaagaaat    56940
ccaggtggaa cccaaagaaa ggacaggcag gcagaggagg gggccatatg ggaggatgtg    57000
```

| | |
|---|---|
| gatgctcagt ctgggcttgt ttgggtgggc cttgaccata gcatggccag ggagagagtc | 57060 |
| tgggaatagc cagggtcaac actgtcttgt tctttctgta gtgtgctgga catcttcccc | 57120 |
| accgtggtag ctctggctgg ggccagcctg ccccaggacc gacactttga cggtttggat | 57180 |
| gcctccgagg tgctctttgg ctggtcgcag actgggcaca gggtaagtga aggggtgtg | 57240 |
| cgcccttctc aggctcttca ggagattggc cagctgcctc tcatccgggg ctgcctttgt | 57300 |
| gcagagagaa ccatccttgg acgctacatg gaggtggctg ctccagacct agtttgagaa | 57360 |
| agcctgatag atggctcctt tgagacgaac ctctctttct accccacccc tttctcctat | 57420 |
| gatcaatccg gtttgccaat ccagacttaa tttaacacct tggcttagag cgggtgtatg | 57480 |
| gggatgctta ttccccatag catatgattt gttttcacag ttactgaatg ttctgagaca | 57540 |
| tcgtaggcac ctggcacatt tttgttggat gagatggctg agtagtgtga gtgacttgtt | 57600 |
| tatcgtgggg ctccccgact agaatggaac tttcccgaaa gcagggatct cactgagaat | 57660 |
| tccctgtgcg cctcacagtg cctggcaccc acgggcatgc aatcactacg gatctgacga | 57720 |
| ataaatgaat gaacagacac atgaatgaaa cagctcttgg acggcagggc caacgagggc | 57780 |
| tttatgcctc tgacctgccc cctggctcct ggacggcccg acatgtgact ccgcagcccc | 57840 |
| tgcactggct ttgggtttct gcttcccagg gccccagggt cccctcctca tgtgtgctga | 57900 |
| ggcacccggg ggcagtgaca gcccggaagc atcgggccca gtggcctttc catgtcattt | 57960 |
| ccgtgtgttt tcctttcacc aaaaggaaga ggaagtggga ggagggaacc ccaaaccct | 58020 |
| ttgtagggcc cggtgagagc acatggcttc tcagttaggg acccacacat caaagggtct | 58080 |
| atttgcgtct ctaccgaggg tcacatggaa gtgactcaaa tgctgctcag atgtgcggcg | 58140 |
| gcggtcaccc aagccgcccc tgtggctggg cctacccagg gcaggcggcc ctctggcctc | 58200 |
| aagagggccg cccgtgcttc tgtgagcatt cgtgcagttt ctagggctca tcagacgtgc | 58260 |
| ctgaaatgcc ctccgaggaa gcactacttc tcctggcgta tggaatcttc tagaactgca | 58320 |
| gacccttcca ggctgagctg tactgcggag cagcggcgag gccgcaggaa gatggtttcc | 58380 |
| gcctcggggc tggaggttgg cagtgtgtga ccctgggggg ttacgaagga cgtcagtgca | 58440 |
| gaggtgctcc cgagtgtttta ttagcacagc tactaataga ataattgggg tcaccaggaa | 58500 |
| gtgcttcaag gactctgggc tccttgccgt ggccggtctc ctgtggaagc cagctccttc | 58560 |
| gcggtcgctt ccgctctcag gcaggagagc tcactctggt cgctgctttg cgtcgggtca | 58620 |
| tcgaggcccg ggctcggggc ctcacggtta ctggtgtggt gcccggcggt ggctgggtgg | 58680 |
| gggcaccagg caggaggacg ggacccaagc cccagcaccg ttgggggttc gcgtggggga | 58740 |
| cgcggggcgt gtgtgtgcag ctggagtcct gaccacaccc cagggcctgg aaggaaacag | 58800 |
| cctccccgac cgcccgccgg aagccactga tggtatcttc aagagcaaaa gcctgcgggt | 58860 |
| gctggcacct tcgggccacg ccccgcttcc caggaccceta gattcccaca gagtttcgag | 58920 |
| tttgagggca acacaggtag ttgtgggctc tgagtctggt cttttccggc cacctgccga | 58980 |
| acagactaga ataaattgtc ttgagtttgc agaagggagg ccaggaggtg aagtgagtga | 59040 |
| tcacacacac acacacacac acacacacac acacacacac acacctatcc atgtacatac | 59100 |
| gggatacgca catacgtgtc ccccgcccc ccgggagga ttttgagaaa cacaatttac | 59160 |
| ttgtgttcac caccctcggc tgtgtcctgg gcttggttta gaaaacagtt ccagtttcaa | 59220 |
| gaggctcaaa gtaactccta gatgatcatc tcaaaacagg atgcaaatag gcctgagcaa | 59280 |
| tggggctctt ccttattttg caaatgaagt caccgcaagt gggaagtgct gaagccacct | 59340 |
| agggccacgc gcccctggc agcctcccca ggccctaggt gcaggcattt aaaggccagt | 59400 |

```
tgtgggctgt cgggtttcct gcagagcggc cttctcgacc ttcttctcat tgtccccttg   59460
gaggtctctg gggaagtcgg gtggtattta aacccgcag cagctgccac caggctgcat    59520
ggtgggtctt gcacctgggt ctgtgtctgg gcaccgaggg caaccgcgag gaggggggggg   59580 aggggagacg ggtaggagag ggtgcctcca atatcccact gggggcttgc ctgactctcg   59640
aatgcaagct ggaggttgtc acgttgccgt tggtcaagtc acacggcagc tcctggtggc   59700
caccaacaag tccaaatttt gttggcaaag gaaggcttc tttcatggct ctgcaccagc    59760
cagtccaaac cggcctgggg ctgctgtggg tcctaagaca cgtggctcct ccctggaagc   59820
tatacattga ggggacagga gctgggttgc aggctctgga actcccatca cttctcttag   59880
ggaggcccct agtggtgaga ggcgccatcc ccagtggccc accacttctg gagacagagc   59940
tttgcagccc cacctgaggg gactggggga gccctccttg tatgagtgtg tgtgtatgtg   60000
cgcgcgcaca cacaccacat atgcaccagc ccccagggcc taaggagatg ctcccctgct   60060
taaaacgaca aaaccaaatg aaacaaagca aagcaggta agaaaggcaa ccaggaacgt    60120
gcacctgctt tgcagaagac accgtcatct ttgaaattcg gacggggtgt cctccctgcc   60180
ctcccccgag gacctaggac ctgtcttggg ctgtggttca tgtgcacatt tgccagccct   60240
cttcctctgt ggatggggaa ccccagcgcc ctggccagtg tgcccccgag gaaagcaaaa   60300
cccatccctg tttcggggag tgagccatcc tcaagttttg cttcctcttc ctcttggatt   60360
ttggaagttg cctctggtaa cgctgcataa atatcctgga cgtggcagga aactgatgga   60420
gtttctgagg ctcaaacgat gcccacggct tgacctggcg gcggaccgcg actcccacct   60480
cctggatgtc tgagtgcgtc ttaggtcggt tgacaagagt cccccacttc ctgccctctc   60540
cagaaggaaa ccaagcggcc tcctgcggtg acgggcttgg cttcctgcag ggctggcagg   60600
agagtgggtt ttgagttacg acttctttc ctgtttggaa ggagcctgct gtcatcacgc    60660
tggccgggga ccttgcggcg actgtcacga gagcccagca cggaagctgc aggtgtggga   60720
ggagccccgc cctcggcggc atcctctcag agcccgggaa cttggaggga cagctgttta   60780
ctgctccaac agatgtttct cattttttt tttttttagc cccatggaaa ctttgaatca    60840
cgtaagcgcc tttccagtga tatatatcgg tcatgattca taccagggcg gtctcacgct   60900
tccagcccaa acccaccaac cgaccaagga cactggtcat ttattttcta ccaaatcctg   60960
cccttggcaa gcctgaatta ggtgtttccg cttttgtaggg tgatcctttc atctctggcc   61020
cgatgaggga ggatttcctc agtccgagtg gggtagggtt gagtcaaagg tgaggctgtc   61080
catgttaggc cgcgcctggt tccgagacat cacgccgagc cgtcctctcg agcatgcctt   61140
cttaggccac ccttgctcga gggagagcga gaaaatcacc tggatgccga agtcggttct   61200
ccaaagagat ccgaggaaca cctgcgtccg aatccctggg aaggtctgga aggcatgcag   61260
gttcccaggc cctatcttga gcctgagggc tggggcctgg gctggtgtgt gaccagcaca   61320
gtcatctctc acccccatccc cctggcactt aggacagccc cgcagctggt ttaaagagca   61380
ggtgctgtgc cgtcttggaa ctctccaacg ttgaacaagc tttctctcac tttgattttg   61440
cagtggaccc tgcacatgct gtagctggta ctgggcctgc gaatctgacc agagagggg    61500 ccaatctaag taactggcca aatagctatt tcatggaggc atccactccc cggggtgggg   61560
ttggccagtg tggaccacag gccccagtcg gtcagcattt gggaccaggg tagggtgggg   61620
tgggggtgct gggccgggcc ccatgacaga gaaagaaatg ctttccaggg agtccccggg   61680
agcctggctg gttaggaagc tctgctgctc tttctcaggt gctgtttcac cccaacagcg   61740
gggctgctgg agagttcgga gcccttcaga cggtccgcct ggggtcttac aaggccttct   61800
```

-continued

```
acgtcagcgg tgagtcgggt gtgctcagtg caccatcctc cctcaggcct ctggcagtga    61860
gtgtgggctg ccctccttca ggggcgctcc cggcacccag gggcccccca gcacaggccc    61920
tcggccccca cagataggaa aacaaagtct gtctaccgtt cgccgaaatt tccagcaagc    61980
tccgagctag tcagcacact tgacacagcc ctttccccac caagaaccgt ttcgttccat    62040
tgttgtgctt taaatgccag tttggccgaa catgaaatgg gagcttagag atattttaaa    62100
gtgtaattta cttgacaata gactgtttca gaaaatagac tctaggggtt gagttagcaa    62160
accagcagaa ggctctgctt cttggttcat tcgctgaccg tcttcaatgt atattttaga    62220
aatgtgatac tgggtcatga tggttctcaa aaccttccag tggcttcttg ctgcccactg    62280
aattcaggct ccttccatcc tgggtccctc cacttttcca gggtcagttc tccaaggaca    62340
atggccttct tccttggcct tgtatcgaaa tctctctcca ctgcgaggcc ctcccatcaa    62400
attctagtac cttggtcata aaatccaatc tcatcttgcc agctgcgtat gatttggaaa    62460
aactctgata aggatcacat tctgctatat acgccagtta tttgggtaca tgtttgtttt    62520
ttgggagggg tcctgggggg tacacatttt atttccacta ctagttttga gctttaaatt    62580 ttttttttaat gtaagagaga gagagcatat gagagagaga gagagagaga gagagcgaga    62640
gcgcacaagc aacggggagg gtagagggag aagcaggttc ccagctcagt agggagccgc    62700
atgcagggcc aggacccgga gatcatgacc tgagctgaga cgcttaactg actaagccac    62760
ccaggcgccc ctagttttga gctttgtaag gtatttcgtt tttgtggtct ctaagtgctg    62820
agcacagcat cttgtacctc gtagggaccc taacgtcttt cttttagtga atgaaaaaca    62880
aaaacaaaac aaaatccggg acctggtgca gattccaatt tgattcaatt atttaacatc    62940
agggtgttcc aaagaattat ataataaaga acggaaatga ttatccctga ctgtaaatcc    63000
gtgatcctgg agaaaacatg gcataaacac aaaacaagtt ctttgagttc gtaacttgag    63060
ggatattaaa aaagccacaa gaatcgttga tcctccaaaa cctacaatgc aaaccagtca    63120
gatatttgtt atgctttcag atggaaagtt tccagattac agtccttaca ttacattatc    63180
tcagaggtat ggcttctcca ggctgagtta atttcagaag tcacggccct gccagaaagc    63240
ccttggcacc acggtgttgg aatcctgaat gttgctatga agtaatcgga ctgtttagaa    63300
cgatcacaat tggacaggaa ttatgatacc caggggaggg gaggtctgtt ctgaggagtc    63360
accaaggtcc caggagtgtt agcatgagga tgccgagggc agacctctca acagctgaaa    63420
gtgtgtgtgt gtgtgtgtgt gtgtgtcttg agccgagggt ggggcgtgtg acacacatgt    63480
tctgacccct cccttcccct tctcattgag aatctgcatc cctgtttctt aaaactgctt    63540
tcggataaac tacatgtgtt gacatctact acattaggtt agagaacggt gcagagggac    63600
tttatggatg gatttcagg ttgctcctct ctggctccct cctccttcct gggatttcac    63660
gcatcagttc tcttcccttg tggcagccct gagccctggc ccctgacacc tcaagctaaa    63720
gagatgacag ctttctccct gggctcttac tgctccaagc tgcacagact gagggggtc     63780 ctgttgcggg gggagggggc cgcacaaact cctaaatgca gactcaaccc aaggagacct    63840
ctgtctttca ttgatcaaat tctttccggt cttttgcctgc cttggtaact tcctggtgcc    63900
ttcagggttt cttttccccc ctaaatatgt ctagaattcc aaattgttct caataggagg    63960
gctggtccta tgcaagctac ccccgtggt tctcaaagtg gaagtcttaa atttttccaa     64020
gaggagtcca gcccttgctc cactgatcgc aaacctcatt cgctgccctt tactggcaac    64080
gaaggagagc ttaacctgga ctccaaactt ggggcaaaga cagtgactct gaacgacccg    64140
aatgtcaacc acagcaggaa aaccattaag gagggctgcc taaaaagctg tgtggtttgc    64200
```

-continued

```
ccattcttct tggggaagcc aagagtttct ctcacatata tcagtgccag gaagagctgg    64260 gcttccctg agccgctgag aagtttctac cctgttgttt ggctgctagg aagctcggat    64320
gcaaaatagg catttgggat ttactgtatg tctgatggct gtcccttgcc ttgattgctt    64380
tcatttattc aatcatatta actcctgtcc aataccttaa ctactttgt atggaaaagg    64440 caaaaaaaa aaaaaaaaa aaaaaaaaa agtcacccga atcactaact gctgctgcca    64500
gtactccatt tttgttactc tttggaggct gccttcatgg ccagattcaa attcatgtaa    64560
gaatctcaat tgcaacccaa agtgaaatta ctcacctcgc cttcctgccc agtccaccaa    64620
actgagtatc atggtgttca agaaatcagt gtttggaaaa agaaaaaaat caaatttcct    64680
cacaaagggt agagatgaga gagaactggt tgactgtcga gtcatattgg ctctgaaggc    64740
aagtcccgga gaagttccag atcactctgg gcaagaggag catcactggt ctgagcacca    64800
aaaatctcaa ggtgacttga caggcagaat ggtcacttga atattcaagt cctgggatgt    64860
ttggattaat gtaaaatcaa tccgaattct cctctttcca ccatagggcc aaaactgggt    64920
ctgacgagtt atttgctgtc acctcctctc taggcggagc caaagcctgt gatggggacg    64980
tcggacggga gcagcatcat gaccctcccc ttatttttaa cctggaagat gatgttgcag    65040
aagctgtgcc tctagataga ggtagcgccg aataccaggg cgtcctgccc aaggtcagag    65100
agattcttgc agatgttctt ctagacattg ctggggacaa cacctccaga gcggattaca    65160
ctcgccatcc ttcggtgacc ccctgctgca atccccacca cgtcgcctgc cgttgccaag    65220
ccaccggatg gaccgatttc cccacaggca gatgttagga agcgagacag ggcaagttca    65280
cactccagct ccggatgctg                                              65300
```

<210> SEQ ID NO 3
<211> LENGTH: 22
<212> TYPE: DNA
<213> ORGANISM: Artificial
<220> FEATURE:
<223> OTHER INFORMATION: primer

<400> SEQUENCE: 3
ttccatccct ttcacagtct tt                                            22

<210> SEQ ID NO 4
<211> LENGTH: 23
<212> TYPE: DNA
<213> ORGANISM: Artificial
<220> FEATURE:
<223> OTHER INFORMATION: primer

<400> SEQUENCE: 4
acgatggttt tcaaatctta cct                                           23

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gttttcaaat cttaccttct                                               20

<210> SEQ ID NO 6
<211> LENGTH: 20
<212> TYPE: DNA
<213> ORGANISM: Artificial
<220> FEATURE:

<223> OTHER INFORMATION: primer

<400> SEQUENCE: 6
ctcctggcct ggctttctgt                                               20

<210> SEQ ID NO 7
<211> LENGTH: 18
<212> TYPE: DNA
<213> ORGANISM: Artificial
<220> FEATURE:
<223> OTHER INFORMATION: primer

<400> SEQUENCE: 7
atccccgtga cgtagccg                                                 18

<210> SEQ ID NO 8
<211> LENGTH: 15
<212> TYPE: DNA
<213> ORGANISM: Artificial
<220> FEATURE:
<223> OTHER INFORMATION: primer

<400> SEQUENCE: 8
ttgtgcgtga ctccg                                                    15

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9
ctcttctttc gggtggacct                                               20

<210> SEQ ID NO 10
<211> LENGTH: 23
<212> TYPE: DNA
<213> ORGANISM: Artificial
<220> FEATURE:
<223> OTHER INFORMATION: primer

<400> SEQUENCE: 10
cagcagacag tagggaaact gat                                           23

<210> SEQ ID NO 11
<211> LENGTH: 16
<212> TYPE: DNA
<213> ORGANISM: Artificial
<220> FEATURE:
<223> OTHER INFORMATION: primer

<400> SEQUENCE: 11
ggaagtggtt ctttgc                                                   16

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
caaacagtac ggcactctga a                                             21

<210> SEQ ID NO 13

```
<211> LENGTH: 27
<212> TYPE: DNA
<213> ORGANISM: Artificial
<220> FEATURE:
<223> OTHER INFORMATION: primer

<400> SEQUENCE: 13
gtgcaagtgt ttatttcaat aactatg                                        27

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
tttgttccag agccaatgtt t                                              21

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
gaaggctcgg ctgtaaatct t                                              21

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
gttcctgggg gtgactttct                                                20

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17
atctgcctgt ggggaaatc                                                 19

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18
gcttctcctt caaccaggac t                                              21

<210> SEQ ID NO 19
<211> LENGTH: 21
<212> TYPE: DNA
<213> ORGANISM: Artificial
<220> FEATURE:
<223> OTHER INFORMATION: primer

<400> SEQUENCE: 19
```

```
tacagagaac acccggatga c                                              21

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
caaagagcag ctcaacctca c                                              21

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
tcttttcctg ccagcgagta                                                20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
gtcaacagac ctgggcatta                                                20

<210> SEQ ID NO 23
<211> LENGTH: 26
<212> TYPE: DNA
<213> ORGANISM: Artificial
<220> FEATURE:
<223> OTHER INFORMATION: primer

<400> SEQUENCE: 23
cgtgaacttc aaatgatatg agaatg                                         26

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
gcacataagt gtcggtcagc                                                20

<210> SEQ ID NO 25
<211> LENGTH: 24
<212> TYPE: DNA
<213> ORGANISM: Artificial
<220> FEATURE:
<223> OTHER INFORMATION: primer

<400> SEQUENCE: 25
aagaggactt tcactgcatc taca                                           24

<210> SEQ ID NO 26
<211> LENGTH: 22
<212> TYPE: DNA
<213> ORGANISM: Artificial
<220> FEATURE:
```

<223> OTHER INFORMATION: primer

<400> SEQUENCE: 26
aaactcaagc acttctgtgc aa                                              22

<210> SEQ ID NO 27
<211> LENGTH: 23
<212> TYPE: DNA
<213> ORGANISM: Artificial
<220> FEATURE:
<223> OTHER INFORMATION: primer

<400> SEQUENCE: 27
tgtcatgaaa gatgattcca atg                                             23

<210> SEQ ID NO 28
<211> LENGTH: 27
<212> TYPE: DNA
<213> ORGANISM: Artificial
<220> FEATURE:
<223> OTHER INFORMATION: primer

<400> SEQUENCE: 28
ggagttttta aagataatgg gacttca                                         27

<210> SEQ ID NO 29
<211> LENGTH: 23
<212> TYPE: DNA
<213> ORGANISM: Artificial
<220> FEATURE:
<223> OTHER INFORMATION: primer

<400> SEQUENCE: 29
tagacggcca agaggacata gaa                                             23

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
ctctcctggc tgttctttgg                                                 20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
aagtggctct tccgaaggtt                                                 20

<210> SEQ ID NO 32
<211> LENGTH: 24
<212> TYPE: DNA
<213> ORGANISM: Artificial
<220> FEATURE:
<223> OTHER INFORMATION: primer

<400> SEQUENCE: 32 acccctgtg cacctcatca ctta                                             24

<210> SEQ ID NO 33

```
<211> LENGTH: 24
<212> TYPE: DNA
<213> ORGANISM: Artificial
<220> FEATURE:
<223> OTHER INFORMATION: primer

<400> SEQUENCE: 33
aggtcactgt ctgtacacgt agtg                                          24

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
acatcaggtg aagagcttgc                                               20

<210> SEQ ID NO 35
<211> LENGTH: 18
<212> TYPE: DNA
<213> ORGANISM: Artificial
<220> FEATURE:
<223> OTHER INFORMATION: primer

<400> SEQUENCE: 35
gaagttggct ggggaagg                                                 18

<210> SEQ ID NO 36
<211> LENGTH: 25
<212> TYPE: DNA
<213> ORGANISM: Artificial
<220> FEATURE:
<223> OTHER INFORMATION: primer

<400> SEQUENCE: 36
agttagactg ccttctgatg aagtg                                         25

<210> SEQ ID NO 37
<211> LENGTH: 25
<212> TYPE: DNA
<213> ORGANISM: Artificial
<220> FEATURE:
<223> OTHER INFORMATION: primer

<400> SEQUENCE: 37
tgtctatcga ttcttcccaa ctaac                                         25

<210> SEQ ID NO 38
<211> LENGTH: 25
<212> TYPE: DNA
<213> ORGANISM: Artificial
<220> FEATURE:
<223> OTHER INFORMATION: primer

<400> SEQUENCE: 38
gcacgactcc aggaatatag tagaa                                         25

<210> SEQ ID NO 39
<211> LENGTH: 25
<212> TYPE: DNA
<213> ORGANISM: Artificial
<220> FEATURE:
<223> OTHER INFORMATION: primer
```

```
<400> SEQUENCE: 39
tgggacttaa acgctaaatt gtatg                                    25

<210> SEQ ID NO 40
<211> LENGTH: 25
<212> TYPE: DNA
<213> ORGANISM: Artificial
<220> FEATURE:
<223> OTHER INFORMATION: primer

<400> SEQUENCE: 40
ttgtacatta tctgttctac ctcgg                                    25

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
tcttcagcag gcctttctc                                           20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
acatcaggtg aagagcttgc                                          20

<210> SEQ ID NO 43
<211> LENGTH: 18
<212> TYPE: DNA
<213> ORGANISM: Artificial
<220> FEATURE:
<223> OTHER INFORMATION: primer

<400> SEQUENCE: 43
gaagttggct ggggaagg                                            18

<210> SEQ ID NO 44
<211> LENGTH: 21
<212> TYPE: DNA
<213> ORGANISM: Artificial
<220> FEATURE:
<223> OTHER INFORMATION: primer

<400> SEQUENCE: 44
ttccaggggc actttctact t                                        21

<210> SEQ ID NO 45
<211> LENGTH: 21
<212> TYPE: DNA
<213> ORGANISM: Artificial
<220> FEATURE:
<223> OTHER INFORMATION: primer

<400> SEQUENCE: 45
tctccctctg cctatgtctc a                                        21

<210> SEQ ID NO 46
<211> LENGTH: 21
<212> TYPE: DNA
```

```
<213> ORGANISM: Artificial
<220> FEATURE:
<223> OTHER INFORMATION: primer

<400> SEQUENCE: 46
gggcgttgaa cagatcaaat a                                          21

<210> SEQ ID NO 47
<211> LENGTH: 21
<212> TYPE: DNA
<213> ORGANISM: Artificial
<220> FEATURE:
<223> OTHER INFORMATION: primer

<400> SEQUENCE: 47
tcatctccac accaggagac t                                          21

<210> SEQ ID NO 48
<211> LENGTH: 21
<212> TYPE: DNA
<213> ORGANISM: Artificial
<220> FEATURE:
<223> OTHER INFORMATION: primer

<400> SEQUENCE: 48
gggctctgag tctggtcttt t                                          21

<210> SEQ ID NO 49
<211> LENGTH: 21
<212> TYPE: DNA
<213> ORGANISM: Artificial
<220> FEATURE:
<223> OTHER INFORMATION: primer

<400> SEQUENCE: 49
acgtatgtgc gtatcccgta t                                          21

<210> SEQ ID NO 50
<211> LENGTH: 22
<212> TYPE: DNA
<213> ORGANISM: Artificial
<220> FEATURE:
<223> OTHER INFORMATION: primer

<400> SEQUENCE: 50
ttccatccct ttcacagtct tt                                         22

<210> SEQ ID NO 51
<211> LENGTH: 23
<212> TYPE: DNA
<213> ORGANISM: Artificial
<220> FEATURE:
<223> OTHER INFORMATION: primer

<400> SEQUENCE: 51
acgatggttt tcaaatctta cct                                        23

<210> SEQ ID NO 52
<211> LENGTH: 22
<212> TYPE: DNA
<213> ORGANISM: Artificial
<220> FEATURE:
<223> OTHER INFORMATION: primer
```

<400> SEQUENCE: 52
tatctggcga atgagatcct ct                                              22

<210> SEQ ID NO 53
<211> LENGTH: 22
<212> TYPE: DNA
<213> ORGANISM: Artificial
<220> FEATURE:
<223> OTHER INFORMATION: primer

<400> SEQUENCE: 53
cgttttcgta gcaaaaggag tt                                              22

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
aggctattaa cccctgatcg                                                 20

<210> SEQ ID NO 55
<211> LENGTH: 22
<212> TYPE: DNA
<213> ORGANISM: Artificial
<220> FEATURE:
<223> OTHER INFORMATION: primer

<400> SEQUENCE: 55
cgatgcctta cttaaacaaa cc                                              22

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
tgtcatcctg catccaatgt                                                 20

<210> SEQ ID NO 57
<211> LENGTH: 20
<212> TYPE: DNA
<213> ORGANISM: Artificial
<220> FEATURE:
<223> OTHER INFORMATION: primer

<400> SEQUENCE: 57
caatttactt ttgggcgtca                                                 20

<210> SEQ ID NO 58
<211> LENGTH: 20
<212> TYPE: DNA
<213> ORGANISM: Artificial
<220> FEATURE:
<223> OTHER INFORMATION: primer

<400> SEQUENCE: 58
tcaggccttt gatgatttca                                                 20

<210> SEQ ID NO 59
<211> LENGTH: 21
<212> TYPE: DNA

<213> ORGANISM: Artificial
<220> FEATURE:
<223> OTHER INFORMATION: primer

<400> SEQUENCE: 59
cagggctggc atttatgtaa g       21

<210> SEQ ID NO 60
<211> LENGTH: 21
<212> TYPE: DNA
<213> ORGANISM: Artificial
<220> FEATURE:
<223> OTHER INFORMATION: primer

<400> SEQUENCE: 60
cccccaacaa tcaaatgttt a       21

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
aatgcagcta tatgggccac       20

<210> SEQ ID NO 62
<211> LENGTH: 22
<212> TYPE: DNA
<213> ORGANISM: Artificial
<220> FEATURE:
<223> OTHER INFORMATION: primer

<400> SEQUENCE: 62
ggatctgtgt ttcttcgtta gc       22

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
ttgattaaag agcagcttag cc       22

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
ctcttctttc gggtggacct       20

<210> SEQ ID NO 65
<211> LENGTH: 23
<212> TYPE: DNA
<213> ORGANISM: Artificial
<220> FEATURE:
<223> OTHER INFORMATION: primer

<400> SEQUENCE: 65
cagcagacag tagggaaact gat       23